US007265267B1

(12) United States Patent
De Veylder et al.

(10) Patent No.: US 7,265,267 B1
(45) Date of Patent: *Sep. 4, 2007

(54) CYCLIN-DEPENDENT KINASE INHIBITORS AND USES THEREOF

(75) Inventors: Lieven De Veylder, Drongen (BE); Tom Beeckman, Merelbeke (BE); Dirk Inze, Moorsel-Aalst (BE); Wim Van Camp, Sint-Denijs-Westrem (BE); Luc Krols, Kapelen (BE)

(73) Assignee: CropDesign N.V., Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,735

(22) Filed: May 18, 2000

Related U.S. Application Data

(63) Continuation-in-part of application No. 09/526,597, filed on Mar. 16, 2000, now Pat. No. 6,710,227.

(30) Foreign Application Priority Data

| Sep. 16, 1997 | (EP) | ................................. 97202838 |
| Dec. 24, 1997 | (EP) | ................................. 97204111 |
| Sep. 16, 1998 | (EP) | ..................... PCT/EP98/05895 |

(51) Int. Cl.
*C12N 15/82* (2006.01)
*A01H 5/00* (2006.01)
*A01H 5/02* (2006.01)

(52) U.S. Cl. ...................... 800/290; 800/298; 435/419; 435/468

(58) Field of Classification Search ............. 435/320.1, 435/419, 468; 800/278, 298, 290
See application file for complete search history.

(56) References Cited

U.S. PATENT DOCUMENTS

| 5,550,038 | A | * | 8/1996 | Goodman et al. .......... 435/70.1 |
| 5,750,862 | A | | 5/1998 | John et al. |
| 6,087,175 | A | | 7/2000 | John et al. |
| 6,710,227 | B1 | * | 3/2004 | Inze et al. ................... 800/278 |

FOREIGN PATENT DOCUMENTS

| WO | WO92 09685 | | 6/1992 |
| WO | WO93 15213 A | | 8/1993 |
| WO | WO96 31534 A | | 10/1996 |
| WO | WO 97 20842 A | | 10/1996 |
| WO | WO 97 16447 A | | 5/1997 |
| WO | WO 97 26327 A | | 7/1997 |
| WO | WO97 26327 A | | 7/1997 |
| WO | WO99 14331 | | 3/1999 |
| WO | WO99/64599 | * | 12/1999 |
| WO | WO99 64599 | | 12/1999 |
| WO | WO 00 60087 | | 10/2000 |

OTHER PUBLICATIONS

Riou-Khamlichi et al, "Cytokinin Activation of *Arabdidopsis* Cell Division through a D-Type Cyclin", Mar. 1999, Science Vo. 283, vol. 283, pp. 1541-1544.*

Cockcroft et al, "Cyclin D control of growth rate in plants", Jun. 2000, Nature vol. 405, pp. 575-579.*

Toyoshima et al. p27, a novel inhibitor of G1 cyclin-CDK protein kinase activity, is related to p21. Cell, Jul. 15, 1994, vol. 78, pp. 67-74.*

Zhou et al. Plant CDK inhibitors: studies of interactions with cell cycle regulators in the yeast two-hybrid sytem and functional comparisons in transgenic *Arabidopsis* plants. Plant Cell Reports, 2002, vol. 20, pp. 967-975.*

Wang et al. ICK1, a cyclin-dependent protein kinase inhibitor from *Arabidopsis thaliana* interacts with both Cdc2a and CycD3 and its expression is induced by abscisic acid. The Plant Journal, 1998, vol. 15, No. 4, pp. 501-510.*

(Continued)

*Primary Examiner*—Cynthia Collins
(74) *Attorney, Agent, or Firm*—Ann R. Pokalsky; Dilworth & Barrese

(57) ABSTRACT

Provided are DNA sequences encoding cyclin-dependent kinase inhibitor(s) as well as to methods for obtaining the same. Furthermore, vectors comprising said DNA sequences are described, wherein the DNA sequences are operatively linked to regulatory elements allowing expression in prokaryotic and/or eukaryotic host cells. In addition, proteins encoded by said DNA sequences, antibodies to said proteins and methods for their production are provided. Furthermore, regulatory sequences which naturally regulate the expression of the above described DNA sequences are described. Also described is a method for controlling or altering growth characteristics of a plant and/or a plant cell comprising introduction and/or expression of one or more cyclin-dependent kinase inhibitor(s) functional in a plant or parts thereof and/or one or more DNA sequences encoding such proteins. Also provided is a process for disruption plant cell division by interfering in the expression or activity of a cyclin-dependent protein kinase inhibitor using a DNA sequence according to the invention wherein said plant cell is part of a transgenic plant. Further described are diagnostic compositions comprising the aforementioned DNA sequences, proteins, antibodies and regulatory sequences. Methods for the identification of compounds being capable of activating or inhibiting the cyclin-dependent kinase inhibitors are described as well. Furthermore, transgenic plant cells, plant tissue and plants containing the above-described DNA sequences and vectors are described as well as the use of the aforementioned DNA sequences, vectors, proteins, antibodies, regulatory sequences and/or compounds identified by the method of the invention in plant cell and tissue culture, plant breeding and/or agriculture.

33 Claims, 14 Drawing Sheets

OTHER PUBLICATIONS

U.S. Appl. No. 10/688,291, filed Oct. 2003, Inze et al.*
Faustinella F et al. Structural and functional roles of highly conserved serines in human lipoprotein lipase. Evidence that serine 132 is essential for enzyme catalysis. J Biol Chem. May 25, 1991;266(15):9481-5.*
Ogata S et al. Identification of the active site residues in dipeptidyl peptidase IV by affinity labeling and site-directed mutagenesis. Biochemistry. Mar. 10, 1992;31(9):2582-7.*
Zhu JK et al. Isoprenylation of the plant molecular chaperone ANJ1 facilitates membrane association and function at high temperature. Proc Natl Acad Sci U S A. Sep. 15, 1993;90(18):8557-61.*
Jasinski S. et al. The CDK inhibitor NtKIS1a is involved in plant development, endoreduplication and restores normal development of cyclin D3; 1-overexpressing plants. J Cell Sci. Mar. 1, 2002;115(PT 5):973-82.*
De Veylder L. et al. Functional analysis of cyclin-dependent kinase inhibitors of *Arabidopsis*. Plant Cell. Jul. 2001;13(7):1653-68.*
Burssens S., et al. (1998) "The cell cycle in *Arabidopsis*", *Plant Physiol. Biochem* 36(1-2): 9-19.
Burssens S., et al. (1998) "Identification of novel cell cycle genes in *Arabidopsis thaliana*", current abstract *Plant Science and Biotechnology in Agriculture 36*.
Chen, J., et al. (1996) "Cyclin-Binding Motifs Are Essential For The Function Of p21$^{CIP1}$", *Molcular and Cellular Biology 16*(9): 4673-4682.
de Almedia Engler. J., et al. (1999) "Molecular Markers And Cell Cycle Inhibitors Show The Importance Of Cell Cycle Progression In Nematode-Induced Galls And Syncytia", *Plant Cell 11*: 793-808.
Doerner, P., et al. (Apr. 11, 1996) "Control of root growth and development by cyclin expression", *Nature 380*:520-523.
Doonan, J., (1996) "Plant Growth: Roots In The Cell Cycle", *Current Biology 6*(7): 788-789.
Forsburg, Susan L. (2000) "Themes and variations: the First Salk Institute Cell Cycle Meeting, Jun. 18-22, 1999", *Biochimica et Biophysica Acta 1470*: R13-R16.
Fountain, M.D., (Nov. 27, 1997) "*Chenopodium rubrum* G1 cyclin-dependent kinase inhibitor mRNA, complete cds." EMBL Accession No. AJ002173.
Hemerly A.S., et al. (1999) "Cell Cycle Control And Plant Morphogenesis: Is There An Essential Link?" *Bioessay 21*:29-37.
Hemerly, A., et al., (Dec. 1993) "cdc2a Expression in *Arabidopsis* is Linked with Competence Cell Division", *The Plant Cell 5*: 1711-1723.
Hemerly et al. (1995) "Dominant Negative Mutants of the CDC2 Kinase Uncouple Cell Division From Iterative Plant Development", *Embo Journal 14*(16): 3925-3936.

Hinds, Phil (1999) "The cell cycle Cold Spring Harbor, May 20-24, 1998", *Biochimica et Biophysica Act 1423*:R63-R67.
Huntley, Rachel P., et al. (1999) "The Plant Cell Cycle", *Plant Biology 2*: 447-453.
Inze, D., et al. (1999) "Trends In Plant Cell Cycle Research", *Plant Cell 11*(1): 1-4.
Jacqmard, A., et al. (1999) "Expression Of CKS1At In *Arabidopsis thaliana* Indicated A Role For The Protein In Both The Mitotic And The Endoreduplication Cycle", *Planta 207*: 496-504.
LaBaer, J., et al. (1997) "New Functional Activities For The p21 Family of CDK Inhibitors", *Genes & Development 11*: 847-862.
Lui, H., et al. (2000) "The *Arabidopsis* Cdc2a-Interacting Protein ICK2 Is Structurally Related To ICK1 and is a potent inhibitor of cyclin-dependent kinase activity in vitro", *Plant Journal 21*(4): 379-385.
Mironov, V., et al. (1999) "Cyclin-Dependent Kinases And Cell Division In Plants-The Nexus", *Plant Cell*. 11: 509-522.
Nakamura Y. (Apr. 14, 1998) "*Arabidopsis thaliana* genomic DNA, chromosome 5, TAC clone:K24G6" EMBL Accession No. AB012242.
Nakayama, K. et al. (1998) "Cip/Kip Cyclin-Dependent Kinase Inhibitors: Brakes Of The Cell Cycle Engine During Development", *Bioessays 20*: 1020-1029.
Niebel, A., et al. (1996) "Induction of cdc2a and cyc1At Expression in *Arabidopsis thaliana* During Early Phases of Nematode-Induced Feeding Cell Formation", *Plant Journal 10*(6): 1037-1043.
Planchais, S., (1997) "Roscovitine, a novel cyclin-dependent kinase inhibitor, characterizes restriction point and G2/M transition in tobacco By-2 cell suspension", *The Plant Journal 12*(1):191-202.
Pyke, K, et al. (1999) "Cellular Differentiation and Leaf Morphogenesis in *Arabdopsis*", *Critical Reviews in Plant Sciences 18*(4): 527-546.
Reed, S. I. (1996) "G1/S Regulatory Mechanisms From Yeast to Man", *Prog. Cell Cycle Res. 2*: 15-27.
Veylder De, et al. (1997) "The *Arabidopsis* CKS1 At Protein Binds The Cyclin-Dependent Kinases CDC2AAT and CDC2BAT", *Febs Letters 412 No. 3 and 4*: 446-452.
Wang, H., et al. (1997) "A Plant Cyclin-Dependent Kinase Inhibitor Gene", *Nature 386*: 451-452.
Wang, H., et al. (1998) "ICK1, A Cyclin-Dependent Protein Kinase Inhibitor From *Arabidopsis thaliana* Interacts With Both Cdc2a and CycD3, And Its Expression Is Induced By Abscisic Acid", *Plant Journal 15*(4): 501-510.
Wang H., et al. (1997) "*Arabidopsis thaliana* cyclin-dependent kinase inhibitor protein (ICK1) mRNA, complete cds", EMBL Accession No. U94772, Apr. 29, 1997.

* cited by examiner

```
FL39      1  MAAV.........R..RRCP..................DVVE..........
ICK1      1  M..V.........RKYRKAK..................GIVE..........
FL67      1  M........GKYLRKSKIDGAGAGAGGGGGGGGGGESSIALMDV...VSPS..
FL66      1  M........GKYMKKSKITG..............DISVMEVSKATAPS..
ALFCDKI   1  M........GKYMKKLK.....................SKSESPSPN
CrCKI     1  MAAAATPTSSPKKIKK..................VSKS......

FL39     14  ..........................ENGVTT..................
ICK1     14  ..........................A.GVSS..................
FL67     41  ..................SSSSLGVLTR.AKSLALQQQQQRCLLQKPSSP
FL66     27  ..............P....GVRTRAAKTLAI....KR..LNSSAAD
ALFCDKI  19  STPTPSPSPSPTPITTNSPPPTTPNSSDGVRTR.ARTLAIE........NS....
CrCKI    22  .............................................

FL39     20  .........................TT..VKRRKMEEEVDLVES
ICK1     19  .........................TY..MQLR..........S
FL67     72  SSLPPTSASPNPPSKQKMKKKQQQMN.....C...CGGY.L.QLR.........S
FL66     49  SALP................N......DSSC..Y.L.QLR.........S
ALFCDKI  61  ...............NNQNQNLSVSSD....SY.L.QLR.........N
CrCKI    22  ..........................SYNIPQLR.........S

FL39     37  RIILSPCVQATNRGGIV.AR........................
ICK1     26  R..........R..IVYVR........................
FL67    108  R...........RLQKKP.....PIVVIRSTKRRQQQRRNETCGRNPN
FL66     64  R...........RLE.KPSSLIEE..........KQ.........P.
ALFCDKI  80  R...........RLKR......ELIRQHSAKRNK........GHDGN
CrCKI    31  R...........R.................K.............N

FL39     56  ..........NSACASE..TSV....VIVRRRDSPPVEEQ..........
ICK1     33  ..........SEKSSSV....SVV........................
FL67    140  ...PRSNLDSIRGDGSRS..DSVSE..SVVFGKDKDLTSE.I.....NKPTE...
FL66     79  ...PIVHRSGIKESGSRSRVDSVN...SVP......VAQSS....NEDECGDNF
ALFCDKI 102  ...PK...SPI...G.....DSHAEEKTV........QKSPEPENAE..GK..
CrCKI    35  LSAE........................................

FL39     80  ..CQIEEEESSV.SCCSTSEE.KSKRRIEGVDLEE..NNGDDRET.ETSWIY...
ICK1     43  .......GDNGVSSSCSGSNEYKKK...ELIHLEEEDKDGD...T.ETS.TYRRG
FL67    180  ........GLN...................FDLEEHTQSFNRITRES.......
FL66    117  VSVQVSCGENSLG................F...GSRH.....ETRES.......
ALFCDKI 129  ........ENA.................EDTE.....RSARET........
CrCKI    39  ........EN...................EAEL.....ET..........

FL39    125  ..............DDLNKSEESMNMDS..SSVAVEDVE..........
ICK1     83  TKRKLCENLREEEKEELSKSME..NYSSEFES.AVK..E..........
FL67    202  TE.............CS.............LIRRPEIM.....TT.....EG
FL66    140  TE.............CN.............FVEDMEIV.....VT.....EG
ALFCDKI 142  TE............VH..............LIMRADVIRPPRPII.RRT.FE.
CrCKI    47  TELEVAAVVEEEEVANCS..................SSEVI.....TLARSDEPP
```

Figure 1

```
FL39     148 SRRRL........................................RRSLHETV..
ICK1     117 S...LDCCCS...................................GRKTMEETVTA
FL67     218 SSTKLNIC..VS.................................ESNQR..EDSLSR
FL66     156 SSTR.SMCRATK.................................EYTRE..QDNVI.
ALFCDKI  166 ..T..........................................EANPK..TE....
CrCKI     79 S......CCSSNYDQLSSSEPEVVKDDDGLGNRTADPEVESGEASSK...QK...E

FL39     161 ......K..................EAELEDFFQVAEKDLRNLLECSMK
ICK1     135 EEEEKAKLMT...............EMPTESEIEDFIVEADKQLKEKE...KKK
FL67     239 SHRRR..........PTT.......E...EMDEFSSGAEEEQQKQFIE...K
FL66     177 ...............PTT.......S...EMEEFFAYAEQQQQFLFME...K
ALFCDKI  174 ....Q..........PTI.......EISREFEEICAKHEAEQQREFME...K
CrCKI    123 SHRTEAREATKLDDQDYEATKSTVQIKMESDSEIEEFFAVAEKDLOKRESE...K

FL39     187 ..........................................YNFDFEKDEPLGGGRYE
ICK1     171 ..........................................YNFDFEKEKPL.EGRYE
FL67     268 YVFPRFICSVLLVMSFQFVLFFSFGLVSLMVSVNSFFRYNFDPVNEQPLP.GREE
FL66     201 ..........................................YNFDIVNLIPLS.GRYE
ALFCDKI  202 ..........................................YNFDPVTEQPLP.GRYE
CrCKI    175 ..........................................YNFDIVKLVPLK.GRYD

FL39     204 WVKINE
ICK1     187 WVKIE
FL67     322 WTKVDD
FL66     217 WVQVKE
ALFCDKI  218 WEKVSE
CrCKI    191 WVPINE
```

FIGURE 1 (continued)

Figure 2B
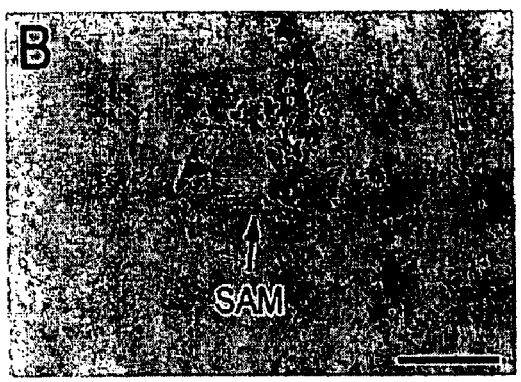
Figure 2C
Figure 2D
Figure 2E
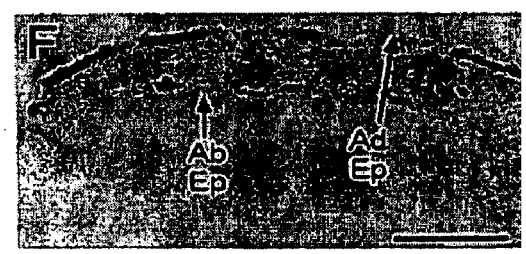
Figure 2F Figure 4A
Figure 4B
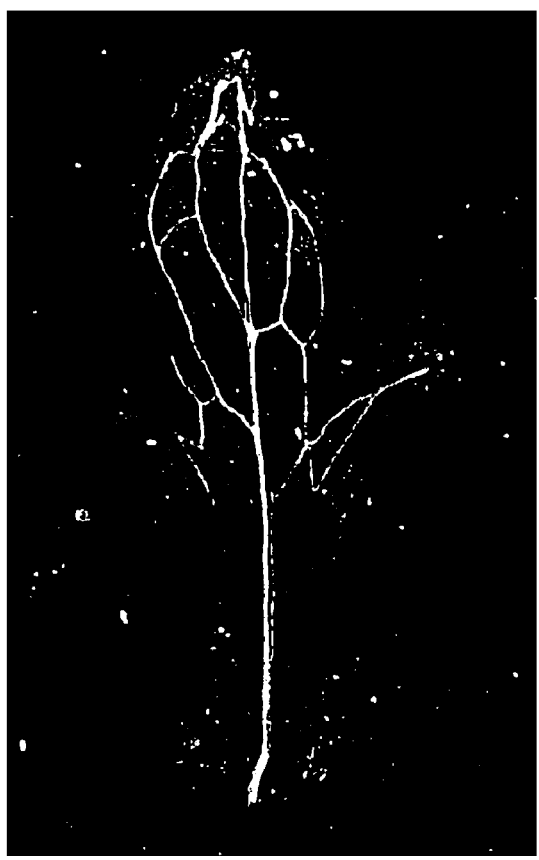

Narrow leaves: Whole-mount study of cleared leaves (1st rosette leaves)
WT: DIC image of adaxial epidermis
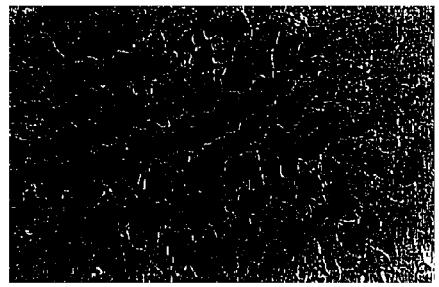
35SFL39: DIC image of adaxial epidermis (same magnification as WT)
WT: DIC image of palissade layer
35SFL39: DIC of palissade
WT: DIC image of spongy parenchyma
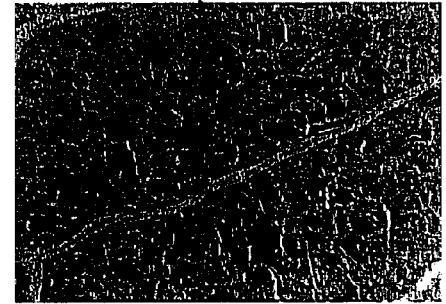
35SFL39: DIC image of spongy parenchyma
WT: DIC image of abaxial epidermis
35SFL39: DIC image of abaxial epidermis
Figure 7

Control

ICK2

WT seed  35SFL39 seed

CYCLIN-DEPENDENT KINASE INHIBITORS AND USES THEREOF

CROSS REFERENCE TO RELATED APPLICATION

The present application is a continuation-in-part application of U.S. application Ser. No. 09/526,597, filed Mar. 16, 2000 now U.S. Pat. No. 6,710,227

BACKGROUND OF THE INVENTION

The present invention relates to DNA sequences encoding cyclin-dependent kinase inhibitors as well as to methods for obtaining the same. The present invention also provides vectors comprising said DNA sequences, wherein the DNA sequences are operatively linked to regulatory elements allowing expression in prokaryotic and/or eukaryotic host cells. In addition, the present invention relates to the proteins encoded by said DNA sequences, antibodies to said proteins and methods for their production. Furthermore, the present invention relates to regulatory sequences which naturally regulate the expression of the above described DNA sequences. The present invention also relates to a method for controlling or altering growth characteristics of a plant and/or a plant cell comprising introduction and/or expression of one or more cyclin-dependent kinase inhibitors functional in a plant or parts thereof and/or one or more DNA sequences encoding such proteins. Also provided by the present invention is a process for disruption plant cell division by interfering in the expression of a substrate for cyclin-dependent protein kinase using a DNA sequence according to the invention wherein said plant cell is part of a transgenic plant. The present invention further relates to diagnostic compositions comprising the aforementioned DNA sequences, proteins and antibodies. The present invention also relates to methods for the identification of compounds being capable of activating or inhibiting the cell cycle. Furthermore, the present invention relates to transgenic plant cells, plant tissue and plants containing the above-described DNA sequences and vectors as well as to the use of the aforementioned DNA sequences, vectors, proteins, antibodies, regulatory sequences and/or compounds identified by the method of the invention in plant cell and tissue culture, plant breeding and/or agriculture.

Cell division is fundamental for growth in humans, animals and plants. Prior to dividing in two daughter cells, the mother cell needs to replicate its DNA. The cell cycle is traditionally divided into 4 distinct phases:

G1: the gap between mitosis and the onset of DNA synthesis;

S: the phase of DNA synthesis;

G2: the gap between S and mitosis;

M: mitosis, the process of nuclear division leading up to the actual cell division.

The distinction of these 4 phases provides a convenient way of dividing the interval between successive divisions. Although they have served a useful purpose, a recent flurry of experimental results, much of it as a consequence of cancer research, has resulted in a more intricate picture of the cell cycle's "four seasons" (Nasmyth, Science 274, 1643–1645, 1996; Nurse, Nature, 344, 503–508, 1990). The underlying mechanism controlling the cell cycle control system has only recently been studied in greater detail. In all eukaryotic systems, including plants, this control mechanism is based on two key families of proteins which regulate the essential process of cell division, namely protein kinases (cyclin-dependent kinases or CDKs) and their activating associated subunits, called cyclins. The activity of these protein complexes is switched on and off at specific points of the cell cycle. Particular CDK-cyclin complexes activated at the G1/S transition trigger the start of DNA replication. Different CDK-cyclin complexes are activated at the G2/M transition and induce mitosis leading to cell division. Each of the CDK-cyclin complexes execute their regulatory role via modulating different sets of multiple target proteins. Furthermore, the large variety of developmental and environmental signals affecting cell division all converge on the regulation of CDK activity. CDKs can therefore be seen as the central engine driving cell division.

In animal systems and in yeast, knowledge about cell cycle regulations is now quite advanced. The activity of CDK-cyclin complexes is regulated at five levels: (i) transcription of the CDK and cyclin genes; (ii) association of specific CDK's with their specific cyclin partner; (iii) phosphorylation/dephosphorylation of the CDK and cyclins; (iv) interaction with other regulatory proteins such as SUC1/CKS1 homologues and cell cycle kinase inhibitors (CKI); and (v) cell cycle phase-dependent destruction of the cyclins and CKIs.

The study of cell cycle regulation in plants has lagged behind that in animals and yeast. Some basic mechanisms of cell cycle control appear to be conserved among eukaryotes, including plants. Plants were shown to also possess CDK's, cyclins and CKI's. However plants have unique developmental features which are reflected in specific characteristics of the cell cycle control. These include for instance the absence of cell migration, the formation of organs throughout the entire lifespan from specialized regions called meristems, the formation of a cell wall and the capacity of non-dividing cells to re-enter the cell cycle. Another specific feature is that many plant cells, in particular those involved in storage (e.g. endosperm), are polyploid due to rounds of DNA synthesis without mitosis. This so-called endoreduplication is intimately related with cell cycle control.

Due to these fundamental differences, multiple components of the cell cycle of plants are unique compared to their yeast and animal counterparts. For example, plants contain a unique class of CDKs, such as CDC2b in *Arabidopsis*, which are both structurally and functionally different from animal and yeast CDKs. The further elucidation of cell cycle regulation in plants and its differences and similarities with other eukaryotic systems is a major research challenge. Strictly for the case of comparison, some key elements about yeast and animal systems are described below in more detail.

As already mentioned above, the control of cell cycle progression in eukaryotes is mainly exerted at two transition points: one in late $G_1$, before DNA synthesis, and one at the $G_2$/M boundary. Progression through these control points is mediated by cyclin-dependent protein kinase (CDK) complexes, which contain, in more detail, a catalytic subunit of approximately 34-kDa encoded by the CDK genes. Both *Saccharomyces cerevisiae* and *Schizosaccharomyces pombe* only utilize one CDK gene for the regulation of their cell cycle. The kinase activity of their gene products $p34^{CDC2}$ and $p34^{CDC28}$ in *Sch. pombe* and in *S. cerevisiae*, respectively, is dependent on regulatory proteins, called cyclins. Progression through the different cell cycle phases is achieved by the sequential association of $p34^{CDC2/CDC28}$ with different cyclins. Although in higher eukaryotes this regulation mechanism is conserved, the situation is more complex since they have evolved to use multiple CDKs to regulate the different stages of the cell cycle. In mammals, seven CDKs have been described, defined as CDK1 to CDK7, each binding a specific subset of cyclins.

In animal systems, CDK activity is not only regulated by its association with cyclins but also involves both stimulatory and inhibitory phosphorylations. Kinase activity is positively regulated by phosphorylation of a Thr residue located between amino acids 160–170 (depending on the CDK protein). This phosphorylation is mediated by the CDK-activating kinase (CAK) which interestingly is a CDK/cyclin complex itself. Inhibitory phosphorylations occur at the ATP-binding site (the Tyr15 residue together with Thr14 in higher eukaryotes) and are carried out by at least two protein kinases. A specific phosphatase, CDC25, dephosphorylates these residues at the $G_2$/M checkpoint, thus activating CDK activity and resulting in the onset of mitosis. CDK activity is furthermore negatively regulated by a family of mainly low-molecular weight proteins, called cyclin-dependent kinase inhibitors (CKIs). Kinase activity is inhibited by the tight association of these CKIs with the CDK/cyclin complexes. CDK activity is furthermore negatively regulated by a family of mainly low-molecular weight proteins, called cyclin-dependent kinase inhibitors (CKIs). Kinase activity is inhibited by the tight association of these CKIs with the CDK/cyclin complexes. CKIs are produced during development when further cell division has to be prevented. In mammals CKIs have been shown to be involved in many different aspects of cell division and cell differentiation. First, CKI expression has been demonstrated to be induced under stress conditions such as for instance irradiation of cells or the influence of carcinogenic agents, which both potentially damage DNA. This arrest allows DNA to be repaired prior to DNA replication and mitosis. Second, inhibition of CDKs by CKIs has been demonstrated to correlate with cell differentiation and inhibition of programmed cell death. Third, the knock-out of certain members of the CKI family in mice results in an increase of body size and formation of tumors.

With respect to cell cycle regulation in plants a summary of the state of the art is given below. In *Arabidopsis*, thus far only two CDK genes have been isolated, CDC2aAt and CDC2bAt, of which the gene products share 56% amino acid identity. Both CDKs are distinguished by several features. First, only CDC2aAt is able to complement yeast $p34^{CDC2/CDC28}$ mutants. Second, CDC2aAt and CDC2bAt bear different cyclin-binding motifs (PSTAIRE and PPTALRE, respectively), suggesting they may bind distinct types of cyclins. Third, although both CDC2aAt and CDC2bAt show the same spatial expression pattern, they exhibit a different cell cycle phase-specific regulation. The CDC2aAt gene is expressed constitutively throughout the whole cell cycle. In contrast, CDC2bAt mRNA levels oscillate, being most abundant during the S and $G_2$ phases. In addition, multiple cyclins have been isolated from *Arabidopsis*. The majority displays the strongest sequence similarity with the animal A- or B-type class of cyclins, but also D-type cyclins have been identified. Although the classification of *Arabidopsis* cyclins is mainly based upon sequence similarity, limited data suggests that this organization corresponds with differential functions of each cyclin class. Recently, a CDK inhibitor has been identified in *Arabidopsis thaliana* (ICK1) that shares some limited similarity with the mammalian $p27^{kip1}$ kinase inhibitor (Wang, Nature 386 (1997), 451–452). This CDK inhibitor was predominantly identified when screening a library with a yeast two-hybrid "bait" construct harboring *Arabidopsis thaliana* CDC2aAt cDNA suggesting that only one class of CDK inhibitors is present in plants. However, the function and expression of CDK inhibitors in plants still needs to be determined.

In order to manage problems related to plant growth, plant architecture and/or plant diseases, it is believed to be of utmost importance to identify, isolate plant and characterize genes and gene products involved in the regulation of the plant cell division, and more particularly coding for and interacting with CDK's and/or their interacting proteins, responsible for the control of the cell cycle and the completion of the S and M phase of the cell cycle. If such novel genes and/or proteins have been isolated and analyzed, the growth of the plant as a whole can be influenced. Also, the growth of specific tissues or organs and thus the architecture of the plant can be modified.

Thus, the technical problem underlying the present invention is to provide means and methods for modulating cell cycle proteins that are particular useful in agriculture and plant cell and tissue culture.

BRIEF DESCRIPTION OF THE DRAWINGS

FIG. 1 shows the sequence alignment of the *Arabidopsis thaliana* cyclin-dependent kinase inhibitors FL39, FL66, FL67, ICKI (accession number AC003040); the *Medicago sativa* cyclin-dependent kinase inhibitor ALFCDKI, and the *Chenopodium rubrum* cyclin-dependent kinase CrCKI (accession number AJ002173). Alignment was obtained using the PILEUP program (from the GCG 9.1 package) using the parameters Gap weight=4 and Length weight=0.

FIGS. 2B–2F show ICK 2 expression in radish seedlings visualized by in situ hydridization.

2(B) Occasional ICK2 mRNA accumulation in individual cells of the L1 layer of the shoot apical meristem (SAM).

2(C) ICK2 mRNA accumulation in abaxial (Ab) and adaxial (Ad) epidermal layers of a leaf primordium (LP).

2(D) ICK2 mRNA accumulation in abaxial (Ab) and adaxial (Ad) epidermal layers of a young leaf (YL).

2(E) and (F) Patchy ICK2 mRNA accumulation pattern in abaxial (Ab) and adaxial (Ad) epidermal layers of maturing leaves.

Figure 3A:
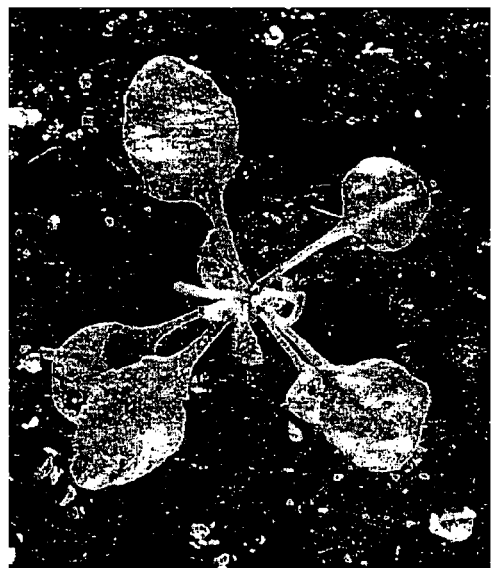

FIG. 3A is a top view of an *Arabidopsis thaliana* Col-O control plant.

Figure 3B:

FIG. 3B is a top view of a transgenic *A. thaliana* plant constitutively expressing ICK2.

Figure 3C:
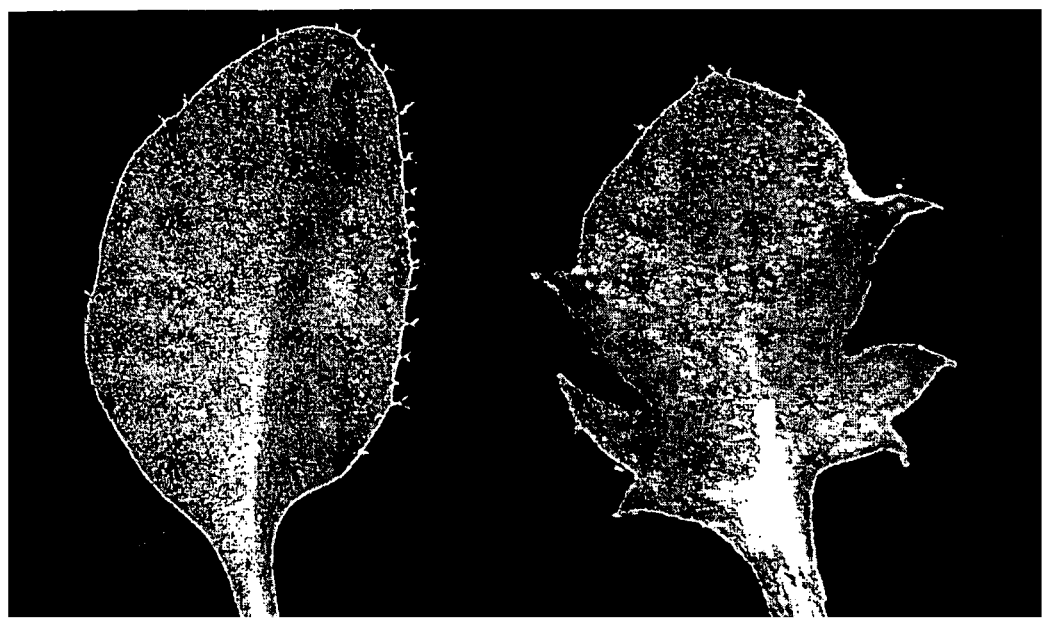

FIG. 3C shows a magnification of a leaf of a *A. thaliana* Col-O control plant (left) and of a leaf of a plant of the transgenic *A. thaliana* line ICK2 1.10 constitutively expressing ICK2 (right).

FIG. 4A shows the shape and venation pattern of the $5^{th}$ rosette leaf of an *Arabidopsis thaliana* Col-O control plant.

FIG. 4B shows the shape and venation pattern in the $5^{th}$ rosette leaf of a plant of the transgenic *A. thaliana* line ICK 2 1.10 constitutively expressing ICK2.

Figure 5:
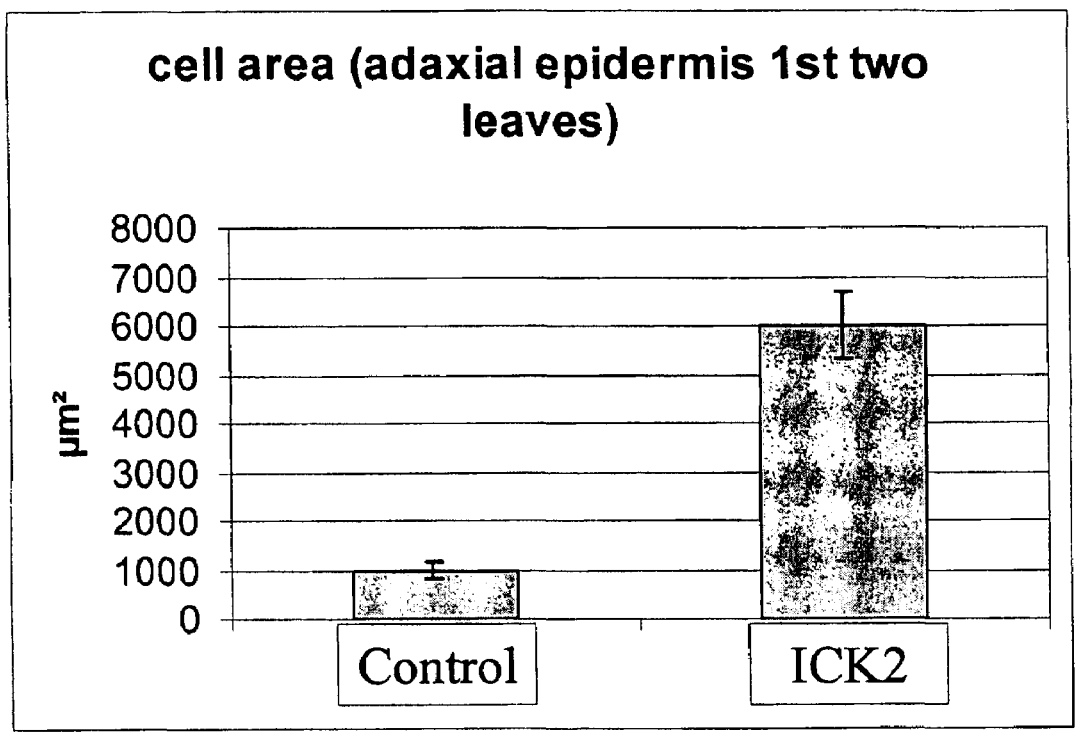

FIG. 5 graphically depicts average area of cells from control and ICK2 expressing plants. The area was determined of cells in the adaxial epidermal layer of the $1^{st}$ two leaves of a *A. thaliana* Col-O control plant and of a leaf of a plant of the transgenic *A. thaliana* line ICK2.1.10 constitutively expressing ICK2.

Figures 6A, 6B:
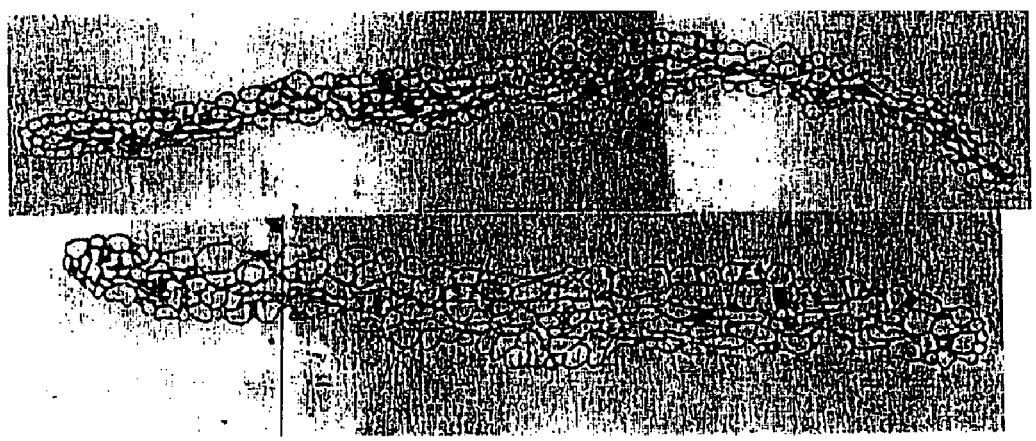

FIG. 6A is a cross section through the central part of a leaf from an *A. thaliana* Col-O control plant.

FIG. 6B is a cross section through the central part of a leaf from transgenic *A. thaliana* plant constitutively expressing ICK2.

FIGS. 7A–7H are photomicrographs of wild type and experimental plants. The larger cells in leaves of tgransgenic plants are clearly visible as a, jigsaw in epidermal cell layers (B and H) and as large irregular circles in palissade (D) and spongy parenchyma (F) cells. The much smaller cells in leaves of control plants are visible as small irregular circles (A, C, E, and G).

7(A) Image of the adaxial epidermis of leaf of an *A. thaliana* Col-O control plant.

7(B) Image of the adaxial epidermis of a leaf of a transgenic *A. thaliana* plant constitutively expressing ICK2.

7(C) Image of the palissade layer of a leaf of an *A. thaliana* Col-O control plant.

7(D) Image of the palissade layer of a leaf of a transgenic *A. thaliana* plant constitutively expressing ICK2.

7(E) Image of the spongy parenchyma of a leaf of an *A. thaliana* Col-O control plant.

7(F) Image of the spongy parenchyma of a transgenic *A. thaliana* plant constitutively expressing ICK2.

7(G) Image of the abaxial epidermis of a leaf of an *A. thaliana* Col-O control plant.

7(H) Image of the abaxial epidermis of a leaf of a transgenic *A. thaliana* plant constitutively expressing ICK2.

Figure 8A:
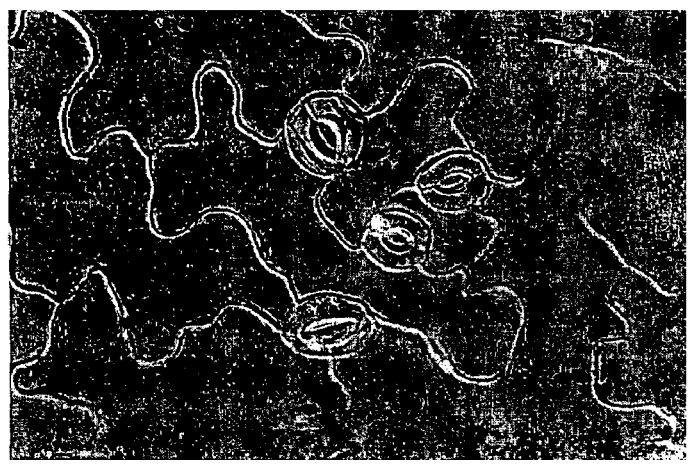

FIG. 8A is a photomicrograph of stomata in abaxial epidermis of a leaf of an *A. thaliana* Col-O control plant.

Figure 8B:

FIG. 8B is a photomicrograph of stomata in the abaxial epidermis of a leaf of a transgenic *A. thaliana* plant constitutively expressing ICK2.

Figure 9A:
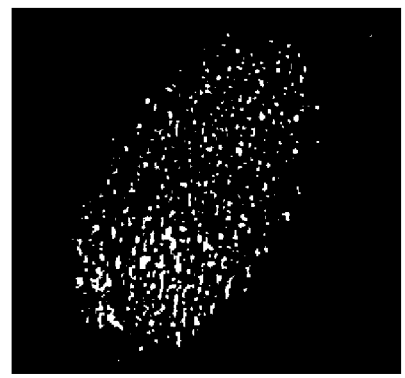

FIG. 9A is a photograph of a typical seed of an *A. thaliana* Col-O control plant.

Figure 9B:
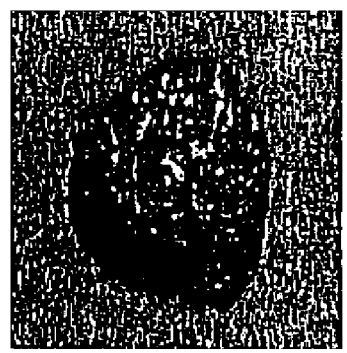

FIG. 9B is a photograph of a typical seed of a transgenic *A. thaliana* plant constitutively expressing ICK 2. Seeds are smaller and have a different shape as compared to seeds of a control plant.

Figure 10:
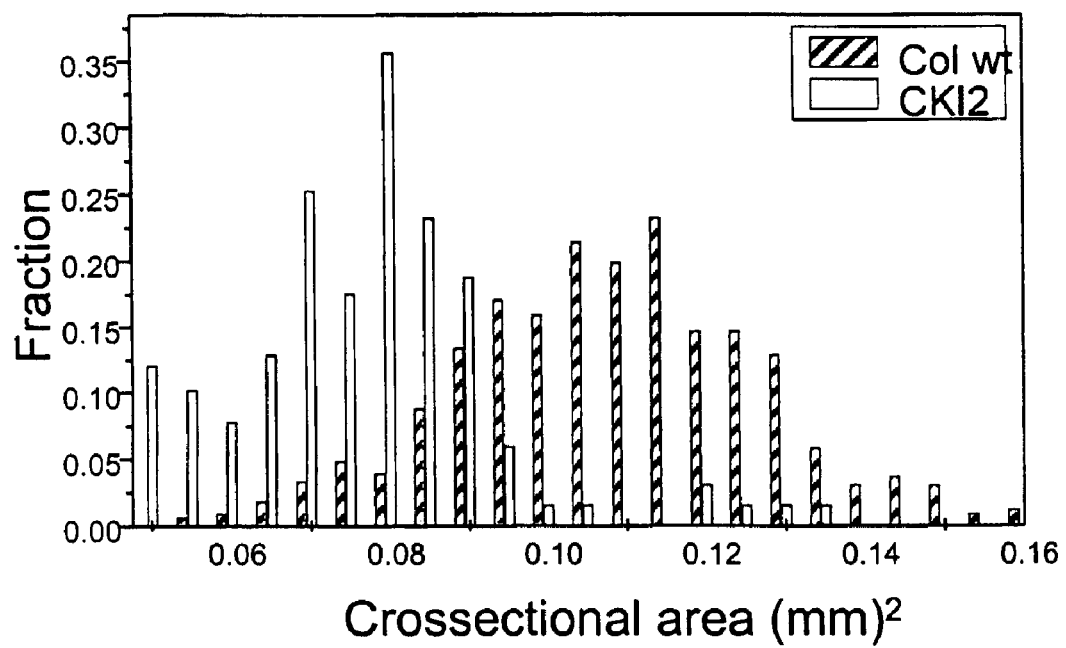

FIG. 10 graphically depicts seed size distribution in control and experimental plants. The average crpss sectional area of seeds of *A. thaliana* Col-O control plants (open bars) was $0.11\pm0.04$ mm². The average cross sectional area of seeds of transgenic *A. thaliana* plants constitutively expressing ICK2 (hatched bars) was $0.08\pm0.01$ mm².

Figure 11:
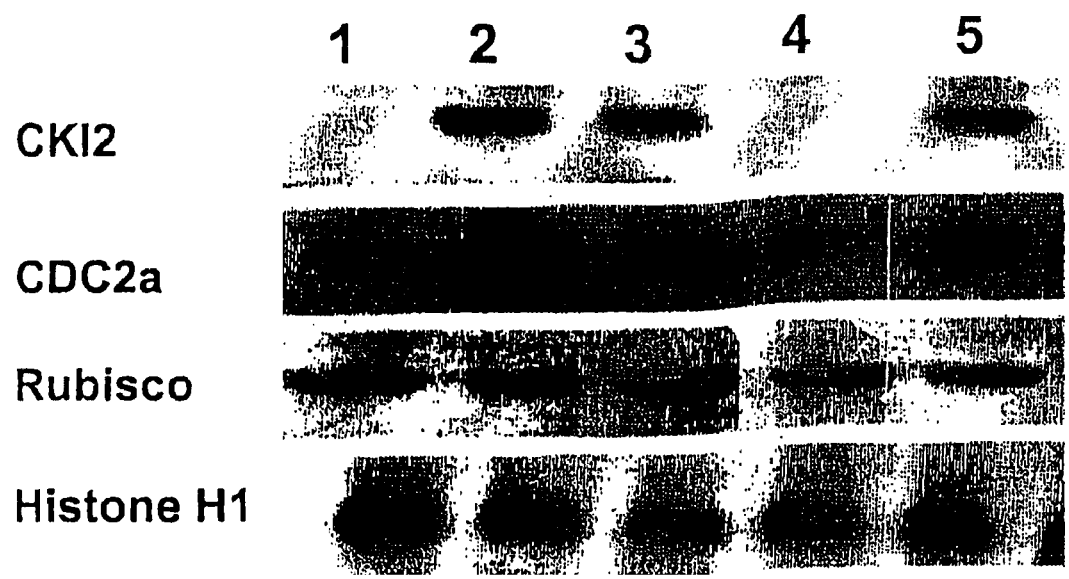

FIG. 11 is a Western blot showing CKI2, CDC2aAt and Rubisco protein levels and CDK kinase activity. Total soluble protein was extracted from leaves of one wild-type Col-O line (lane 1) and four independent CKI2 transgenic lines (lanes 2 through 5). Protein samples were analyzed by Western blotting for the visualization of CKI2 protein and CDC2aAt protein. Rubisco was used as a marker for equal protein loading. CDK kinase activity was measured using $p10^{cks1At}$ Sepharose beads and Histone H1 as substrate.

Figure 12:
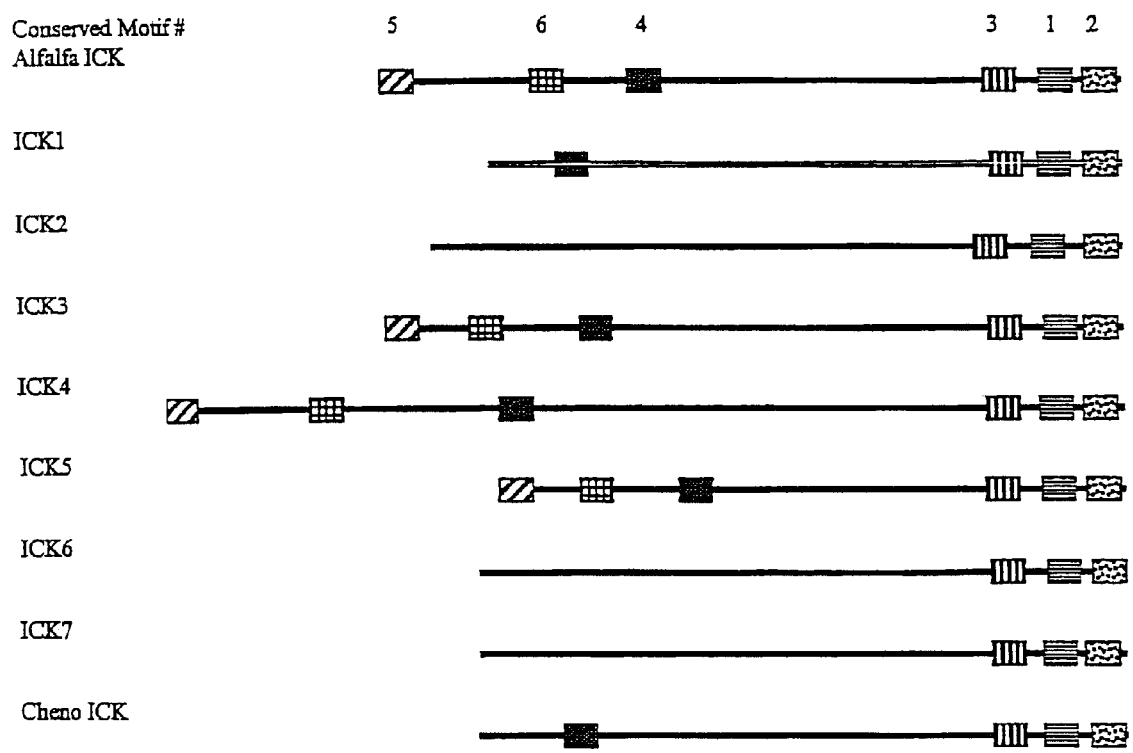

FIG. 12 schematically shows the occurrence and positioning of conserved motifs in plant ICKs. The amino acid sequences of motifs 1–6 are set forth in Table 2. ICK1 through ICK 7 represent the seven known *A. thaliana* —ICKs, ICK1 was previously known as LDV5; ICK2 as LDV39 and FL39; ICK3 as FL66; ICK4 as FL67; ICK6 as ICN2 (Wang et al. 99-WO9964599) and ICK7 as ICN6 (Want et al. 99-WO9964599. ICK5 has GenBank accession umber AP000419 and is annotated as ICK. Cheno ICK: *Chenopodium rubrum* ICK.

DETAILED DESCRIPTION OF THE INVENTION

The present invention relates to a DNA sequence encoding a cyclin-dependent kinase inhibitor or encoding an immunologically active and/or functional fragment of such a protein, selected from the group consisting of:

(a) DNA sequences comprising a nucleotide sequence encoding protein comprising the amino acid sequence as given in SEQ ID NO: 2, 4 or 6;

(b) DNA sequences comprising a nucleotide sequence as given in SEQ D NO: 1, 3 or 5;

(c) DNA sequences comprising the nucleotide sequence encoding a protein comprising the amino acid sequence from amino acid position 75 to 209 of SEQ ID NO: 2 or from amino acid position 11 to 216 of SEQ ID NO: 4 or comprising the nucleotide sequence from nucleotide position 305 to 932 of SEQ ID NO: 1;

(d) DNA sequences hybridizing with the complementary strand of a DNA sequence as defined in any one of (a) to (c);

(e) DNA sequences encoding an amino acid sequence which is at least 30% identical to the amino acid sequence encoded by the DNA sequence of any one of (a) to (c);

(f) DNA sequences, the nucleotide sequence of which is degenerated as a result of the genetic code to a nucleotide sequence of a DNA sequence as defined in any one of (a) to (e); and (g) DNA sequences encoding a fragment of a protein encoded by a DNA sequence of any one of (a) to (f).

The term "cyclin-dependent kinase inhibitor" also designated CDK inhibitor, CKI or CDKI as denoted herein means a protein which inhibits CDK/cyclin activity and is produced during development when further cell division has to be prevented. A CDK inhibitor of the invention is capable of inhibiting or suppressing the kinase activity of protein kinases, in particular of cyclin-dependent kinases. The capability of a inhibiting or suppressing protein kinase activity can be determined according to methods well known in the art; see, e.g., Wang, supra and the appended examples.

The term "cell cycle" means the cyclic biochemical and structural events associated with growth of cells, and in particular with the regulation of the replication of DNA and mitosis. The cycle is divided into periods called: $G_0$, $Gap_1$ ($G_1$), DNA synthesis (S), $Gap_2$ ($G_2$), and mitosis (M).

The terms "gene(s)", "polynucleotide", "nucleic acid sequence", "nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog. Preferably, the DNA sequence of the invention comprises a coding sequence encoding the above defined cell cycle interacting protein.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

In accordance with the present invention new plant gene products with a putative CDK inhibitory function were screened by using the two-hybrid system (Fields, Nature 340 (1989), 245–246). For this purpose the CDC2aAt protein was exploited as bait. Previous attempts using the identical bait and a cDNA library constructed with RNA from 3-week-old *Arabidopsis thaliana* vegetative tissues were unsuccessful (De Veylder, Febs Lett. 412 (1997), 446–452;

De Veylder, J. Exp. Bot. 48 (1997), 2113–2114). A new attempt was undertaken using a newly constructed library made from a RNA mixture of *Arabidopsis thaliana* cell suspensions harvested at various growing stages: early exponential, exponential, early stationary and stationary phase. This library has the advantage above the previous one to include mainly genes expressed in cells at the onset of cell division, actively dividing cells, cells redrawing from the cell cycle, and non-cycling cells. Surprisingly, using this specific library several positive clones were identified encoding proteins with a putative CDK inhibitory function. These clones were designated LDV39, LDV66, and LDV1 59.

A homology search in databases revealed that the last 23 amino-acids showed significant homology to the human CKIs p21$^{cip1}$ and p27$^{kip1}$. The LDV39 gene was 622 bp long, consisting of 423 bp coding region and 199 bp 3' UTR (excluding the poly-A tail). The LDV66 gene was 611 bp long, consisting of 379 bp coding region and 232 bp 3' UTR (excluding the poly-A tail). Since the LDV39 and LDV66 clones encode partial proteins, lacking their amino-terminal part, a flower cDNA library obtained from the ABRC stock centre (library stock number CD4-6) was screened. The positive clones were denominated FL39 and FL66, corresponding to longer clones of LDV39 and LDV66, respectively.

The FL39 clone is 932 bp (SEQ ID NO:1) long and contains an ORF encoding a protein of 209 amino acids (SEQ ID NO:2) with a calculated molecular mass of 24 kDa. In its 3' UTR a polyadenylation signal can be recognized. The amino-terminal part of the FL39 protein contains a repeated motif of 11 amino acids VRRRD/ExxxVEE, (SEQ ID NO:33). This motif is not found in any other protein in the databanks and its significance is unknown. The FL39 protein also contains a putative nuclear localization signal (amino acids 23–26) and a PEST-rich region (amino acids 71–98; PESTFIND score +15.5) These sequences, rich in proline, glutamic acid, serine and proline, are characteristically present in ustable proteins (Rogers et al., 1986, Science 234, 364–368).

The FL66 sequence does not contain an in frame stopcodon, and may therefore not be full length. The FL66 clone is 875 bp long (SEQ ID NO: 3) and bears an ORF of 216 amino acids (SEQ ID NO: 4), encoding a protein of 24 kD. No nuclear localization signal or PEST domains are present. Furthermore, a CDK inhibitor named ALFCDKI from alfalfa has been identified in accordance with the present invention using a two-hybrid screening assay. This gene comprises 1202 nucleotides (SEQ ID NO:5) with a coding region from nucleotide position 94 to 760 encoding a protein of 224 amino acids (SEQ ID NO:6). The LDV159 clone was identical to ICK1 (GenBank accession number U94772 as published by Wang, Nature 386 (1997), p451–452). Surprisingly, the three other clones were novel and encoded proteins only distantly related to ICK1 (Table 1).

TABLE 1

Sequence similarity and identity between the different plant cyclin-dependent kinase inhibitors. CrCKI is the *Chenopodium rubrum* CKI (accession number AJ00217).

|  | FL39 | FL66 | FL67 | ICK1 | CrCKI | ALFCDKI |
|---|---|---|---|---|---|---|
| FL39 |  | 27.805 | 33.333 | 32.292 | 34.392 | N.S. |
| FL66 | 21.463 |  | 39.545 | 37.017 | 34.574 | 34.389 |
| FL67 | 20.000 | 30.909 |  | 30.220 | N.S. | N.S. |
| ICK | 23.958 | 30.939 | 22.527 |  | 32.105 | 25.131 |

TABLE 1-continued

Sequence similarity and identity between the different plant cyclin-dependent kinase inhibitors. CrCKI is the *Chenopodium rubrum* CKI (accession number AJ00217).

|  | FL39 | FL66 | FL67 | ICK1 | CrCKI | ALFCDKI |
|---|---|---|---|---|---|---|
| CrCKI | 24.868 | 28.723 | N.S. | 27.368 |  | 26.667 |
| MsCKI | N.S. | 28.054 | N.S. | 21.990 | 20.513 |  |

The percentage similarity (bold) and identity (italic) between the different Cyclin-dependent kinase inhibitors was determined using the GAP program (from the GCG 9.1 package) using the parameters Gap weight = 12 and Length weight = 4.
N.S.: Not Significant.

Furthermore, the genomic organisation of the FL39, FL66 and ICK1 clones was tested by DNA gel blot analysis. The results of the experiments suggest the presence of an additional FL66 related gene and, therefore, it can be concluded that there are at least four different CKI proteins present in *A. thaliana*. From the foregoing it is evident that more than one CDK inhibitor in plants exist and therefore different functions during plant development and/or expression patterns can be assumed. Further studies that have been performed in accordance with the present invention revealed that the CDK inhibitors are expressed at different time points during the cultivation of the plant cell culture; see Example 8. Moreover, it could be demonstrated in accordance with the present invention that the CDK inhibitor FL66 is regulated by NaCl; see Example 9. The inhibitory function of the CDK inhibitor of the invention is exemplified with FL66; see Example 6. In addition, in situ hybridization using antisense probes derived from cDNAs from LDV39, LDV66 and LDV159 demonstrated that each of these CDK inhibitors exhibit distinct expression patterns; see Example 13. Thus, the findings of the present invention establishes that in plants several CDK inhibitors exist which due to their differential expression pattern may have different functions during the development of the plant. It can be expected that similar gene families encoding CDK inhibitors are present in other plant species than *Arabidopsis* and alfalfa as well. These cyclin-dependent inhibitors are also within the scope of the present invention.

Accordingly, the present invention also relates to nucleic acid molecules hybridizing with the above-described nucleic acid molecules and differ in one or more positions in comparison with these as long as they encode a cyclin-dependent kinase inhibitor. By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)). Preferably, the hybridization conditions used in the examples are employed. Cyclin-dependent kinase inhibitor derived from other organisms such as mammals, in particular humans, may be encoded by other DNA sequences which hybridize to the sequences for plant cyclin-dependent kinase inhibitor under relaxed hybridization conditions and which code on expression for peptides having the ability to interact with cell cycle proteins. Examples of such non-stringent hybridization conditions are 4×SSC at 50° C. or hybridization with 30–40% formamide at 42° C. Such molecules comprise those which are fragments, analogues or derivatives of the cell cycle interacting protein of the invention and differ, for example, by way of amino acid and/or nucleotide deletion(s), insertion(s), substitution(s), addition(s) and/or recombination(s) or any other modification(s) known in the art either alone or in combination from the above-described amino acid sequences or their underlying nucleotide sequence(s). Methods for introducing such modifications in the nucleic acid molecules according to the invention are well-known to the person skilled in the art. The invention also relates to nucleic acid molecules the sequence of which differs from the nucleotide sequence of any of the above-described nucleic acid molecules due to the degeneracy of the genetic code. All such fragments, analogues and derivatives of the protein of the invention are included within the scope of the present invention, as long as the essential characteristic immunological and/or biological properties as defined above remain unaffected in kind, that is the novel nucleic acid molecules of the invention include all nucleotide sequences encoding proteins or peptides which have at least a part of the primary structural conformation for one or more epitopes capable of reacting with antibodies to cyclin-dependent kinase inhibitor which are encodable by a nucleic acid molecule as set forth above and which have comparable or identical characteristics in terms of inhibiting cyclin dependent kinases, in particular plant cyclin dependent kinases. Part of the invention are therefore also nucleic acid molecules encoding a polypeptide comprising at least a functional part of cyclin-dependent kinase inhibitor encoded by a nucleic acid sequence comprised in a nucleic acid molecule according to the invention. An example for this is that the polypeptide or a fragment thereof according to the invention is embedded in another amino acid sequence.

As is demonstrated in the appended examples a two-hybrid screening assay has been developed in accordance with the present invention suitable for identifying cyclin-dependent kinase inhibitor. Thus, in another aspect the present invention relates to a method for identifying and obtaining cyclin-dependent kinase inhibitors comprising a two-hybrid screening assay wherein CDC2a as a bait and a cDNA library of cell suspension as prey are used. Preferably, said CDC2a is CDC2aAt. However, CDC2a from other organisms such as other plants but also mammals may be employed as well.

The nucleic acid molecules encoding proteins or peptides identified to interact with the CDC2a in the above mentioned assay can be easily obtained and sequenced by methods known in the art; see also the appended examples. Therefore, the present invention also relates to a DNA sequence encoding a cyclin-dependent kinase inhibitor obtainable by the method of the invention. Preferably, the amino acid sequence of said protein obtainable by the method of the invention has an identity to the amino acid sequence of any one of SEQ ID NOS: 2, 4 or 6 of at least 30%, more preferably 40 to 60% and most preferably 70% to 90%.

In a preferred embodiment the nucleic acid molecules according to the invention are RNA or DNA molecules, preferably cDNA, genomic DNA or synthetically synthesized DNA or RNA molecules. Preferably, the nucleic acid molecule of the invention is derived from a plant, preferably from *Arabidopsis thaliana*. As discussed above, a cyclin-dependent kinase inhibitor could also be identified in *Medicago sativa* (Alfalfa). Corresponding proteins displaying similar properties should, therefore, be present in other plants as well. Nucleic acid molecules of the invention can be obtained, e.g., by hybridization of the above-described nucleic acid molecules with a (sample of) nucleic acid molecule(s) of any source. Nucleic acid molecules hybridizing with the above-described nucleic acid molecules can in general be derived from any organism, preferably plant possessing such molecules, preferably form monocotyledonous or dicotyledonous plants, in particular from any organism, preferably plants of interest in agriculture, horticulture or wood culture, such as crop plants, namely those of the family Poaceae, any starch producing plants, such as potato, maniok, leguminous plants, oil producing plants, such as oilseed rape, linenseed, etc., plants using polypeptide as storage substances, such as soybean, plants using sucrose as storage substance, such as sugar beet or sugar cane, trees, ornamental plants etc. Preferably, the nucleic acid molecules according to the invention are derived from *Arabidopsis thaliana*. Nucleic acid molecules hybridizing to the above-described nucleic acid molecules can be isolated, e.g., form libraries, such as cDNA or genomic libraries by techniques well known in the art. For example, hybridizing nucleic acid molecules can be identified and isolated by using the above-described nucleic acid molecules or fragments thereof or complements thereof as probes to screen libraries by hybridizing with said molecules according to standard techniques. Possible is also the isolation of such nucleic acid molecules by applying the polymerase chain reaction (PCR) using as primers oligonucleotides derived form the above-described nucleic acid molecules.

Nucleic acid molecules which hybridize with any of the aforementioned nucleic acid molecules also include fragments, derivatives and allelic variants of the above-described nucleic acid molecules that encode a cyclin-dependent kinase inhibitor or an immunologically or functional fragment thereof. Fragments are understood to be parts of nucleic acid molecules long enough to encode the described protein or a functional or immunologically active fragment thereof as defined above. Preferably, the functional fragment contains a motif of 11 amino acids (VRRRD/ExxxVEE; SEQ ID NO: 33) present in the amino terminal part of the FL39 protein. This motif is not found in any other protein in the databanks and its significance in unknown. Furthermore, the fragment may contain the putative nuclear localization signal (amino acids 23–26 of SEQ ID NO: 2) and/or the PEST-rich region (amino acids 71–98 of SEQ ID NO: 2; see also Example 3).

The term "derivative" means in this context that the nucleotide sequence of these nucleic acid molecules differs from the sequences of the above-described nucleic acid molecules in one or more nucleotide positions and are highly homologous to said nucleic acid molecules. Homology is understood to refer to a sequence identity of at least 30%, particularly an identity of at least 60%, preferably more than 80% and still more preferably more than 90%. The term "substantially homologous" refers to a subject, for instance a nucleic acid, which is at least 50% identical in sequence to the reference when the entire ORF (open reading frame) is compared, where the sequence identity is preferably at least 70%, more preferably at least 80%, still more preferably at least 85%, especially more than about 90%, most preferably 95% or greater, particularly 98% or greater. The deviations from the sequences of the nucleic acid molecules described above can, for example, be the result of nucleotide substitution(s), deletion(s), addition(s), insertion(s) and/or recombination(s); see supra.

Homology further means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants; see supra.

The proteins encoded by the various derivatives and variants of the above-described nucleic acid molecules share specific common characteristics, such as biological activity, molecular weight, immunological reactivity, conformation, etc., as well as physical properties, such as electrophoretic mobility, chromatographic behavior, sedimentation coefficients, pH optimum, temperature optimum, stability, solubility, spectroscopic properties, etc.

Examples of the different possible applications of the nucleic acid molecules according to the invention as well as molecules derived from them will be described in detail in the following.

Hence, in a further embodiment, the invention relates to nucleic acid molecules of at least 15 nucleotides in length hybridizing specifically with a nucleic acid molecule as described above or with a complementary strand thereof. Specific hybridization occurs preferably under stringent conditions and implies no or very little cross-hybridization with nucleotide sequences encoding no or substantially different proteins. Such nucleic acid molecules may be used as probes and/or for the control of gene expression. Nucleic acid probe technology is well known to those skilled in the art who will readily appreciate that such probes may vary in length. Preferred are nucleic acid probes of 16 to 35 nucleotides in length. Of course, it may also be appropriate to use nucleic acids of up to 100 and more nucleotides in length. The nucleic acid probes of the invention are useful for various applications. On the one hand, they may be used as PCR primers for amplification of nucleic acid sequences according to the invention. The design and use of said primers is known by the person skilled in the art. Preferably such amplification primers comprise a contiguous sequence of at least 6 nucleotides, in particular 13 nucleotides, preferably 15 to 25 nucleotides or more, identical or complementary to the nucleotide sequence depicted in SEQ ID NO: 1, 3 or 5 or to a nucleotide sequence encoding the amino acid sequence of SEQ ID NO: 2, 4 or 6. Another application is the use as a hybridization probe to identify nucleic acid molecules hybridizing with a nucleic acid molecule of the invention by homology screening of genomic DNA or cDNA libraries. Nucleic acid molecules according to this preferred embodiment of the invention which are complementary to a nucleic acid molecule as described above may also be used for repression of expression of a CKI encoding gene, for example due to an antisense or triple helix effect or for the construction of appropriate ribozymes (see, e.g., EP-A1 0 291 533, EP-A1 0 321 201, EP-A2 0 360 257) which specifically cleave the (pre)-mRNA of a gene comprising a nucleic acid molecule of the invention or part thereof. Selection of appropriate target sites and corresponding ribozymes can be done as described, for example, in Steinecke, Ribozymes, Methods in Cell Biology 50, Galbraith et al. eds Academic Press, Inc. (1995), 449–460. In this aspect of the invention, a method of downregulating expression of a CKI in a plant comprises introducing into a plant cell a ribozyme targeted to a CKI transcript in the plant cell. Furthermore, the person skilled in the art is well aware that it is also possible to label such a nucleic acid probe with an appropriate marker for specific applications, such as for the detection of the presence of a nucleic acid molecule of the invention in a sample derived from an organism, in particular plants.

The above described nucleic acid molecules may either be DNA or RNA or a hybrid thereof. Furthermore, said nucleic acid molecule may contain, for example, thioester bonds and/or nucleotide analogues, commonly used in oligonucleotide anti-sense approaches. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell.

Furthermore, the so-called "peptide nucleic acid" (PNA) technique can be used for the detection or inhibition of the expression of a nucleic acid molecule of the invention. For example, the binding of PNAs to complementary as well as various single stranded RNA and DNA nucleic acid molecules can be systematically investigated using thermal denaturation and BIAcore surface-interaction techniques (Jensen, Biochemistry 36 (1997), 5072–5077). Furthermore, the nucleic acid molecules described above as well as PNAs derived therefrom can be used for detecting point mutations by hybridization with nucleic acids obtained from a sample with an affinity sensor, such as BIAcore; see Gotoh, Rinsho Byori 45 (1997), 224–228. Hybridization based DNA screening on peptide nucleic acids (PNA) oligomer arrays are described in the prior art, for example in Weiler, Nucleic Acids Research 25 (1997), 2792–2799. The synthesis of PNAs can be performed according to methods known in the art, for example, as described in Koch, J. Pept. Res. 49 (1997), 80–88; Finn, Nucleic Acids Research 24 (1996), 3357–3363. Further possible applications of such PNAs, for example as restriction enzymes or as templates for the synthesis of nucleic acid oligonucleotides are known to the person skilled in the art and are, for example, described in Veselkov, Nature 379 (1996), 214 and Bohler, Nature 376 (1995), 578–581.

The present invention also relates to vectors, particularly plasmids, cosmids, viruses, bacteriophages and other vectors used conventionally in genetic engineering that contain a nucleic acid molecule according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the nucleic acid molecules and vectors of the invention can be reconstituted into liposomes for delivery to target cells.

In a preferred embodiment the nucleic acid molecule present in the vector is linked to (a) control sequence(s) which allow the expression of the nucleic acid molecule in prokaryotic and/or eukaryotic cells.

The term "control sequence" refers to regulatory DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

Thus, the vector of the invention is preferably an expression vector. An "expression vector" is a construct that can be used to transform a selected host cell and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotic and/or eukaryotic cells are well known to those skilled in the art. In the case of eukaryotic cells they comprise normally promoters ensuring initiation of transcription and optionally poly-A signals ensuring termination of transcription and stabilization of the transcript, for example, those of the 35S RNA from Cauliflower Mosaic Virus (CaMV). Other promoters commonly used are the polyubiquitin promoter, and the actin promoter for ubiquitous expression. The termination signals usually employed are from the Nopaline Synthase promoter or from the CAMV 35S promoter. A plant translational enhancer often used is the CAMV omega sequences, the inclusion of an intron (Intron-1 from the Shrunken gene of maize, for example) has been shown to increase expression levels by up to 100-fold. (Mait, Transgenic Research 6 (1997), 143–156; Ni, Plant Journal 7 (1995), 661–676). Additional regulatory elements may include transcriptional as well as translational enhancers. Possible regulatory elements permitting expression in prokaryotic host cells comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Advantageously, the above-described vectors of the invention comprises a selectable and/or scorable marker. Selectable marker genes useful for the selection of transformed plant cells, callus, plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143–149); npt, which confers resistance to the aminoglycosides neomycin, kanamycin and paromycin (Herrera-Estrella, EMBO J. 2 (1983), 987–995) and hygro, which confers resistance to hygromycin (Marsh, Gene 32 (1984), 481–485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336–2338).

Useful scorable marker are also known to those skilled in the art and are commercially available. Advantageously, said marker is a gene encoding luciferase (Giacomin, Pl. Sci. 116 (1996), 59–72; Scikantha, J. Bact. 178 (1996), 121), green fluorescent protein (Gerdes, FEBS Lett. 389 (1996), 44–47) or βglucuronidase (Jefferson, EMBO J. 6 (1987), 3901–3907). This embodiment is particularly useful for simple and rapid screening of cells, tissues and organisms containing a vector of the invention.

The present invention furthermore relates to host cells comprising a vector as described above or a nucleic acid molecule according to the invention wherein the nucleic acid molecule is foreign to the host cell.

By "foreign" it is meant that the nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination (Paszkowski (ed.), Homologous Recombination and Gene Silencing in Plants. Kluwer Academic Publishers (1994)).

The host cell can be any prokaryotic or eukaryotic cell, such as bacterial, insect, fungal, plant or animal cells. Preferred fungal cells are, for example, those of the genus *Saccharomyces*, in particular those of the species *S. cerevisiae*.

Another subject of the invention is a method for the preparation of a cyclin-dependent kinase inhibitor which comprises the cultivation of host cells according to the invention which, due to the presence of a vector or a nucleic acid molecule according to the invention, are able to express such a protein, under conditions which allow expression of the protein and recovering of the so-produced protein from the culture.

The term "expression" means the production of a protein or nucleotide sequence in the cell. However, said term also includes expression of the protein in a cell-free system. It includes transcription into an RNA product, post-transcriptional modification and/or translation to a protein product or polypeptide from a DNA encoding that product, as well as possible post-translational modifications. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesized and/or modified according to standard methods described, for example hereinbelow.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The present invention furthermore relates to CKIs encoded by the nucleic acid molecules according to the invention or produced or obtained by the above-described methods, and to functional and/or immunologically active fragments of such cyclin-dependent kinase inhibitor. The proteins and polypeptides of the present invention are not necessarily translated from a designated nucleic acid sequence; the polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art. In this context, it is also understood that the proteins according to the invention may be further modified by conventional methods known in the art. By providing the proteins according to the present invention it is also possible to determine fragments which retain biological activity, for example, the mature, processed form. This allows the construction of chimeric proteins and peptides comprising an amino sequence derived from the protein of the invention, which is crucial for its binding activity and other functional amino acid sequences, e.g. GUS marker gene (Jefferson, EMBO J. 6 (1987), 3901–3907). The other functional amino acid sequences may be either physically linked by, e.g., chemical means to the proteins of the invention or may be fused by recombinant DNA techniques well known in the art.

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids. Preferably, the polypeptides according to the invention comprising the amino acid sequence as defined above and/or a fragment thereof have a molecular weight of approximately 15–20 kDa.

Furthermore, folding simulations and computer redesign of structural motifs of the protein of the invention can be performed using appropriate computer programs (Olszewski, Proteins 25 (1996), 286–299; Hoffman, Comput. Appl. Biosci. 11 (1995), 675–679). Computer modeling of protein folding can be used for the conformational and energetic analysis of detailed peptide and protein models (Monge, J. Mol. Biol. 247 (1995), 995–1012; Renouf, Adv. Exp. Med. Biol. 376 (1995), 37–45). In particular, the appropriate programs can be used for the identification of interactive sites of the CKI and cyclin dependent kinases, its ligand or other interacting proteins by computer assistant searches for complementary peptide sequences (Fassina, Immunomethods 5 (1994), 114–120). Further appropriate computer systems for the design of protein and peptides are described in the prior art, for example in Berry, Biochem. Soc. Trans. 22 (1994), 1033–1036; Wodak, Ann. N.Y. Acad. Sci. 501 (1987), 1–13; Pabo, Biochemistry 25 (1986), 5987–5991. The results obtained from the above-described computer analysis can be used for, e.g., the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218–33224). For example, incorporation of easily available achiral Ω-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769–777). Superactive peptidomimetic analogues of small peptide hormones in other systems are described in the prior art (Zhang, Biochem. Biophys. Res. Commun. 224 (1996), 327–331). Appropriate peptidomimetics of the protein of the present invention can also be identified by the synthesis of peptidomimetic combinatorial libraries through successive amide alkylation and testing the resulting compounds, e.g., for their binding, kinase inhibitory and/or immunological properties. Methods for the generation and use of peptidomimetic combinatorial libraries are described in the prior art, for example in Ostresh, Methods in Enzymology 267 (1996), 220–234 and Dorner, Bioorg. Med. Chem. 4 (1996), 709–715.

Furthermore, a three-dimensional and/or crystallographic structure of the protein of the invention can be used for the design of peptidomimetic inhibitors of the biological activity of the protein of the invention (Rose, Biochemistry 35 (1996), 12933–12944; Rutenber, Bioorg. Med. Chem. 4 (1996), 1545–1558).

Furthermore, the present invention relates to antibodies specifically recognizing a cyclin-dependent kinase inhibitor according to the invention or parts, i.e. specific fragments or epitopes, of such a protein. The antibodies of the invention can be used to identify and isolate other cyclin-dependent kinase inhibitors and genes in any organism, preferably plants. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988.

These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97–105; Malmborg, J. Immunol. Methods 183 (1995), 7–13). In many cases, the binding phenomena of antibodies to antigens is equivalent to other ligand/anti-ligand binding.

Plant cell division can conceptually be influenced in three ways: (i) inhibiting or arresting cell division, (ii) maintaining, facilitating or stimulating cell division or (iii) uncoupling DNA synthesis from mitosis and cytokinesis. Modulation of the expression of a polypeptide encoded by a nucleotide sequence according to the invention has surprisingly an advantageous influence on plant cell division characteristics, in particular on the disruption of the expression levels of genes or the biological activity of the proteins involved in G1/S and/or G2/M transition and as a result therof on the total make-up of the plant concerned or parts thereof. An example is that DNA synthesis or progression of DNA replication will be negatively influenced by inactivating or inhibiting cyclin-dependent protein kinase complexes.

The term "cyclin-dependent protein kinase complex" means the complex formed when a, preferably functional, cyclin associates with a, preferably, functional cyclin dependent kinase. Such complexes may be active in phosphorylating proteins and may or may not contain additional protein species. The activity of a CDK in a plant cell is influenced by manipulation of the gene according to the invention. To analyse the industrial applicabilities of the invention, transformed plants can be made overproducing the nucleotide sequence according to the invention. Such an overexpression of the new gene(s), proteins or inactivated variants thereof will either positively or negatively have an effect on cell division. Methods to modify the expression levels and/or the activity are known to persons skilled in the art and include for instance overexpression, co-suppression, the use of ribozymes, sense and anti-sense strategies, gene silencing approaches. "Sense strand" refers to the strand of a double-stranded DNA molecule that is homologous to a mRNA transcript thereof. The "anti-sense strand" contains an inverted sequence which is complementary to that of the "sense strand".

Hence, the nucleic acid molecules according to the invention are in particular useful for the genetic manipulation of plant cells in order to modify the characteristics of plants and to obtain plants with modified, preferably with improved or useful phenotypes. Similarly, the invention can also be used to modulate the cell division and the growth of cells, preferentially plant cells, in in vitro cultures.

Thus, the present invention provides for a method for the production of transgenic plants, plant cells or plant tissue comprising the introduction of a nucleic acid molecule or vector of the invention into the genome of said plant, plant cell or plant tissue.

For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells, i.e., a promoter which functions in plant cells. To obtain expression in all tissues of a transgenic plant, preferably constitutive promoters are used, such as the 35 S promoter of CaMV (Odell, Nature 313 (1985), 810–812) or promoters of the polyubiquitin genes of maize (Christensen, Plant Mol. Biol. 18 (1982), 675–689). Furthermore, the expression of the nucleic acid molecules of the invention can be controlled by, e.g., introduction of high constitutive, tissue specific, cell type specific or inducible promoters adjacent to said nucleotide sequence or fragment thereof, multiple gene repeats and other similar techniques. For instance transgenic plants can thus be obtained which can not form feeding cells upon nematode infection of the roots. It is also feasible to generate transgenic plants which are resistant to certain viral infections such as a gemini viral infection. In order to achieve expression in specific tissues of a transgenic plant it is possible to use tissue specific promoters (see, e.g., Stockhaus, EMBO J. 8 (1989), 2245–2251). Known are also promoters which are specifically active in tubers of potatoes or in seeds of different plants species, such as maize, *Vicia*, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Test-system may be employed (Gatz, Mol. Gen. Genet. 227 (1991); 229–237). Further suitable promoters are known to the person skilled in the art and are described, e.g., in Ward (Plant Mol. Biol. 22 (1993), 361–366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability.

In the case that a nucleic acid molecule according to the invention is expressed in sense orientation it is in principle possible to modify the coding sequence in such a way that the protein is located in any desired compartment of the plant cell. These include the nucleus, endoplasmatic reticulum, the vacuole, the mitochondria, the plastids, the apoplast, the cytoplasm etc. Since cyclin-dependent kinases the interacting component of the protein of the invention excert their its effects in the cytoplasm and/or nucleus, corresponding signal sequences are preferred to direct the protein of the invention in the same compartment. Methods how to carry out this modifications and signal sequences ensuring localization in a desired compartment are well known to the person skilled in the art.

Methods for the introduction of foreign DNA into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment, pollen-mediated transformation, plant RNA virus-mediated transformation, liposome-mediated transformation, transformation using wounded or enzyme-degraded immature embryos, or wounded or enzyme-degraded embryogenic callus and other methods known in the art. The vectors used in the method of the invention may contain further functional elements, for example "left border"- and "right border"-sequences of the T-DNA of *Agrobacterium* which allow for stably integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13 (1989), 151–161; Peng, Plant Mol. Biol. 27 (1995), 91–104) and/or by using systems which utilize enzymes capable of promoting homologous recombination in plants (see, e.g., WO97/08331; Bayley, Plant Mol. Biol. 18 (1992), 353–361); Lloyd, Mol. Gen. Genet. 242 (1994), 653–657; Maeser, Mol. Gen. Genet. 230 (1991), 170–176; Onouchi, Nucl. Acids Res. 19 (1991), 6373–6378). Methods for the preparation of appropriate vectors are described by, e.g., Sambrook (Molecular Cloning; A Laboratory Manual, 2nd Edition (1989), Cold Spring Harbor Laboratory Press, Cold Spring Harbor, N.Y.).

Suitable strains of *Agrobacterium tumefaciens* and vectors as well as transformation of *Agrobacteria* and appropriate growth and selection media are well known to those skilled in the art and are described in the prior art (GV3101 (pMK90RK), Koncz, Mol. Gen. Genet. 204 (1986), 383–396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467–8471; Koncz, Plant Mol. Biol. 20 (1992), 963–976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1–22; EP-A-120 516; Hoekema: The Binary Plant Vector System, Offsetdrukkerij Kanters B. V., Alblasserdam (1985), Chapter V, Fraley, Crit. Rev. Plant. Sci., 4, 1–46; An, EMBO J. 4 (1985), 277–287). Although the use of *Agrobacterium tumefaciens* is preferred in the method of the invention, other *Agrobacterium* strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104 (1994), 37–48; Vasil, Bio/Technology 11 (1993), 1553–1558 and Christou (1996) Trends in Plant Science 1, 423–431. Microinjection can be performed as described in Potrykus and Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc.

Methods for transformation of monocotyledonous plants are well know in the art and include *Agrobacterium*-mediated transformation (Cheng et al. 1997—WO9748814; Hiei et al. 1994—WO9400977; Hiei et al. 1998—WO8717813; Rikiishi et al. 1999—WO9904618; Saito et al. 1995—WO9506722) and microprojectile bombardment (Adams et al. 1999—U.S. Pat. No. 5,969,213; Bowen et al. 1998—U.S. Pat. No. 5,736,369; Chang et al. 1994—WO9413822; Lundquist et al. 1999—U.S. Pat. No. 5,990,390; Walker et al. 1999—U.S. Pat. No. 5,955,362).

The term "transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid, or alternatively, may be integrated into the host genome. The resulting transformed plant cell can then be used to regenerate a transformed plant in a manner known by a skilled person.

In general, the plants which can be modified according to the invention and which either show overexpression of a protein according to the invention or a reduction of the synthesis of such a protein can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

Thus, the present invention relates also to transgenic plant cells which contain stably integrated into the genome a nucleic acid molecule according to the invention linked to regulatory elements which allow for expression of the nucleic acid molecule in plant cells and wherein the nucleic acid molecule is foreign to the transgenic plant cell. For the meaning of foreign; see supra. Alternatively, a plant cell having (a) nucleic acid molecule(s) encoding a cyclin-dependent kinase inhibitor present in its genome can be used and modified such that said plant cell expresses the endogenous gene(s) corresponding to these nucleic acid molecules under the control of an heterologous promoter and/or enhancer elements. The introduction of the heterologous promoter and mentioned elements which do not naturally control the expression of a nucleic acid molecule encoding the above described protein using, e.g., gene targeting vectors can be done according to standard methods, see supra and, e.g., Hayashi, Science 258 (1992), 1350–1353; Fritze and Walden, Gene activation by T-DNA tagging. In *Methods in Molecular* biology 44 (Gartland, K. M. A. and Davey, M. R., eds). Totowa: Human Press (1995), 281–294) or transposon tagging (Chandlee, Physiologia Plantarum 78 (1990), 105–115). Suitable promoters and other regulatory elements such as enhancers include those mentioned hereinbefore.

The presence and expression of the nucleic acid molecule in the transgenic plant cells leads to the synthesis of a cyclin-dependent kinase inhibitor and leads to physiological and phenotypic changes in plants containing such cells.

Thus, the present invention also relates to transgenic plants and plant tissue comprising transgenic plant cells according to the invention. Due to the (over) expression of a cell cycle interacting protein of the invention, e.g., at developmental stages and/or in plant tissue in which they do not naturally occur these transgenic plants may show various physiological, developmental and/or morphological modifications in comparison to wild-type plants. For example, these transgenic plants may display an altered cell elongation and/or for improved and/or disease resistance.

Therefore, part of this invention is the use of CKIs and the encoding DNA sequences to modulate plant cell division and/or growth in plant cells, plant tissues, plant organs and/or whole plants. To the scope of the invention also belongs a method to influence the activity of cyclin-dependent protein kinase in a plant cell by transforming the plant cell with a nucleic acid molecule according to the invention and/or manipulation of the expression of said molecule. More in particular using a nucleic acid molecule according to the invention, the disruption of plant cell division can be accomplished by interfering in the activity of cyclin-dependent protein kinases or their inhibitors. The latter goal may also be achieved, for example, with methods for reducing the amount of active cyclin-dependent kinase inhibitor.

Hence, the invention also relates to a transgenic plant cell which contains (stably integrated into the genome) a nucleic acid molecule according to the invention or part thereof, wherein the transcription and/or expression of the nucleic acid molecule or part thereof leads to reduction of the synthesis of a cyclin-dependent kinase inhibitor.

In a preferred embodiment, the reduction is achieved by an anti-sense, sense, ribozyme, co-suppression and/or dominant mutant effect.

"Antisense" and "antisense nucleotides" means DNA or RNA constructs which block the expression of the naturally occurring gene product.

The provision of the nucleic acid molecules according to the invention opens up the possibility to produce transgenic plant cells with a reduced level of the protein as described above and, thus, with a defect in the accumulation of a cyclin-dependent kinase inhibitor. Techniques how to achieve this are well known to the person skilled in the art. These include, for example, the expression of antisense-RNA, ribozymes, of molecules which combine antisense and ribozyme functions and/or of molecules which provide for a co-suppression effect; see also supra. When using the antisense approach for reduction of the amount of cyclin-dependent kinase inhibitor in plant cells, the nucleic acid molecule encoding the antisense-RNA is preferably of homologous origin with respect to the plant species used for transformation. However, it is also possible to use nucleic acid molecules which display a high degree of homology to endogenously occurring nucleic acid molecules encoding a cyclin-dependent kinase inhibitor. In this case the homology is preferably higher than 80%, particularly higher than 90% and still more preferably higher than 95%.

The reduction of the synthesis of a protein according to the invention in the transgenic plant cells can result in an alteration in, e.g., cell division. In transgenic plants comprising such cells this can lead to various physiological, developmental and/or morphological changes.

Thus, the present invention also relates to transgenic plants comprising the above-described transgenic plant cells. These may show, for example, reduced or enhanced growth characteristics.

The present invention also relates to cultured plant tissues comprising transgenic plant cells as described above which either show overexpression of a protein according to the invention or a reduction in synthesis of such a protein.

Any transformed plant obtained according to the invention can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention. As mentioned before, the present invention is in principle applicable to any plant and crop that can be transformed with any of the transformation method known to those skilled in the art and includes for instance corn, wheat, barley, rice, oilseed crops, cotton, tree species, sugar beet, cassava, tomato, potato, numerous other vegetables, fruits.

In yet another aspect, the invention also relates to harvestable parts and to propagation material of the transgenic plants according to the invention which either contain transgenic plant cells expressing a nucleic acid molecule according to the invention or which contain cells which show a reduced level of the described protein. Harvestable parts can be in principle any useful parts of a plant, for example, flowers, pollen, seedlings, tubers, leaves, stems, fruit, seeds, roots etc. Propagation material includes, for example, seeds, fruits, cuttings, seedlings, tubers, rootstocks etc.

As mentioned above, the cyclin-dependent kinase inhibitors of the invention display distinct expression patterns in plants and cell suspension. Thus, the regulatory sequences that naturally drive the expression of the above described cyclin-dependent kinase inhibitors may prove useful for the expression of heterologous DNA sequences in certain plant tissues and/or at different developmental stages in plant development.

Accordingly, in a further aspect the present invention relates to a regulatory sequence of a promoter naturally regulating the expression of a nucleic acid molecule of the invention described above or of a nucleic acid molecule homologous to a nucleic acid molecule of the invention. The expression patter of CKI genes has been studied in detail in accordance with the present invention and is summarized in Example 8, 9 and in particular in Example 13. With methods well known in the art it is possible to isolate the regulatory sequences of the promoters that naturally regulate the expression of the above-described DNA sequences. For example, using the CKI genes as probes a genomic library consisting of plant genomic DNA cloned into phage or bacterial vectors can be screened by a person skilled in the art. Such a library consists e.g. of genomic DNA prepared from seedlings, fractionized in fragments ranging from 5 kb to 50 kb, cloned into the lambda GEM11 (Promega) phages. Phages hybridizing with the probes can be purified. From the purified phages DNA can be extracted and sequenced. Having isolated the genomic sequences corresponding to the genes encoding the above-described cyclin-dependent kinase inhibitors, it is possible to fuse heterologous DNA sequences to these promoters or their regulatory sequences via transcriptional or translational fusions well known to the person skilled in the art. In order to identify the regulatory sequences and specific elements of the CKI genes, 5'-upstream genomic fragments can be cloned in front of marker genes such as luc, gfp or the GUS coding region and the resulting chimeric genes can be introduced by means of *Agrobacterium tumefaciens* mediated gene transfer into plants or transfected into plant cells or plant tissue for transient expression. The expression pattern observed in the transgenic plants or transfected plant cells containing the marker gene under the control of the regulatory sequences of the invention reveal the boundaries of the promoter and its regulatory sequences. Preferably, said regulatory sequence is capable of conferring expression of a heterologous DNA sequence in (a) young root meristems, pericycle cells in the vascular tissue, shoot apical meristem, surface and tip of young leaves, epidermis of the stem in young seedlings, tapetal layer of the anthers in pollen grains, flower buds and mature ovaries, embryos at the globular, heart and torpedo stages, embryonic root;

(b) root and shoot apical meristems, young differentiating leaves, flower buds and young flowers, ovary wall, funiculus, ovules and pollen grains, embryo at the globular stage, embryonic root; or (c) main and lateral root meristems and shoot apical meristems, vascular tissue, pericycle, mature ovaries, globular and heart embryonic root.

In context with the present invention, the term "regulatory sequence" refers to sequences which influence the specificity and/or level of expression, for example in the sense that they confer cell and/or tissue specificity; see supra. Such regions can be located upstream of the transcription initiation site, but can also be located downstream of it, e.g., in transcribed but not translated leader sequences.

The term "promoter", within the meaning of the present invention refers to nucleotide sequences necessary for transcription initiation, i.e. RNA polymerase binding, and may also include, for example, the TATA box.

The term "nucleic acid molecule homologous to a nucleic acid molecule of the invention", as used herein includes promoter regions and regulatory sequences of other CKI genes, such as the gene encoding the CKI1 protein as well as genes from other species, for example, maize, alfalfa, potato, sorghum, millet, coix, barley, wheat and rice which are homologous to the CKI genes and which display substantially the same expression pattern. Such promoters are characterized by their capability of conferring expression of a heterologous DNA sequence in root meristems and other tissues mentioned above.

Thus, according to the present invention, regulatory sequences from any species can be used that are functionally homologous to the regulatory sequences of the promoter of the above defined CKI specific nucleic acid molecules, or promoters of genes that display an identical or similar pattern of expression, in the sense of being expressed in the above-mentioned tissues and cells. However, the expression conferred by the regulatory sequences of the invention may not be limited to, for example, root meristem cells but can include or be restricted to, for example, subdomains of meristems. The particular expression pattern may also depend on the plant/vector system employed. However, expression of heterologous DNA sequences driven by the regulatory sequences of the invention predominantly occurs in the root meristem unless certain elements of the regulatory sequences of the invention, were taken and designed by the person skilled in the art to control the expression of a heterologous DNA sequence in other cell types.

It is also immediately evident to the person skilled in the art that further regulatory elements may be added to the regulatory sequences of the invention. For example, transcriptional enhancers and/or sequences which allow for induced expression of the regulatory sequences of the invention may be employed. A suitable inducible system is for example tetracycline-regulated gene expression as described, e.g., by Gatz, supra.

The regulatory sequence of the invention may be derived from the CKI genes of *Arabidopsis thaliana* or alfalfa although other plants may be suitable sources for such regulatory sequences as well.

Usually, said regulatory sequence is part of a recombinant DNA molecule. In a preferred embodiment of the present invention, the regulatory sequence in the recombinant DNA molecule is operatively linked to a heterologous DNA sequence.

The term heterologous with respect to the DNA sequence being operatively linked to the regulatory sequence of the invention means that said DNA sequence is not naturally linked to the regulatory sequence of the invention. Expression of said heterologous DNA sequence comprises transcription of the DNA sequence, preferably into a translatable mRNA. Regulatory elements ensuring expression in eukaryotic cells, preferably plant cells, are well known to those skilled in the art. They usually comprise poly-A signals ensuring termination of transcription and stabilization of the transcript, see also supra. Additional regulatory elements may include transcriptional as well as translational enhancers; see supra.

In a preferred embodiment, the heterologous DNA sequence of the above-described recombinant DNA molecules encodes a peptide, protein, antisense RNA, sense RNA and/or ribozyme. The recombinant DNA molecule of the invention can be used alone or as part of a vector to express heterologous DNA sequences, which, e.g., encode proteins for, e.g., the control of disease resistance, modulation of nutrition value or diagnostics of CKI related gene expression. The recombinant DNA molecule or vector containing the DNA sequence encoding a protein of interest is introduced into the cells which in turn produce the protein of interest. For example, the regulatory sequences of the invention can be operatively linked to sequences encoding Barstar and Barnase, respectively, for use in the production of male and female sterility in plants.

On the other hand, said protein can be a scorable marker, e.g., luciferase, green fluorescent protein or β-galactosidase. This embodiment is particularly useful for simple and rapid screening methods for compounds and substances described herein below capable of modulating CKI specific gene expression. For example, a cell suspension can be cultured in the presence and absence of a candidate compound in order to determine whether the compound affects the expression of genes which are under the control of regulatory sequences of the invention, which can be measured, e.g., by monitoring the expression of the above-mentioned marker. It is also immediately evident to those skilled in the art that other marker genes may be employed as well, encoding, for example, a selectable marker which provides for the direct selection of compounds which induce or inhibit the expression of said marker.

The regulatory sequences of the invention may also be used in methods of antisense approaches. The antisense RNA may be a short (generally at least 10, preferably at least 14 nucleotides, and optionally up to 100 or more nucleotides) nucleotide sequence formulated to be complementary to a portion of a specific mRNA sequence and/or DNA sequence of the gene of interest. Standard methods relating to antisense technology have been described; see, e.g., Klann, Plant Physiol. 112 (1996), 1321–1330. Following transcription of the DNA sequence into antisense RNA, the antisense RNA binds to its target sequence within a cell, thereby inhibiting translation of the mRNA and downregulating expression of the protein encoded by the mRNA. Thus, in a further embodiment, the invention relates to nucleic acid molecules of at least 15 nucleotides in length hybridizing specifically with a regulatory sequence as described above or with a complementary strand thereof. For the possible applications of such nucleic acid molecules, see supra.

The present invention also relates to vectors, particularly plasmids, cosmids, viruses and bacteriophages used conventionally in genetic engineering that comprise a recombinant DNA molecule of the invention. Preferably, said vector is an expression vector and/or a vector further comprising a selection marker for plants. For example of suitable selector markers, see supra. Methods which are well known to those skilled in the art can be used to construct recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the recombinant DNA molecules and vectors of the invention can be reconstituted into liposomes for delivery to target cells.

The present invention furthermore relates to host cells transformed with a regulatory sequence, a DNA molecule or vector of the invention. Said host cell may be a prokaryotic or eukaryotic cell; see supra.

In a further preferred embodiment, the present invention provides for a method for the production of transgenic plants, plant cells or plant tissue comprising the introduction of a nucleic acid molecule, recombinant DNA molecule or vector of the invention into the genome of said plant, plant cell or plant tissue. For the expression of the heterologous DNA sequence under the control of the regulatory sequence according to the invention in plant cells, further regulatory sequences such as poly A tail may be fused, preferably 3' to the heterologous DNA sequence, see also supra. Further possibilities might be to add Matrix Attachment Sites at the borders of the transgene to act as "delimiters" and insulate against methylation spread from nearby heterochromatic sequences. Methods for the introduction of foreign DNA into plants, plant cells and plant tissue are described above.

Thus, the present invention relates also to transgenic plant cells which contain stably integrated into the genome a recombinant DNA molecule or vector according to the invention.

Furthermore, the present invention also relates to transgenic plants and plant tissue comprising the above-described transgenic plant cells. These plants may show, for example, increased disease resistance.

In yet another aspect the invention also relates to harvestable parts and to propagation material of the transgenic plants according to the invention which contain transgenic plant cells described above. Harvestable parts and propagation material can be in principle any useful part of a plant; see supra.

With the regulatory sequences of the invention, it will be possible to study in vivo CKI specific gene expression. Furthermore, since CKI specific gene expression has different patterns in different stages of physiological and pathological conditions, it is now possible to determine further regulatory sequences which may be important for the up- or down-regulation of CKI gene expression, for example in response to ions or elicitors. In addition, it is now possible to in vivo study mutations which affect different functional or regulatory aspects of specific gene expression in the cell cycle.

The in vivo studies referred to above will be suitable to further broaden the knowledge on the mechanisms involved in the control of the cell cycle. To date nothing is known about the activity, nature or mode of act ion of CKIs in the cell cycle or about their role during plant development. Expression of heterologous genes or antisense RNA under the control of the regulatory sequence of the present invention in plants and plant cells may allow the understanding of the function of each of these proteins in the plant. The present invention further relates to a method for the identification of an activator or inhibitor of genes encoding cyclin-dependent kinase inhibitors comprising the steps of:

(a) providing a plant, plant cell, or plant tissue comprising a recombinant DNA molecule comprising a readout system operatively linked to a regulatory sequence of the invention;

(b) culturing said plant cell or tissue or maintaining said plant in the presence of a compound or a sample comprising a plurality of compounds under conditions which permit expression of said readout system;

(c) identifying or verifying a sample and compound, respectively, which leads to suppression or activation and/or enhancement of expression of said readout system in said plant, plant cell, or plant tissue.

The present invention further relates to a method for identifying and obtaining an activator or inhibitor of cyclin-dependent kinase inhibitors comprising the steps of:

(a) combining a compound to be screened with a reaction mixture containing the protein of the invention and a readout system capable of interacting with the protein under suitable conditions;

(b) maintaining said reaction mixture in the presence of the compound or a sample comprising a plurality of compounds under conditions which permit interaction of the protein with said readout system;

(c) identifying or verifying a sample and compound, respectively, which leads to suppression or activation of the readout system.

The term "read out system" in context with the present invention means a DNA sequence which upon transcription and/or expression in a cell, tissue or organism provides for a scorable and/or selectable phenotype. Such read out systems are well known to those skilled in the art and comprise, for example, recombinant DNA molecules and marker genes as described above and in the appended example.

The term "plurality of compounds" in a method of the invention is to be understood as a plurality of substances which may or may not be identical. Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cell cycle interacting proteins. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound from the original sample identified as containing the compound capable of suppressing or activating cyclin-dependent kinase inhibitors, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. Preferably, the compound identified according to the above described method or its derivative is further formulated in a form suitable for the application in plant breeding or plant cell and tissue culture.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879–880; Hupp, Cell 83 (1995), 237–245; Gibbs, Cell 79 (1994), 193–198 and references cited supra). Furthermore, genes encoding a putative regulator of a cyclin-dependent kinase inhibitor and/or which excert their effects up- or downstream the cell cycle interacting protein of the invention may be identified using, for example, insertion mutagenesis using, for example, gene targeting vectors known in the art (see, e.g., Hayashi, Science 258 (1992), 1350–1353; Fritze and Walden, Gene activation by T-DNA tagging. In *Methods in Molecular biology* 44 (Gartland, K. M. A. and Davey, M. R., eds). Totowa: Human Press (1995), 281–294) or transposon tagging (Chandlee, Physiologia Plantarum 78 (1990), 105–115). Said compounds can also be functional derivatives or analogues of known inhibitors or activators. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art. Furthermore, peptidomimetics and/or computer aided design of appropriate derivatives and analogues can be used, for example, according to the methods described above. The cell or tissue that may be employed in the method of the invention preferably is a host cell, plant cell or plant tissue of the invention described in the embodiments hereinbefore.

Determining whether a compound is capable of suppressing or activating cell cycle interacting proteins can be done, for example, by monitoring DNA duplication and cell division. It can further be done by monitoring the phenotypic characteristics of the cell of the invention contacted with the compounds and compare it to that of wild-type plants. In an additional embodiment, said characteristics may be compared to that of a cell contacted with a compound which is either known to be capable or incapable of suppressing or activating cell cycle interacting proteins.

The inhibitor or activator identified by the above-described method may prove useful as a herbicide, pesticide and/or as a plant growth regulator. Thus, in a further embodiment the invention relates to a compound obtained or identified according to the method of the invention said compound being an activator of a cyclin-dependent kinase inhibitor or an inhibitor of a cyclin-dependent kinase inhibitor.

Such useful compounds can be for example transacting factors which bind to the cyclin-dependent kinase inhibitor of the invention. Identification of transacting factors can be carried out using standard methods in the art (see, e.g., Sambrook, supra, and Ausubel, supra). To determine whether a protein binds to the protein of the invention, standard native gel-shift analyses can be carried out. In order to identify a transacting factor which binds to the protein of the invention, the protein of the invention can be used as an affinity reagent in standard protein purification methods, or as a probe for screening an expression library. Once the transacting factor is identified, modulation of its binding to the cyclin-dependent kinase inhibitor of the invention can be pursued, beginning with, for example, screening for inhibitors against the binding of the transacting factor to the protein of the present invention. Activation or repression of cyclin-dependent kinase inhibitor could then be achieved in plants by applying of the transacting factor (or its inhibitor) or the gene encoding it, e.g. in a vector for transgenic plants. In addition, if the active form of the transacting factor is a dimer, dominant-negative mutants of the transacting factor could be made in order to inhibit its activity. Furthermore, upon identification of the transacting factor, further components in the pathway leading to activation (e.g. signal transduction) or repression of a gene involved in the control of cell cycle then can be identified. Modulation of the activities of these components can then be pursued, in order to develop additional drugs and methods for modulating the cell cycle in animals and plants.

The invention also relates to a diagnostic composition comprising at least one of the aforementioned nucleic acid molecules, vectors, proteins, antibodies, regulatory sequences, recombinant DNA molecules, or compounds and optionally suitable means for detection.

Said diagnostic compositions may be used for methods for detecting expression of cyclin-dependent kinase inhibitors by detecting the presence of the corresponding mRNA which comprises isolation of mRNA from a cell and contacting the mRNA so obtained with a probe comprising a nucleic acid probe as described above under hybridizing conditions, detecting the presence of mRNA hybridized to the probe, and thereby detecting the expression of the protein in the cell. Further methods of detecting the presence of a protein according to the present invention comprises immunotechniques well known in the art, for example enzyme linked immunosorbent assay. Furthermore, it is possible to use the nucleic acid molecules according to the invention as molecular markers in plant breeding.

The person skilled in the art can use proteins according to the invention from other organisms such as yeast and animals to influence cell division progression in those other organisms such as mammals or insects. In a preferred embodiment one or more DNA sequences, vectors or proteins of the invention or the above-described antibody or compound are, for instance, used to specifically interfere in the disruption of the expression levels of genes involved in G1/S and/or G2/M transition in the cell cycle process in transformed plants, particularly:

in the complete plant
    in selected plant organs, tissues or cell types
    under specific environmental conditions, including abiotic stress such as cold, heat, drought or salt stress or biotic stress such as pathogen attack
    during specific developmental stages.

Specifically the plant cell division rate and/or the inhibition of a plant cell division can be influenced by (partial) elimination of a gene or reducing the expression of a gene encoding a protein according to the invention. Said plant cell division rate and/or the inhibition of a plant cell division can also be influenced by eliminating or inhibiting the activity of the protein according to the invention by using for instance antibodies directed against said protein. As a result of said elimination or reduction greater organisms or specific organs or tissues can be obtained; greater in volume and in mass too. Furthermore inhibition of cell division by various adverse environmental conditions such as drought, high salt content, chilling and the like can be delayed or prevented by reduction of said expression of a gene according to the invention. The division rate of a plant cell can also be influenced in a transformed plant by overexpression of a sequence according to the invention. Said transformed plant can be obtained by transforming a plant cell with a gene encoding a polypeptide concerned or fragment thereof alone or in combination, whereas the plant cell may belong to a monocotyledonous or dicotyledonous plant. For this purpose tissue specific promoters, in one construct or being present as a separate construct in addition to the sequence concerned, can be used. Therefore an important aspect of the current invention is a method to modify plant architecture by overproduction or reduction of expression of a sequence according to the invention under the control of a tissue, cell or organ specific promoter. Another aspect of the present invention is a method to modify the growth inhibition of plants caused by environmental stress conditions above mentioned by appropriate use of sequences according to the invention. Surprisingly using a polypeptide or fragment thereof according to the invention or using antisense RNA or any method to reduce the expression of the gene according to the invention, cell division in the meristem of both main and lateral roots, shoot apical or the vascular tissue of a plant can be manipulated. Furthermore any of the DNA sequences of the invention as well as those encoding CDK1 can be used to manipulate (reduce or enhance) the level of endopolyploidy and thereby increasing the storage capacity of, for example, endosperm cells.

Another aspect of the current invention is that one or more DNA sequences, vectors or proteins, regulatory sequences or recombinant DNA molecules of the invention or the above-described antibody or compound can be used to modulate, for instance, endoreduplication in storage cells, storage tissues and/or storage organs of plants or parts thereof. The term "endoreduplication" means recurrent DNA replication without consequent mitosis and cytokinesis.

Preferred target storage organs and parts thereof for the modulation of endoreduplication are, for instance, seeds (such as from cereals, oilseed crops), roots (such as in sugar beet), tubers (such as in potato) and fruits (such as in vegetables and fruit species). Furthermore it is expected that increased endoreduplication in storage organs and parts thereof correlates with enhanced storage capacity and as such with improved yield. In yet another embodiment of the invention, a plant with modulated endoreduplication in the whole plant or parts thereof can be obtained from a single plant cell by transforming the cell, in a manner known to the skilled person, with the above-described means.

In view of the foregoing, the present invention also relates to the use of a DNA sequence, vector, protein, antibody, regulatory sequences, recombinant DNA molecule, nucleic acid molecules or compound of the invention for modulating plant cell cycle, plant cell division and/or growth, for influencing the activity of cyclin-dependent protein kinase, for disrupting plant cell division by influencing the presence or absence or by interfering in the expression of a cyclin-dependent protein kinase inhibitor, for modifying growth inhibition of plants caused by environmental stress conditions, for inducing male or female sterility, for influencing cell division progression in a host as defined above or for use in a screening method for the identification of inhibitors or activators of cell cycle proteins. Beside the above described possibilities to use the nucleic acid molecules according to the invention for the genetic engineering of plants with modified characteristics and their use to identify homologous molecules, the described nucleic acid molecules may also be used for several other applications, for example, for the identification of nucleic acid molecules which encode proteins which interact with the cell cycle proteins described above. This can be achieved by assays well known in the art such as those described above and also included, for example, as described in Scofield (Science 274 (1996), 2063–2065) by use of the so-called yeast "two-hybrid system"; see also the appended examples. In this system the protein encoded by the nucleic acid molecules according to the invention or a smaller part thereof is linked to the DNA-binding domain of the GAL4 transcription factor. A yeast strain expressing this fusion protein and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of a protein of the invention, the complex is able to direct expression of the reporter gene. In this way the nucleic acid molecules according to the invention and the encoded peptide can be used to identify peptides and proteins interacting with cell cycle interacting proteins. It is apparent to the person skilled in the art that this and similar systems may then further be exploited for the identification of inhibitors of the binding of the interacting proteins.

Other methods for identifying compounds which interact with the proteins according to the invention or nucleic acid molecules encoding such molecules are, for example, the in vitro screening with the phage display system as well as filter binding assays or "real time" measuring of interaction using, for example, the BIAcore apparatus (Pharmacia); see references cited supra.

Furthermore, it is possible to use the nucleic acid molecules according to the invention as molecular markers in plant breeding. Moreover, the overexpression of nucleic acid molecules according to the invention may be useful for the alteration or modification of plant/pathogene interaction. The term "pathogens" includes, for example, bacteria, viruses and fungi as well as protozoa.

These and other embodiments are disclosed and encompassed by the description and examples of the present invention. Further literature concerning any one of the methods, material, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, http://www.fmi.ch/biology/research_tools.html, http://www.tigr.org/, are known to the person skilled in the art and can also be obtained using, e.g., http://www.lycos.com. An overview of patent information in biotechnology and a survey of relevant sources of patent information useful for retrospective searching and for current awareness is given in Berks, TIBTECH 12 (1994), 352–364.

In accordance with the present invention previously unrecognized amino acid sequence motifs have been identified in plant cyclin-dependent kinase inhibitors (CKIs or ICKs) which allow classification of said ICKs in at least three structural groups. The different identified motifs are summarized in Table 2 and graphically represented in FIG. 1. Motifs "1" (consensus sequence) {$FX_2KYNFD$}, SEQ ID NO: 34), "2" (consensus sequence {[P/L]LXGRYEW}, SEQ ID No.:35) and "3" (consensus sequence {EXE[D/E] FFX$_3$E}, SEQ ID NO:36) are comprised in the carboxy-terminal part of plant ICK proteins and are conserved in all plant ICKs known in the art to date. The region comprising said motifs 1, 2 and 3 is furthermore homologous to the N-terminal regions of animal ICKs including p21Cip1, p27Kip1 and p57Kip2. In animal ICKs this region is known to be required for interaction with both CDKs and cyclins (Chen et al. 1996, Mol. Cell. Biol. 16, 4673–82; Matsuoka et al. 1995, Genes Dev. 9, 650–62; Nakayama and Nakayama 1998, Bioessays 20, 1020–29). The amino-terminus of plant ICKs known in the art furthermore container either: (i) three conserved motifs e.g. included in the alfalfa CKI and the *Arabidopsis* CK13, CK14 and CK15; said motifs are motif "4" (consensus sequence {YXQLRSRR}, SEQ ID No:37), motif "5" (consensus sequence {MGKY[M/I][K/R]KX[K/R]}, SEQ ID NO:38 and motif "6" (consensus sequence {SXGVRTRA}, SEQ ID NO:39); or (ii) one of said motifs, i.e. motif "4" (SEQ ID NO:37) as found in e.g. the *Chenopodium* ICK and in the *Arabidopsis* ICK1; or (iii) none of said motifs, e.g. as in the *Arabidopsis* ICKs ICK2, ICK6 and ICK7.

The presence or absence of one or more of the identified motifs is likely to influence the function of the ICKs e.g. by enabling or preventing specific protein—protein interactions. Experimental data leading to the present invention underscore this hypothesis. Indeed, in plant transformation experiments as outlined in Examples 10 and 16, a total of 39 transgenic *Arabidopsis* plants constitutively expressing ICK2 at high levels were obtained. In similar experiments, 5 and 0 (zero) transgenic *Arabidopsis* plants constitutively expressing ICK3 and ICK4, respectively, were obtained. *Arabidopsis* plants containing recombinant ICK3 DNA furthermore only displayed very low levels of ICK3 expression. These functional data obtained in plants indicate that high levels of either ICK3 or ICK4 (both containing all six motifs described supra) prevent and/or decrease frequency of plant transformation and/or plant regeneration whereas these processes are not significantly influenced by high levels of ICK2 (which contains only the carboxy-terminal motifs 1, 2 and 3 as defined higher).

As described herein, overall homology between plant ICKs is very low, i.e. lower than 40% whereas identifies are under 30%. This hampers the identification of novel ICK genes in plants. Therefore, the delineation of conserved motifs is of utmost importance to enhance identification of said novel plant ICK genes. Presence or absence of (some of) said motifs enabling structural classification of plant ICKs can possibly also assist in prediction of ICK function thus preventing undue experimentation. Finally, conserved ICK-motifs as identified in the current invention enable construction of functional recombinant plant ICK proteins such as ICK orthologues, via domain shuffling and/or with novel combinations and/or positions of said motifs in said recombinant ICK proteins. Such recombinant ICK proteins will open more new avenues to modifications of plant growth and/or development.

Accordingly, one embodiment of the current invention includes DNA sequences coding for a functional plant ICK or an ortholog thereof, which furthermore comprise:

(a) DNA sequences encoding a peptide with the consensus sequence as given in SEQ ID NO:34 or a peptide that is at least 70% identical thereto; and/or (b) DNA sequences encoding a peptide with the consensus sequence as given in SEQ ID No:35 or a peptide that is at least 70% identical thereto; and/or (c) DNA sequences encoding a peptide with the consensus sequence as given in SEQ ID NO:36 or a peptide that is at least 70% identical thereto; and/or (d) DNA sequences encoding a peptide with the consensus sequence as given in SEQ ID NO:37 or a peptide that is at least 70% identical thereto; and/or (e) DNA sequences encoding a peptide with the consensus sequence as given in SEQ ID NO:38 or a peptide that is at least 70% identical thereto; and/or (f) DNA sequences encoding a peptide with the consensus sequence as given in SEQ ID No:39 or a peptide that is at least 70% identical thereto.

In accordance with the present invention, growth characteristics of plants may be modified by introducing into a plant or plant cell, a cyclin-dependent kinase inhibitor (CKI). For example, a CKI may be introduced into the plant cell by micro-injection, permeation, or biolistics. Alternatively, growth characteristics of a plant or plant cell are achieved by introducing into a plant cell a nucleic acid molecule encoding a CKI under the control of a promoter and/or other regulatory sequences which function in plants. Plants with altered growth characteristics are obtained by regenerating from the transformed plant cell. As used herein, "plant cell" encompasses cells from plants having a cell wall or cells with the walls removed, i.e, protoplasts. Methods of introducing nucleic acid molecules into plant cells are well known in the art and discussed herein. Usually, the nucleic acid molecule encoding a CKI under the control of a regulatory region is in the form of a vector or genetic costruct as hereinbefore described. The genetic construct when expressed in a cell, is able to up-regulate or down-regulate cyclin-dependent kinase (CDK) activity. Preferentially, such genetic construct consists of a cyclin-dependent kinase inhibitor (CKI) protein expressed under control of a constitutive or regulated promoter. Plants contain many different CKIs. In plants, the CKI gene preferred for this application is naturally expressed in epidermal cells and/or encodes a protein that shows structural homology to the CKI2 protein of *Arabidopsis thaliana*. As used herein, the CKI2 protein is also refered to as "ICK2". The nucleotide sequence for the complete ICK2 coding region is contained in the clone pFL39 and set forth in SEQ ID NO:1. The corresponding amino acid sequence for pFL39 is set forth in SEQ ID NO:2.

The methods of the present invention include, e.g., altering plant cell size, alering plant cell number, altering leaf shape, altering floral petal shape, altering floral petal size, altering stomata size, altering venation pattern, facilitating the transition from the mitotic cycle to G1 arrest in a plant cell, altering endoreduplication in a plant cell, altering the ploidy level in a plant cell, and altering plant seed size. The resultant transgenic plants which express a CKI of the present invention are also provided.

For example, in order to disrupt plant cell division, a CKI is introduced into a plant cell. Alternatively, a nucleic acid molecule encoding a CKI under the control of a promoter which functions in plants is introduced into a plant cell. A method for increasing the level of cyclin-dependent kinase inhibitor in a plant cell is also provided. The method comprises introducing into a plant cell a cyclin-dependent kinase inhibitor. Alternatively, a method for increasing the level of cyclin-dependent kinase inhibitor in a plant cell may be accomplished by introducing into a plant cell a nucleic acid molecule encoding a cyclin-dependent kinase inhibitor under the control of a regulatory sequence which controls the expression of the cyclin dependent kinase inhibitor.

The present invention also provides a method for modifying plant cell size which comprises introducing into a plant cell a cyclin-dependent kinase inhibitor. Plant cell size may also be modified by introducing into a plant cell a nucleic acid molecule encoding a cyclin-dependent kinase inhibitor under the control of a promoter which functions in plants. Plant cells may be modified in many different parts of the plant such as the leaves, roots, stems, petioles, floral petals, etc. Different cell types may be modified such as e.g., epidermal cells, palissade cells and mesophyl cells. Preferably, plant cell size is increased.

The present invention also provides a method for modifying cell number in a plant which comprises introducing into a plant cell a nucleic acid molecule encoding a cyclin-dependent kinase inhibitor under the control of a promoter which functions in plants and regenerating a plant with modified cell number. Preferably, cell number is decreased.

Plant tissues or organs consisting of larger and fewer cells, as those obtainable by CKI2 overexpression, have several agriculturally and end-use advantages over non-modified plants. For instance, less and larger cells suggests that the ratio of non-digestible material (e.g. cell wall lignins) over digestible material is smaller, resulting in an increased digestibility of the plant material. This is of particular importance for forage crops including straw derived from cereals or grains used for livestock feed. It increases feed efficiency both in terms of processing of feeds as well as animal nutritional/energy requirements. Earlier attempts to reduce the amount of non-digestable material (e.g. by down-regulation of lignin biosynthesis, cf. Bm (brown-midrib mutant) in maize) proved the value of this strategy. Certain processes such as the malting of cereals for beer production requires that insoluble material have to be removed. It is expected that a modification of cell size/cell number is beneficial for this process. Similarly it is expected that the nutritional value of plants with less and fewer cells be significantly modified compared to control plants. Fewer cells mean fewer membranes and a reduced amount of membrane soluble compounds. Plant material having fewer and larger cells correlates with modified texture and taste.

The present invention also has applications in altering wood quality. Spring and summer wood have very different properties due to differences in cell size. Thus, in another aspect of the invention, expression of an ICK gene under the control of a promoter specifically expressed during spring wood leads to an increase in the cell size and thus an alteration of spring wood quality.

Another advantage of the invention is that larger cells have larger vacuoles and as such an increased potential to store compounds of industrial and/or pharmaceutical value. CKI2 overexpression may also increase the size of gland cells which store valuable compounds.

In accordance with the present invention, there is provided a method of altering leaf shape in a plant which comprises introducing into a plant cell a nucleic acid molecule encoding a cyclin-dependent kinase inhibitor under the control of a promoter which functions in plants and regenerating a plant therefrom having altered leaf shape. For example, plants having more highly serrated or deeply lobed leaves may be produced.

Also provided is a method of increasing stomata size of a plant which comprises introducing into a plant cell a nucleic acid molecule encoding a cyclin-dependent kinase inhibitor under the control of a promoter which functions in plants and regenerating a plant therefrom having increased stomata size.

A method of altering floral petal shape in a plant which comprises introducing into a plant cell a nucleic acid molecule encoding a cyclin-dependent kinase inhibitor under the control of a promoter which functions in plants and regenerating a plant therefrom having flowers with altered petal shape.

The present invention also provides a method of altering floral petal size in a plant which comprises introducing into a plant cell a nucleic acid molecule encoding a cyclin-dependent kinase inhibitor under the control of a promoter which functions in plants and regenerating a plant therefrom having flowers with altered petal size. Preferably, petal size is reduced when compared to wild type plants.

The venation pattern in a plant leaf may also be altered by introducing into a plant cell a nucleic acid molecule encoding a cyclin-dependent kinase inhibitor under the control of a promoter which functions in plants and regenerating a plant therefrom having leaves with an altered venation pattern.

Also in accordance with the present invention, there is provided a method of facilitating the transition from the mitotic cycle to G1 arrest in a plant cell which comprises introducing into a plant cell a cyclin-dependent kinase inhibitor.

Alternatively, the method of facilitating the transition from the mitotic cycle to G1 arrest in a plant cell may be accomplished by introducing into a plant cell a nucleic acid molecule encoding a cyclin-dependent kinase inhibitor under the control of a promoter which functions in plants. Resultant cells exhibit a decrease in endoreduplication. This decrease in endoreduplication results in a lower ploidy level in the plant cell.

The present invention further provides a method of decreasing plant seed size which comprises introducing into a plant cell a nucleic acid molecule encoding a cyclin-dependent kinase inhibitor under the control of a promoter which functions in plants and regenerating a plant having decreased seed size compared to wild type plants.

The practice of any of the aforementioned methods results in plant cells and plant parts and/or whole plants exhibiting altered characteristics. For example, the present invention provides a transgenic plant, an essentially derived variety thereof, a plant part, or plant cell which comprises a nucleotide sequence encoding a cyclin-dependent kinase inhibitor under the control of a promoter which functions in plants wherein said nucleotide sequence encoding a cyclin-dependent kinase inhibitor is heterologous to the genome of the transgenic plant or has been introduced into the transgenic plant, plant part or plant cell by recombinant DNA means.

Thus, the present invention provides transgenic plants having altered growth characteristics such as altered leaf shape, e.g., leaves which are more highly serrated or deeply lobed than wild type plants. Also provided are transgenic plants having flowers with altered petal shapes and/or petal sizes. Transgenic plants having altered venation patterns, and altered stomata size are also provided.

The present invention also provides transgenic plants having altered ploidy levels such as an increase or a decrease in ploidy level.

In accordance with the present invention, transgenic plants are provided which have decreased seed size. Transgenic plants are also provided which have altered cell numbers. For example, plants are provided having increased cell number or decreased cell number. Transgenic plants are also provided comprising cells of increased size, as are plants having leaves with increased stomata size.

One embodiment of the invention relates to the use of CKI2 under a constitutive (e.g. CaMV 35S) or leaf-specific (e.g. small subunit of rubisco, chlorophyll a/b binding protein) promoter. This will result in less cell divisions, increased cell size and consequently less cell wall formation in transgenic plants. Cell walls are the major source of unextractable and undigestible plant components. Thus, CKI2 expression in leaves can be desirable in crops such as tea and tobacco, as well as in crops of which the leaves are used for feed, such as alfalfa, maize and grasses. Possible negative effects on overall leaf size may be avoided by expressing CKI2 under control of an epidermis-specific promoters such as the Blec4 gene promoter of pea (Mandaci and Dobres 1997, Plant Mol. Biol. 34:961–965) or cell layer-specific promoter (Scott Poethig, Plant Cell, 9:1077–1087, 1997).

CKI2 transformants also showed much bigger stomata on the cotyledons than Cdc2a-DN transformants. This effect was not as pronounced on true leaves, probably because of too low levels of expression of CKI2 in these cells. Stomatal opening is the major factor determining gas exchange rates during photosynthesis. Under many environmental conditions, gas exchange is rate-limiting for photosynthetic activity. Large stomata promote gas exchange and thus will increase photosynthetic capacity. Another embodiment of the invention is to express CKI2 or its orthologs from other species under control of a stomata-specific promoter such as Rha1 promoter (Terryn et al., 1993, Plant Cell 5:1761–1769).

In another preferred embodiment, CKI2 or its orthologs, may be expressed under control of a vascular promoter in stems of trees, such as poplar and eucalyptus. Cell size is an important parameter for wood quality and is dependent on environmental conditions (e.g. spring wood versus summer wood). Expression of CKI2 will therefore result in better and more uniform wood quality.

In another preferred embodiment, CKI2 or its orthologs, may be expressed under control of a stem-specific promoter in sugarcane. Modification of cell size in sugarcane stems will change the extractibility and debris production.

In another preferred embodiment, CKI2 or its orthologs, may be expressed under control of a stem (tuber)-specific promoter in potato. The change in cell size will affect tuber composition and shape.

Increased cell size in storage organs such as the sugarbeet root might increase the capacity of the plant to accumulate sugars.

In another preferred embodiment, CKI2 or its orthologs, may be expressed under control of a fruit-specific promoter in agronomically important fruit-bearing trees (e.g. apple, pear) and vegetables (e.g. tomato, melon, cucumber, pepper, strawberry). The change in cell size will alter the relative composition of the different ingredients of the fruit, thereby changing the taste and texture of the fruit.

In another preferred embodiment, CKI2 or its orthologs, may be expressed under control of a seed-specific promoter in oil crops, such as canola, soybean, and sunflower. Changes in cell size will alter the protein and oil composition of the seed, thereby altering its storage capacity and processing properties (e.g. texturing and gel formation). Other modifications in seed composition can be obtained by expressing CKI2 under control of promoters that are specific for a specific seed tissue (e.g. embryo-specific) or developmental stage.

In another preferred embodiment, CKI2 or its orthologs, may be expressed under control of a seed-specific promoter in cereals, such as wheat, barley, rice and maize. Changes in cell size will alter the protein and starch composition of the seed, thereby altering its storage capacity and processing properties (e.g. for brewery and bread-making industry). Other modifications in seed composition can be obtained by expressing CKI2 under control of promoters that are specific for a specific seed tissue (e.g. embryo- or endosperm-specific) or developmental stage.

In another preferred embodiment, CKI2 or its orthologs, may be expressed under a seed or seed-hair specific promoter in cotton. Cotton fiber length is determined by the size of the seed hairs, therefore fiber properties will be altered by CKI2 expression.

In another preferred embodiment, CKI2 or its orthologs, may be expressed under control of a root-specific promoter in vegetable crops such as turnips, sugarbeet, radish, and carrot, in order to alter cell size, shape and/or storage capacity.

CKI2 transformants in *Arabidopsis thaliana* also showed altered leaf shape, leaves being more serrated than in wild-type plants. This phenotype was not seen with Cdc2a-DN in tobacco, suggesting again that there are subtle differences in phenotypes generated by various CDK inhibition methods. This finding is in line with the expression pattern of CKI2 in wild-type leaves, where it is most abundant in the epidermis. The epidermis is believed to play an important role in leaf shape and orientation of cell divisions in the epidermis are also highly regulated (Scott Phoetig, Plant Cell, 9:1077–1087). It is therefore likely that CKI2 has a specific function in the regulation of leaf shape, so that modifying its expression has more pronounced effects on leaf shape than with Cdc2a-DN. Indeed, the rather moderate decrease in CDK activity observed upon CKI2 overexpression, when compared to the reduction of kinase activity in the CDC2aAt.DN overexpressing lines, suggests CKI2 inhibits only CDK activity at a late stage of primordia formation.

Alternatively, CKI2 influences CDK activity in a more subtle way. Increased CKI2 protein levels in transgenic plants indeed correlate with higher levels of Cdc2a protein but the overall CDK kinase activity is moderately decreased (FIG. 11). The Cdc2a protein is thus apparently stabilized and possibly sequestered by CKI2 and its kinase activity inhibited by CKI2.

A preferred embodiment is to express CKI2 under leaf-specific promoters or tissue-specific promoters (e.g. epidermis specific, L2 layer specific) with the aim to create novel leaf shapes in ornamental plants and in vegetables of which the leaves are consumed (e.g. lettuce, cabbage, endive).

Another preferred embodiment is to express CKI2 under petal-specific promoters with the aim to create novel flower shapes in ornamental plants.

In another embodiment the modification of leaf shape may also improve the ability of the plant in capturing light thereby increasing its photosynthesis capacity and crop productivity.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ.

Preferred promoters may contain additional copies of one or more specific regulatory elements, to further enhance expression and/or to alter the spatial expression and/or temporal expression of a nucleic acid molecule to which it is operably connected. For example, copper-responsive, glucocorticoid-responsive or dexamethasone-responsive regulatory elements may be placed adjacent to a heterologous promoter sequence driving expression of a nucleic acid molecule to confer copper inducible, glucocorticoid-inducible, or dexamethasone-inducible expression respectively, on said nucleic acid molecule.

Examples of promoters that may be used in the performance of the invention are provided in Table 4 and 5. The promoters listed in the table are provided for the purposes of exemplification only and the present invention is not to be limited by the list provided therein. Those skilled in the art will readily be in a position to provide additional promoters that are useful in performing the present invention. The promoters listed may also be modified to provide specificity of expression as required.

TABLE 4

EXEMPLARY TISSUE SPECIFIC or TISSUE-PREFERRED PROMOTERS FOR USE IN THE PERFORMANCE OF THE PRESENT INVENTION

| GENE SOURCE | EXPRESSION PATTERN | REFERENCE |
|---|---|---|
| α-amylase (Amy32b) | Aleurone | Lanahan, M.B., et al., Plant Cell 4:203–211, 1992; Skriver, K., et al. Proc. Natl. Acad. Sci. (USA) 88:7266–7270, 1991 |
| Cathepsin β-like gene | Aleurone | Cejudo, F.J., et al. Plant Molecular Biology 20:849–856, 1992. |
| *Agrobacterium rhizogenes* rolB | Cambium | Nilsson et al., Physiol. Plant. 100:456–462, 1997 |
| PRP genes | cell wall | http://salus.medium.edu/mmg/tierney/html |
| AtPRP4 | Flowers | http://salus.medium.edu/mmg/tierney/html |
| Chalene synthase (chsA) | Flowers | Van der Meer, et al., Plant Mol. Biol. 15, 95–109, 1990. |
| LAT52 | Anther | Twell et al Mol. Gen Genet. 217:240–245 (1989) |
| Apetala-3 | Flowers | |
| Chitinase | fruit (berries, grapes, etc) | Thomas et al. CSIRO Plant Industry, Urrbrae, South Australia, Australia; http://winetitles.com.au/gwrdc/csh95-1.html |
| Rbcs-3A | green tissue (eg leaf) | Lam, E. et al., The Plant Cell 2:857–866, 1990.; Tucker et al., Plant Physiol. 113:1303–1308,1992. |
| Leaf-specific genes | Leaf | Baszczynski, et al., Nucl. Acid Res. 16: 4732, 1988. |
| AtPRP4 | Leaf | http://salus.medium.edu/mmg/tierney/html |
| *Chlorella* virus adenine methyltransferase gene promoter | Leaf | Mitra and Higgins, 1994, Plant Molecular Biology 26: 85–93 |
| AldP gene promoter from rice | Leaf | Kagaya et al., 1995, Molecular and General Genetics 248: 668–674 |
| Rbcs promoter from rice or tomato | Leaf | Kyozuka et al., 1993, Plant Physiology 102: 991–1000 |
| Pinus cab-6 | Leaf | Yamamoto et al., Plant Cell Physiol. 35:773–778, 1994. |
| Rubisco promoter | Leaf | |
| Cab (chlorophyll a/b/binding protein | Leaf | |
| SAM22 | senescent leaf | Crowell, et al., Plant Mol. Biol. 18:459–466, 1992. |
| Ltp gene (lipid transfer gene) | | Fleming, et al, Plant J. 2, 855–862. |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang, et al., The Plant J. 3:573–585. |
| PEP carboxylase (PEPC) | Nodule | Pathirana, et al., Plant Mol. Biol. 20: 437–450, 1992. |
| Leghaemoglobin (Lb) | Nodule | Gordon, et al., J. Exp. Bot. 44:1453–1465, 1993. |
| *Tungro bacilliform* virus gene | Phloem | Bhattacharyya-Pakrasi, et al, The Plant J. 4:71–79, 1992. |
| Sucrose-binding protein gene | plasma membrane | Grimes, et al., The Plant Cell 4:1561–1574, 1992. |
| Pollen-specific genes | pollen; microspore | Albani, et al., Plant Mol. Biol. 15:605, 1990; Albani, et al., Plant Mol. Biol. 16: 501, 1991) |
| Zm13 | Pollen | Guerrero et al Mol. Gen. Genet. 224:161–168 (1993) |
| Apg gene | Microspore | Twell et al Sex. Plant Reprod. 6:217–224 (1993) |
| Maize pollen-specific gene | Pollen | Hamilton, et al., Plant Mol. Biol. 18:211–218, 1992. |
| Sunflower pollen-expressed gene | Pollen | Baltz, et al., The Plant J. 2:713–721, 1992. |
| *B. napus* pollen-specific gene | pollen; anther; tapetum | Arnoldo, et al., J. Cell. Biochem., Abstract No. Y101, 204, 1992. |

TABLE 4-continued

EXEMPLARY TISSUE SPECIFIC or TISSUE-PREFERRED PROMOTERS FOR USE IN THE PERFORMANCE OF THE PRESENT INVENTION

| GENE SOURCE | EXPRESSION PATTERN | REFERENCE |
|---|---|---|
| Root-expressible genes | Roots | Tingey, et al., EMBO J. 6:1, 1987. |
| Tobacco auxin-inducible gene | root tip | Van der Zaal, et al., Plant Mol. Biol. 16, 983, 1991. |
| β-tubulin | Root | Oppenheimer, et al., Gene 63:87, 1988. |
| Tobacco root-specific genes | Root | Conkling, et al., Plant Physiol. 93:1203, 1990. |
| *B. napus* G1-3b gene | Root | U.S. Pat. No. 5,401,836 |
| SbPRP1 | Roots | Suzuki et al., Plant Mol. Biol. 21:109–119, 1993. |
| AtPRP1; AtPRP3 | roots; root hairs | http://salus.medium.edu/mmg/tierney/html |
| RD2 gene | root cortex | http://www2.cnsu.edu/ncsu/research |
| TobRB7 gene | root vasculature | http://www2.cnsu.edu/ncsu/research |
| AtPRP4 | leaves; flowers; lateral root primordia | http://salus.medium.edu/mmg/tierney/html |
| Seed-specific genes | Seed | Simon, et al., Plant Mol. Biol. 5:191, 1985; Scofield, et al., J. Biol. Chem. 262: 12202, 1987.; Baszczynski, etal., Plant Mol. Biol. 14:633, 1990. |
| Brazil Nut albumin | Seed | Pearson, et al., Plant Mol. Biol. 18:235–245, 1992. |
| Legumin | Seed | Ellis, et al., Plant Mol. Biol. 10:203–214, 1988. |
| Glutelin (rice) | Seed | Takaiwa, et al., Mol. Gen. Genet. 208: 15–22, 1986; Takaiwa, et al., FEBS Letts. 221:43–47, 1987. |
| Zein | Seed | Matzke et al Plant Mol Biol, 14(3):323–32 1990 |
| NapA | Seed | Stalberg, et al, Planta 199:515–519, 1996. |
| Wheat LMW and HMW glutenin-1 | Endosperm | Mol Gen Genet 216:81–90, 1989; NAR 17:461–2, 1989 |
| Wheat SPA | Seed | Albani et al, Plant Cell, 9:171–184, 1997 |
| Wheat α, β, γ-gliadins | Endosperm | EMBO 3:1409–15, 1984 |
| Barley Itr1 promoter | Endosperm | |
| Barley B1, C, D, hordein | Endosperm | Theor Appl Gen 98:1253–62, 1999; Plant J 4:343–55, 1993; Mol Gen Genet 250:750–60, 1996 |
| Barley DOF | Endosperm | Mena et al, The Plant Journal, 116(1): 53–62, 1998 |
| Blz2 | Endosperm | EP99106056.7 |
| Synthetic promoter | Endosperm | Vicente-Carbajosa et al., Plant J. 13: 629–640, 1998. |
| Rice prolamin NRP33 | Endosperm | Wu et al, Plant Cell Physiology 39(8) 885–889, 1998 |
| Rice α-globulin Glb-1 | Endosperm | Wu et al, Plant Cell Physiology 39(8) 885–889, 1998 |
| Rice OSH1 | Embryo | Sato et al, Proc. Natl. Acad. Sci. USA, 93: 8117–8122, 1996 |
| Rice a-globulin REB/OHP-1 | Endosperm | Nakase et al. Plant Mol. Biol. 33: 513–522, 1997 |
| Rice ADP-glucose PP | Endosperm | Trans Res 6:157–68, 1997 |
| Maize ESR gene family | Endosperm | Plant J 12:235–46, 1997 |
| Sorgum γ-kafirin | Endosperm | PMB 32:1029–35, 1996 |
| KNOX | Embryo | Postma-Haarsma et al, Plant Mol. Biol. 39:257–71, 1999 |
| Rice oleosin | embryo and aleuron | Wu et al, J. Biochem., 123:386, 1998 |
| Sunflower oleosin | seed (embryo and dry seed) | Cummins, et al., Plant Mol. Biol. 19: 873–876, 1992 |
| LEAFY | shoot meristem | Weigel et al., Cell 69:843–859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| Stigma-specific genes | Stigma | Nasrallah, et al., Proc. Natl. Acad. Sci. USA 85: 5551, 1988; Trick, et al., Plant Mol. Biol. 15: 203, 1990. |
| Class I patatin gene | Tuber | Liu et al., Plant Mol. Biol. 153:386–395, 1991. |
| PCNA rice | Meristem | Kosugi et al, Nucleic Acids Research 19:1571–1576, 1991; Kosugi S. and Ohashi Y, Plant Cell 9:1607–1619, 1997. |
| Pea TubA1 tubulin | Dividing cells | Stotz and Long, Plant Mol. Biol. 41, 601–614. 1999 |

TABLE 4-continued

EXEMPLARY TISSUE SPECIFIC or TISSUE-PREFERRED PROMOTERS FOR USE IN THE PERFORMANCE OF THE PRESENT INVENTION

| GENE SOURCE | EXPRESSION PATTERN | REFERENCE |
|---|---|---|
| *Arabidopsis* cdc2a | cycling cells | Chung and Parish, FEBS Lett, 3;362(2):215–9, 1995 |
| *Arabidopsis* Rop1A | Anthers; mature pollen + pollen tubes | Li et al. 1998 Plant Physiol 118, 407–417. |
| *Arabidopsis* AtDMC1 | Meiosis-associated | Klimyuk and Jones 1997 Plant J. 11, 1–14. |
| Pea PS-IAA4/5 and PS-IAA6 | Auxin-inducible | Wong et al. 1996 Plant J. 9, 587–599. |
| Pea farnesyltransferase | Meristematic tissues; phloem near growing tissues; light- and sugar-repressed | Zhou et al. 1997 Plant J. 12, 921–930 |
| Tobacco (*N. sylvestris*) cyclin B1; 1 | Dividing cells / meristematic tissue | Trehin et al. 1997 Plant Mol. Biol. 35, 667–672. |
| *Catharanthus roseus* Mitotic cyclins CYS (A-type) and CYM (B-type) | Dividing cells / meristematic tissue | Ito et al. 1997 Plant J. 11, 983–992 |
| *Arabidopsis* cyc1At (=cyc B1; 1) and cyc3aAt (A-type) | Dividing cells / meristematic tissue | Shaul et al. 1996 Proc. Natl. Acad. Sci. U.S.A 93, 4868–4872. |
| *Arabidopsis* tef1 promoter box | Dividing cells / meristematic tissue | Regad et al. 1995 Mol. Gen. Genet. 248, 703–711. |
| *Catharanthus roseus* cyc07 | Dividing cells / meristematic tissue | Ito et al. 1994 Plant Mol. Biol. 24, 863–878. |

TABLE 5

EXEMPLARY CONSTITUTIVE PROMOTERS FOR USE IN THE PERFORMANCE OF THE PRESENT INVENTION

| GENE SOURCE | EXPRESSION PATTERN | REFERENCE |
|---|---|---|
| Actin | Constitutive | McElroy et al, Plant Cell, 2:163–171, 1990 |
| CAMV 35S | Constitutive | Odell et al, Nature, 313:810–812, 1985 |
| CaMV 19S | Constitutive | Nilsson et al., Physiol. Plant. 100:456–462, 1997 |
| GOS2 | Constitutive | de Pater et al, Plant J Nov; 2(6):837–44, 1992 |
| Ubiquitin | Constitutive | Christensen et al, Plant Mol. Biol. 18: 675–689, 1992 |
| Rice cyclophilin | Constitutive | Buchholz et al, Plant Mol Biol. 25(5): 837–43, 1994 |
| Maize H3 histone | Constitutive | Lepetit et al, Mol. Gen. Genet. 231:276–285, 1992 |
| Actin 2 | Constitutive | An et al, Plant J. 10(1); 107–121, 1996 |

In each of the preceding embodiments of the present invention, CKI2 or a homologue, analogue, or derivative thereof, is expressed under the operable control of a plant-expressible promoter sequence. As will be known those skilled in the art, this is generally achieved by introducing a genetic construct or vector into plant cells by transformation or transfection means. The nucleic acid molecule or a genetic construct comprising same may be introduced into a cell using any known method for the transfection or transformation of said cell. Wherein a cell is transformed by the genetic construct of the invention, a whole organism may be regenerated from a single transformed cell, using methods known to those skilled in the art.

Means for introducing recombinant DNA into plant tissue or cells include, but are not limited to, transformation using $CaCl_2$ and variations thereof, in particular the method described by Hanahan (*J. Mol. Biol.* 166, 557–560, 1983), direct DNA uptake into protoplasts (Krens et al, *Nature* 296: 72–74, 1982; Paszkowski et al, *EMBO J.* 3.2717–2722, 1984), PEG-mediated uptake to protoplasts (Armstrong et al, *Plant Cell Reports* 9: 335–339, 1990) microparticle bombardment, electroporation (Fromm et al., *Proc. Natl. Acad. Sci.* (*USA*) 82:5824–5828, 1985), microinjection of DNA (Crossway et al., *Mol. Gen. Genet.* 202:179–185, 1986), microparticle bombardment of tissue explants or cells (Christou et al, *Plant Physiol* 87: 671–674, 1988; Sanford, *Particulate Science and Technology* 5: 27–37, 1987), vacuum-infiltration of tissue with nucleic acid, or in the case of plants, T-DNA-mediated transfer from *Agrobacterium* to the plant tissue as described essentially by An et al. (*EMBO J.* 4.277–284, 1985), Herrera-Estrella et al. (*Nature* 303: 209–213, 1983a; *EMBO J.* 2: 987–995, 1983b; In: Plant Genetic Engineering, Cambridge University Press, N.Y., pp 63–93, 1985), or in planta method using *Agrobacterium tumefaciens* such as that described by Bechtold et al., (*C.R. Acad. Sci.* (Paris, *Sciences de la vie/Life Sciences*) 316: 1194–1199, 1993) or Clough et al (*Plant J.* 16: 735–743, 1998) amongst others.

A whole plant may be regenerated from the transformed or transfected cell, in accordance with procedures well known in the art. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The generated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques.

The generated transformed organisms contemplated herein may take a variety of forms. For example, they may be chimeras of transformed cells and non-transformed cells; clonal transformants (e.g., all cells transformed to contain the expression cassette); grafts of transformed and untransformed tissues (e.g., in plants, a transformed root stock grafted to an untransformed scion).

A further aspect of the present invention clearly provides the genetic constructs and vectors designed to facilitate the introduction and/or expression and/or maintenance of the CKI2 protein-encoding sequence and promoter into a plant cell, tissue or organ.

In addition to the CKI2 protein-encoding sequence and promoter sequence, the genetic construct of the present invention may further comprise one or more terminator sequences. The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants. Examples of terminators particularly suitable for use in the genetic constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays zein* gene terminator sequence, the rbcs-1A gene terminator, and the rbcs-3A gene terminator sequences, amongst others.

Those skilled in the art will be aware of additional promoter sequences and terminator sequences which may be suitable for use in performing the invention. Such sequences may readily be used without any undue experimentation.

The genetic constructs of the invention may further include an origin of replication sequence which is required for maintenance and/or replication in a specific cell type, for example a bacterial cell, when said genetic construct is required to be maintained as an episomal genetic element (eg. plasmid or cosmid molecule) in said cell. Preferred origins of replication include, but are not limited to, the f1-ori and co/E1 origins of replication.

The genetic construct may further comprise a selectable marker gene or genes that are functional in a cell into which said genetic construct is introduced. As used herein, the term "selectable marker gene" includes any gene which confers a phenotype on a cell in which it is expressed to facilitate the identification and/or selection of cells which are transfected or transformed with a genetic construct of the invention or a derivative thereof. Suitable selectable marker genes contemplated herein include the ampicillin resistance (Amp$^r$), tetracycline resistance gene Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene, amongst others.

The present invention is applicable to any plant, in particular a monocotyledonous plants and dicotyledonous plants including a fodder or forage legume, companion plant, food crop, tree, shrub, or ornamental selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp. *Vitis vinifera*, *Watsonia pyramidata*, *Zantedeschia aethiopica*, *Zea mays*, rice, straw, amaranth, onion, asparagus, sugar cane, soybean, sugarbeet, sunflower, carrot, celery, cabbage, canola, tomato, potato, lentil, flax, broccoli, oilseed rape, cauliflower, brussel sprout, artichoke, okra, squash, kale, collard greens, and tea, amongst others, or the seeds of any plant specifically named above or a tissue, cell or organ culture of any of the above species.

Preferably, the plant is a plant that is capable of being transfected or transformed with a genetic sequence, or which is amenable to the introduction of a protein by any art-recognised means, such as microprojectile bombardment, microinjection, *Agrobacterium*-mediated transformation, protoplast fusion, protoplast transformation, in planta transformation, or electroporation, amongst others.

This aspect of the invention further extends to plant cells, tissues, organs and plants parts, propagules and progeny plants of the primary transformed or transfected cells, tissues, organs or whole plants that also comprise the introduced isolated nucleic acid molecule operably under control of the cell-specific, tissue-specific or organ-specific promoter sequence and, as a consequence, exhibit similar phenotypes to the primary transformants/transfectants or at least are useful for the purpose of replicating or reproducing said primary transformants/transfectants.

As ICKs are known to inhibit CDK kinase activity and CDKs are known to be required for normal cell division, it can be envisaged that downregulation of ICK expression in whole plants or parts thereof will result in enhanced cell division in said whole plant or said part thereof. Another aspect of downregulation of ICK expression is that under such conditions differentiation of cells will be delayed, i.e. cells will retain the competence to divide for a longer time. The net result will thus be an increase in cell number and thus, an increase of the size of the whole plant or a part thereof. In mammalians, most, if not all, ICKs are required to establish and/or maintaining the differentiated cell state as described for Ink-4-type ICKs (Hannon and Beach 1994, Nature 371, 257–61), p21 Cip 1 (Beier et al. 1999, J. Biol. Chem. 274, 30273–79; Otten et al., Cell Growth Differ. 8, 1151–60; Prowse et al. 1997, J. Biol. Chem. 272, 1308–14), p27Kip1 (Levine et al. 2000, Dev. Biol. 219, 299–314; Perez-Juste and Arande 1999, J. Biol. Chem. 274, 5026–31) and p57Kip2 (Iovicu and McAvoy, Mech. Dev. 86, 165–69; Mech. Dev. 86, 165–69; Matauoka et al. 1995, Genes Dev. 9, 650–62).

Downregulation of ICK expression in plant cells naturally undergoing extensive endoreduplication is expected to enhance this process as well as to extend the process by delaying differentiation of said endocycling cells. By virtue of being linked to cell expansion and metabolic activity, endoreduplication is generally considered as an important factor for increasing yields (Traas et al 1998). As grain endosperm development initially includes extensive endoreduplication (Olsen et al. 1999), enhancing, promoting or stimulating this process is likely to result in increased grain yield. Enhancing, promoting or stimulating cell division curing seed development as described supra is an alternative way to increase grain yield. Those skilled in the art will be aware that grain yield in crop plants is largely a function of the amount of starch produced in the endosperm of the seed. The amount of protein produced in the endosperm is also a contributing factor grain yield. In contrast, the embryo and aleurone layers contribute little in terms of the total weight of the mature grain.

Accordingly, another embodiment of the invention provides a method for modifying plant cell size and/or cell number which comprises downregulation of expression in a plant cell of a cyclin-dependent kinase inhibitor. Plant cell size and/or cell number may also be modified by lowering the level of active cyclin-dependent kinase inhibitor gene products or of cyclin-dependent kinase inhibitor gene produce activity.

Another method is provided for enhancing and/or extending the process of endoreduplication in plant cells which comprises downregulation of expression in a plant cell of a cyclin-dependent kinase inhibitor. Enhancing and/or extending the process of endoreduplication in plant cells may also be obtained by lowering the level of active cyclin-dependent kinase inhibitor gene products or of cyclin-dependent kinase inhibitor gene product activity.

Those skilled in the art will be aware that grain yield in crop plants is largely a function of the amount of starch produced in the endosperm of the seed. The amount of protein produced in the endosperm is also a contributing factor to grain yield. In contrast, the embryo and aleurone layers contribute little in terms of the total weight of the mature grain. By virtue of being linked to cell expansion and metabolic activity, endoreduplication is generally considered an important factor for increasing yield (Traas, J., Hulskamp., M. Gendreau, E., and Hofte, H. (1998), Endoreduplication and development: rule without dividing? Curr. Opin. Plant Biol 1: 498–503). As grain endosperm development initially includes extensive endoreduplication (Olsen, O. A., Linnestad, C., and Nichols, S. E. (1999), Development biology of the cereal endosperm. Trends Plant Sci. 4: 253–257), enhancing, promoting or stimulating this process is likely to result in increased grain yield. Enhancing, promoting or stimulating cell division during seed development as described supra is an alternative way to increase grain yield.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe (1998—WO9836083), Lowe et al. (1989—WO9836083), Lederer et al. (1999—WO9915682) or Wang et al. (1999—WO9953050). Genetic constructs aimed at silencing gene expression may have the nucleotide sequence of said gene (or one or more parts thereof) contained therein a sense and/or antisense orientation relative to the promoter sequence. Another method to downregulate gene expression comprises the use of ribozymes, e.g. as described in Atkins et al. 1994 (WO9400012), Lenee et al. 1995 (WO9503404), Lutziger et al. 2000 (WO0000619), Prinsen et al. 1997 (WO9713865) and Scott et al. 1997 (WO9738116).

Modulating, including lowering, the level of active gene products or of gene product activity can be achieved by administering or exposing cells, tissues, organs or organisms to said gene product, a homologue, analogue, derivative and/or immunologically active fragment thereof. Immunomodulation is another example of a technique capable of downregulation levels of active gene product and/or gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an agonist of said gene product or the activity thereof. Such agonists include proteins (comprising e.g. kinases and proteinases) and chemical compounds identified according to the current invention as described supra.

As used herein "ortholog" of a protein means a homologue, analogue, derivative and/or immunologically active fragment of said protein.

"Homologues" of a protein of the invention are those peptides, oligopeptides, polypeptides, proteins and enzymes which contain amino acid substitutions, deletions and/or additions relative to the said protein with respect to which they are homologue, without altering one or more of its functional properties, in particular without reducing the activity of the resulting. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic movement, antigenicity, propensity to form or break α-helical structures or β-sheet structures, and so on. An overview of physical and chemical properties of amino acids is given in Table 3.

TABLE 3

Properties of naturally occurring amino acids.

| Charge properties/ hydrophobicity | Sid Group | Amino Acid |
|---|---|---|
| nonpolar hydrophobic | aliphatic | ala, ile, leu, val |
| | aliphatic, S-containing | met |
| | aromatic | phe, trp |
| | imino | pro |
| polar uncharged | aliphatic | gly |
| | amide | asn, gln |
| | aromatic | try |
| | hydroxyl | ser, thr |
| | sulfhydryl | cys |
| positively charged | basic | arg, his, lys |
| negatively charged | acidic | asp, gly |

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1–10 amino acid residues, and deletions will range from about 1–20 residues. Preferably, amino acid substitutions will comprise conservative amino acid substitutions, such as those described supra.

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase, protein A, maltose-binding protein, dihydrofolate reductase, Tag•100 epitope (EETARFQPQPGPGYRS) (SEQ ID NO:42), c-myc epitope (EQKLISEEDL)(SEQ ID NO:43), FLAG®-epitope (DYKDDDK) (SEQ ID NO:44), lacZ, CMP (calmodulin-binding peptide), HA epitope (YPYDVPDYA) (SEQ ID NO:45), protein C epitope (EDQVDPRLIDGK) (SEQ ID NO:46) and VSV epitope (YTDIEMNRLGK) (SEQ ID NO:47).

Deletional variants of a protein of the invention are characterized by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols.

"Analogues" of a protein of the invention are defined as those peptides, oligopeptides, polypeptides, proteins and enzymes which are functionally equivalent to said protein with respect to which they are analogous. Analogous of said protein will preferably exhibit like.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition a derivative may comprise one or more non-amino acid substitutents compared to the amino acid sequence of a naturally-occurring form of said polypeptide, for example a reporter molecule or other ligand, covalently or non-covalently bound to the amino acid sequence such as, for example, a reporter molecule which is bound thereto facilitate its detection.

With "immunologically active" is meant that a molecule or specific fragments thereof such as epitopes or happens are recognized by, i.e. bind to antibodies.

The following examples further illustrate the invention.

EXAMPLES

Unless stated otherwise in the examples, all recombinant DNA techniques are performed according to protocols as described in Sambrook et al. (1989), Molecular Cloning: A Laboratory Manual. Cold Spring Harbor Laboratory Press, NY or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, jointly published by BIOS Scientific Publications Ltd (UK) and Blackwell Scientific Publications (UK).

Example 1

Identification of Putative Cyclin-Dependent Kinase Inhibitors

For the identification of CKIs a two hybrid system based on GAL4 recognition sites to regulate the expression of both his3 and lacZ reporter genes was used to identify CDC2aAt-interacting of proteins. The bait used for the two-hybrid screening was constructed by inserting the CDC2aAt coding region into the pGBT9 vector (Clontech). The insert was created by PCR using the CDC2aAt cDNA as template. Primers were designed to incorporate EcoRI restriction enzyme sites. The primers used were 5'-CGAGATCTGMT-TCATGGATCAGTA-3' (SEQ ID NO: 7) and 5'-CGAGATCTGMTTCCTAAGGCATGCC-3' (SEQ ID NO: 8). The PCR fragment was cut with EcoRI and cloned into the EcoRI site of pGBT9, resulting in the pGBTCDC2A plasmid. For the screening a GAL4 activation domain cDNA fusion library was used constructed from *Arabidopsis thaliana* cell suspension cultures. This library was constructed using RNA isolated from cells harvested at 20 hours, 3, 7 and 10 days after dilution of the culture in new medium. These time point correspondent to cells from the early exponential growth phase to the late stationary phase. mRNA was prepared using Dynabeads oligo(dT)$_{25}$ according to the manufacturer's instructions (Dynal). The GAL4 activation domain cDNA fusion library was generated using the HybriZAP™ vector purchased with the HybriZAP™ Two-Hybird cDNA Gigapack cloning Kit (Stratagene) following the manufacturer's instructions. The resulting library contained approximately $3.10^6$ independent plaque-forming units, with an average insert size of 1 Kb.

For the screening a 1-liter culture of the *Saccharomyces cerevisiae* strain HF7c (MAT$_a$ ura3-52 his3-200 ade2-101 lys2-801 trp1-901 leu2-3, 112 gal4-542 gal80-538 LYS2:: GAL1$_{UAS}$-GAL1$_{TATA}$-HIS3 URA3::GAL4$_{17mers(3x)}$-CyC1$_{TATA}$-LacZ) was cotransformed with 400 µg pGBTCDC2A, 500 µg DNA of the library, and 40 mg salmon sperm carrier DNA using the lithium acetate method (Gietz et al. 1992, Nucleic Acids Res. 20, 1425). To estimate the number of independent cotransformants, ¹/₁₀₀₀ of the transformation mix was plated on Leu⁻ and Trp⁻ medium. The rest of the transformation mix was plated on medium to select for histidine prototrophy (Trp⁻, Leu⁻, His⁻). Of a total of approximately $1.2 \times 10^7$ independent transformants 1200 colonies grew after 3 days of incubation at 30° C. The colonies larger than 2 mm were streaked on histidine-lacking medium supplemented with 10 mM 3-amino-1,2,4-triazole (Sigma). Two-hundred-fifty colonies capable of growing under these conditions were tested for β-galactosidase activity as described (Breedon and Nasmyth 1995, Cold Spring Harbor Symp. Quant. Biol. 50, p643–650), and 153 turned out to be His⁺ and LacZ⁺. Plasmid DNA was prepared from the positive clones and sequenced.

The plasmids pGADLDV39, pGADLDV66, and pGADLDV159 contained a protein (designated LDV39, LDV66, and LDV159, respectively) of which the last 23 amino-acids showed significant homology to the human CKIs p21$^{cip1}$ and p27$^{kip1}$. The LDV159 clone was identical to ICK1 (GenBank accession number U94772 as published by Wang in Nature 386 (1997), 451–452). The two other clones were novel and encoded proteins only distantly related to ICK1 (Table 1). The LDV39 gene was 622 bp long, consisting of 423 bp coding region and 199 bp 3' UTR (excluding the poly-A tail). The LDV66 gene was 611 bp long, consisting of 379 bp coding region and 232 bp 3' UTR (excluding the poly-A tail). The specificity of the interaction between LDV39, LDV66, and LDV159 was verified by the retransformation of yeast with pGBTCDC2A and pGADLDV39/pGADLDV66/pGADLDV159. As controls, pGBTCDC2A was cotransformed with a vector containing only the GAL4 activation domain (pGAD424); and the pGADLDV39/pGADLDV66/pGADLDV159 vectors were cotransformed with a plasmid containing only the GAL4 DNA binding domain (pGBT9). Transformants were plated on medium with or without histidine. Only transformants containing both pGBTCDC2A and pGADLDV39, pGADLDV66, ot pGADLDV159 were able to grow in the absence of histidine.

Example 2

LDV66, LDV39 and LDV159 Bind CDC2aAt, not CDC2bAt

The pGBTCDC2B vector encoding a fusion protein between the C-terminus of the GAL4 DNA-binding domain and CDC2bAt was constructed by cloning the full length coding region of CDC2bAt into the pGBT9 vector. pGBTCDC2B was transformed with pGADLDV66/pGADLDV39/pGADLDV159 in the HF7c yeast and cotransformants were plated on medium with or without histidine. As control, pGBTCDC2A was transformed with pGADLDV66/pGADLDV39/pGADLDV159. In contrast to the transformants containing the pGBTCDC2A vector were cotransformants containing the pGBTCDC2B vector unable to grow in the absence of histidine. This demonstrates that the LDV66, LDV39, LDV159 proteins associate with CDC2aAt but not with CDC2bAt.

Example 3

Isolation of FL39 and FL66 Sequences

Since the LDV39 and LDV66 clones encode partial proteins, lacking their amino-terminal part, a flower cDNA library obtained from the ABRC stock centre (library stock number CD4-6) was screened. In total 50.000 plaque forming units were hybridised using a fluorescein-labelled LDV39 or LDV66 probe according to the manufacturer's protocol (Amersham) using a hybridisation temperature of 60° C. After 16 hours hybridisation the filters were washed for 15 min using 2×SSC; 0.1×SDS, and 15 min using 1×SSC; 0.1×SDS. The signals were detected using the CDP-star detection module. according to the manufacturer's protocol (Amersham). The signals were revealed by autoradiography. For both genes only one positive signal was identified among the 50.000 phages, suggesting low mRNA levels of LDV39 and LDV66 in flowers. Phages corresponding to the positive signals were eluted from gel and purified by two additional hybridisation rounds, using 1.000 and 50 plaque forming units in the second and third hybridisation round, respectively. The hybridisation conditions were similar as those described above. After pure phages were obtained, DNA was extracted and sequenced. The positive clones were denominated FL39 and FL66, corresponding to longer clones of LDV39 and LDV66, respectively.

The FL39 clone is 932 bp long and contains an ORF encoding a protein of 209 amino acids with a calculated molecular mass of 24 kDa. In its 3' UTR a poly-adenylation signal can be recognised. The amino-terminal part of the FL39 protein contains a repeated motif of 11 amino acids (VRRRD/ExxxVEE; SEQ ID NO: 33). This motif is not found in any other protein in the databanks and its significance in unknown. The FL39 protein also contains a putative nuclear localization signal (amino acids 23–26) and a PEST-rich region (amino acids 71–98; P$_{ESTFIND}$ score+15.5). These sequences, rich in proline, glutamic acid, serine and proline, are characteristically present in unstable proteins (Rogers et al., 1986, Science 234, 364–368).

The FL66 sequence does not contain an in frame stopcodon, and may therefore not be full length. The FL66 clone is 875 bp long and bears an ORF of 216 amino acids, encoding a protein of 24 kD. No nuclear localization signal or PEST domains are present.

The genomic organisation of the FL39, FL66 and LDV159 clones was tested by DNA gel blot analysis. *A.* thaliana C24 DNA digested with three different restriction enzymes was probed with fluorescein-labelled prepared from the LDV159, FL39, or FL66 sequences according to the manufacturer's protocol (Amersham). Hybridisations were performed at 60° C. After 16 hours hybridisation the membranes were washed for 15 min using 2×SSC; 0.1× SDS, and 15 min using 1×SSC; 0.1×SDS. The signals were detected using the CDP-star detection module according to the manufacturer's protocol (Amersham). The signals were revealed by autoradiography. For LDV159 and FL39, only one hybridisation band was noticed for every digest. For FL66 an additional weak band was observed. The low intensity bands did not corespondent with any of the bands found for LDV159 or FL39, suggesting the presence of an additional FL66 related gene. We conclude that there are at least four different CKI proteins present in A. thaliana.

Example 4

The Arabidopsis thaliana CKIs Bind Exclusively to CDC2aAt In Vivo

The binding specificity of the FL39 and FL66 proteins towards CDC2aAt and CDC2bAt was studied using the two-hybrid system. The FL39 and FL66 coding regions were cloned in frame with the GAL4 activation-domain in the pGAD424 vector (Clontech). The FL39 coding region was amplified using the 5'-GGGAATCCATGGGCGGCGGT-TAGGAGAAG-3' (SEQ ID NO: 9) and 5'-GGCGGATC-CCGTCTTCTTCATGGATTC-3' (SEQ ID NO: 10) primers. The FL66 coding region was amplified using the 5'-GGC-GAATCCATGGAAGTCTCTMAGCAAC-3' (SEQ ID NO: 11) and 5'-GGCGGATCCTTTTGAACTTCATG-GTTTGAC-3' (SEQ ID NO: 12) primers. The FL66 amplified coding sequence encloses a protein starting at the methionine at amino-acid position 11, therefore not including the first 10 amino-acids encoded by the FL66 clone. The PCR fragments were cut with EcoR1 and BamH1 and cloned into the EcoR1 and BamH1 sites of pGAD424, resulting in the pGADFL39 and pGADFL66 clones. These plasmids were transformed into the HF7c yeast in combination with pGBTCDC2A or pGBTCDC2B. The pGBTCDC2B plasmid, encoding a fusion protein between the C-terminus of the GAL4 DNA-binding domain and CDC2bAt was obtained by cloning the full length coding of CDC2bAt into the pGBT9 vector (Clontech).

In contrast to the transformants containing the pGBTCDC2A vector were the transformants containing the pGBTCDC2B vector unable to grow in the absence of histidine. This demonstrates that the FL39 and FL66 proteins exclusively associate with CDC2aAt.

Example 5

Generation of FL39 and FL66 Specific Antibodies

To obtain sufficient amount of FL66 and FL39 proteins for immunization, the FL39 and FL66 coding sequences were cloned into pET vectors. The genes cloned in these vectors are expressed under the control of the strong inducible T7 promoter in Escherichia coli (Studier et al., 1986, J. Mol. Biol., 189, p113–130). The coding region of FL39 and FL66 were amplified by PCR technique. The FL66 amplified coding sequence encloses a protein starting at the methionine at amino-acid position 11, therefore not including the first 10 amino-acids encoded by the FL66 clone. Primers used to amplify FL39 were 5'-TAGGAGCATATGGCG-GCGG-3' (SEQ ID NO: 29) and 5'-ATCATCGAATTCT-TCATGGATTC-3' (SEQ ID NO: 30). Primers used to amplify FL66 were 5'-ATATCAGCGCCATGGAAGTC-3' (SEQ ID NO: 31) and 5'-GGAGCTGGATCCTTTTG-GAATTCATGG-3' (SEQ ID NO: 32).

The obtained FL39 PCR fragment was purified, and cut with NdeI and EcoRI restriction enzymes. This fragment was cloned into the NdeI and EcoRI sites of pET derivative pRK172 (McLeod et al., 1987, EMBO J. 6, p729–736). The obtained FL66 PCR fragment was purified, cut with NcoI and BamHI and cloned into the NcoI and BamHI sites of pET21d. FL66pET21 d was transformed in E. coli BL21 (DE3). FL39pRK172 was co-transformed in E. coli BL21 (DE3) with pSBETa (Schenk et al., 1995 Biotechniques 19, p 196–200). PSBETa encoded the tRNA$^{UCU}$ that is low abundant tRNA in E. coli, corresponding to codons AGG and AGA (arginine). Because of the presence of an AGG AGA AGA sequence (SEQ ID NO:48) (Arg 5, Arg 6, Arg 7) at the beginning of FL39 coding sequence, an increase of the tRNA$^{UCU}$ pool of E. coli is necessary for the translation of FL39. The FL66pET21d/BL21(DE3) and FL39pRK172, pSBETa/BL21(DE3) E. coli recombinant strains were grown in LB medium, supplemented respectively with 50 µg/ml ampicillin and 50 µg/ml ampicilline; 25 µg/ml kanamycine. The cells were grown at 37° C. until the density of the culture reached an $A_{600nm}$=0.7. At this time point, 0.4 mM IPTG was added to induce the recombinant protein production. Cells were collected 3 hours later by centrifugation. The bacterial pellet from 250 ml culture was suspended in 10 ml lysis buffer (Tris.HCl pH7.5, 1 mM DTT, 1 mM EDTA, 1 mM PMSF and 0.1% TritonX-100) and submitted to three freeze/thaw cycles before sonication. Cell lysate was clarified by centrifugation 20 minutes at 8000 rpm. The pellet was collected, was suspended again in extraction buffer, the resulting suspension sonicated, and pellet collected by centrifugation 20 minutes at 8000 rpm. A third wash was performed the same way with Tris extraction buffer+1 M NaCl and a fourth wash with Tris extraction buffer. After the different washing steps, the pellet contains FL66 or FL39 protein at 90% homogeneity. The pellets were suspended in Laemli loading buffer (Laemmli, 1970, Nature 277, p 680–681) and FL66 and FL39 were further purified by SDS/12% polyacrylamide gel electrophoresis. The gel was stained in 0.025% coomassie brilliant blue R250 in water and destained in water. The strong band co-migrating at the 31 kDa molecular weight marker position was cut out of the gel with a scalpel. The polyacrylamide fragments containing FL66 or FL39 were lyopyhilized and reduced into powder. The rabbit immunization was performed in complete Freund adjuvant, sub-cutaneous, with these antigen preparations. One injection corresponded to 100 µg of protein. The boosting injections were performed with non-complete Freund adjuvant, sub-cutaneous. The obtained sera detected bands of the expected size in protein extracts prepared from 2-day-old actively dividing cell cultures. No signals were observed using the pre-immune sera.

Example 6

Inhibition of Kinase Activity by FL66

The FL66pET/B11 (DE3) strain was used for the production of recombinant FL66. The inclusion bodies containing FL66 were collected and washed as described above. The recombinant FL66 protein was solubilized in 50 mM Tris.HCl pH7.6, 6M urea and kept on ice for 1 hour. Refolding of the FL66 protein was performed by removing urea on a sephadex G25 gel filtration column, equilibrated in 50 mM Tris.HCl pH7.6, 400 mM NaCl. The collected fractions were centrifuged and the supernatant was used for the inhibition assay. CDK complexes from *A. thaliana* were purified on p13$^{suc1}$ sepharose beads, starting from 100 µg of total protein extract prepared from a 2-day-old cell suspension culture. The FL66 protein was added to these purified complexes at a final concentration of 10 nM, 100 nM, 1 µM and 10 µM. After incubation during 1 hour on ice the CDK activity was measured using histone H1 as substrate, according to Azzi et al. (1992, Eur. J. Biochem., 203, 353–380). When compared to a control sample (without addition of FL66), the activity was found to be 82% of the control after addition of 10 nM of FL66, 74% after addition of 100 nM, 56% after addition of 1 µM, and 12% after addition of 10 µM of FL66. Addition of 30 µM of bovine serum albumin by comparison gives only a non-specific decrease to 70% of the control activity.

The FL66 preparation was also added to *A. thaliana* CDK fraction bound to p13$^{suc1}$ beads, prior to washing of these beads. The kinase activity dropped to 81% and 35% of the control with a concentration of 0.1 µM and 10 µM of FL66, respectively.

Example 7

The *Arabidopsis thaliana* CKI FL66 Associates Exclusively with CDC2aAt In Vitro Purified recombinant FL66 protein (prepared as described as in previous Example 6 was coupled to CNBr-activated Sepharose 4B (Pharmacia) at a concentration of 5 mg/ml of gel according to the manufacturer's instructions. Protein extracts were prepared from a 2-day-old cell suspension culture of *A. thaliana* Col-O in homogenisation buffer (HB) containing 50 mM Tris-HCl (pH 7.2), 60 mM β-glycerophosphate, 15 mM nitrophenyl phosphate, 15 mM EGTA, 15 mM MgCl$_2$, 2 mM dithiothreitol, 0.1 mM vanadate, 50 mM NaF, 20 µg/ml leupeptin, 20 µg/ml aprotinin, 20 µg/ml soybean trypsin inhibitor (SBTI), 100 µM benzamidine, 1 mM phenylmethylsulfonylfluoride, and 0.1% Triton X-100. Two-hundred µg protein extract in a total volume of 100 µl HB was loaded on 50 µl 50% (v/v) FL66-Sepharose or control Sepharose beads, and incubated on a rotating wheel for 2 h at 4° C. The unbound proteins were collected for later analysis. The beads-bound fractions were washed 3 times with HB. Beads were resuspended in 30 µl SDS-loading buffer and boiled. The supernatants (beads bound fractions) and 10 µl of the unbound fractions were separated on a 12.5% SDS-PAGE gel and electroblotted on nitrocellulose membrane (Hybond-C$^+$; Amersham). Filters were blocked overnight with 2% milk in phosphate buffered saline (PBS), washed 3 times with PBS, probed for 2 h with specific antibodies for CDC2aAt (⅕₀₀₀ dilution) or CDC2bAt (½₅₀₀ dilution) in PBS containing 0.5% Tween-20 and 1% albumin, washed for 1 h with PBS with 0.5% Tween-20, incubated for 2 h with peroxidase-conjugated secondary antibody (Amersham), and washed for 1 h with PBS containing 0.5% Tween 20. Protein detection was done by the chemoluminescent procedure (Pierce).

Western blotting revealed that the a significant fraction of CDC2aAt retained on the FL66-Sepharose beads, but not on the control beads, demonstrating the in vitro interaction between FL66 and CDC2aAt. In contrast, the CDC2bAt protein did not retain on the FL66-Sepharose beads but was found back in the unbound fraction. These results demonstrate the specificity of the FL66 protein for CDC2aAt.

Example 8

Expression of CKIs at Different Time-Points in an Asynchronous Cell Suspension Culture of *Arabidopsis thaliana*

The expression levels of the different *A. thaliana* CKI genes (FL39, FL66, and LDV159) at different time-points during the cultivation of a *A. thaliana* cell culture were studied by reverse-transcriptase polymerase chain reaction (RT-PCR) technology. Four time-points were considered, representing the cell culture at different growth phases: day 1 (lag phase), day 5 (exponential growth phase), day 8 (beginning of the stationary phase), and day 12 (late stationary phase). Total RNA of cells harvested at these time-points was extracted using the Trizol reagent (Gibco BRL). 75 µg of this total RNA preparation was used for mRNA extraction using Dynabeads oligoT25 (Dynal). This mRNA was used to prepare cDNA using the universal riboclone cDNA synthesis system (Promega). Five ng of cDNA was subsequently used for RT-PCR, using 300 ng of each of the appropriate forward and reverse primers, 160 µM of dNTPs, 10 µl of PCR buffer, and 0.8 µl of Taq polymerase (Promega). The used primers were 5'-CGGCTCGAG-GAGAACCACAAACACGC-3' (SEQ ID NO: 13) and 5'-CGAAACTAGTTAATTACCTCAAGGAAG-3' (SEQ ID NO: 14) for FL39; 5'-GATCCCGGGCGATATCAGCGT-CATGG-3' (SEQ ID NO: 15) and 5'-GATCCCGGGT-TAGTCTGTTAACTCC-3' (SEQ ID NO: 16) for FL66; 5'-GCAGCTACGGAGCCGGAGAATTGT-3' (SEQ ID NO: 17) and 5'-TCTCCTTCTCGAAATCGAAATTGTACT-3' (SEQ ID NO: 18) and for LDV159. The PCR reaction consisted of 4 min preheating at 94° C., followed by cycles of 45 sec 94° C., 45 sec 45° C., and 45 sec 72° C. After 10, 15, 20, 25, 30 and 35 cycles 10 µl of the amplification mixture was loaded on an agarose gel and electophoretically separated. After depurination, denaturation, and neutralisation of the DNA it was transferred to a nitro-cellulose membrane (Hybond N$^+$; Amersham). The DNA was fixed on the membrane by UV crosslinking.

Membranes were hybridised using fluorescein-labelled probes prepared of the FL39, FL66, or LDV159 genes according to the manufacturer's protocol (Amersham). After 16 hours hybridisation at 65° C., the membranes were washed for 15 min using 2×SSC; 0.1×SDS, and 15 min using 1×SSC; 0.1×SDS. The signals were detected using the CDP-star detection module according to the manufacturer's protocol (Amersham). The signals were revealed by autoradiography.

FL39 transcripts could be detected at days 1, 5, and 8; but not in late stationary cells (day 12). The strongest expression was noticed in cells being in the exponential growth phase (at day 5). The FL66 and LDV159 genes were most abundantly expressed at day 5 (during the exponential growth phase), although expression was already substantial high at day 1 during the lag phase. Both genes were expressed at a strongly reduced level in stationary cultures (at day 8 and 12).

Example 9

FL66 Transcription is Upregulated by NaCl

Stationary *A. thaliana* suspension cultures were diluted at day 1 in fresh medium and cultivated for 48 hours At this time-point the culture was divided into two subcultures. At one of these cultures 1% NaCl was added. The cultures were cultivated for 12 hours after which the cells were collected and frozen in liquid nitrogen. Of these samples RNA was prepared using the Trizol reagent (Bibco BRL). 100 µg of this total RNA preparation of both samples was used for mRNA extraction using Dynabeads oligoT25 (Dynal). The poly-A RNA was electophorically separated on an agarose gel and blotted onto a nitro-cellulose membrane (Hybond-N+, Amersham). The membrane was hybridised using a fluorescein-labelled probe prepared of the FL66 sequence according to the manufacturer's protocol (Amersham). After 16 hours hybridisation at 65° C., the membranes were washed for 15 min using 2×SSC; 0.1×SDS, and 15 min using 1×SSC; 0.1×SDS. The signals were detected using the CDP-star detection module (Amersham). The signals were revealed by autoradiography.

A weak hybridising band of approximately 1000 bp was detected in the control sample. Treatment with 1% NaCl clearly increased the intensity of the hybridisation signal. This demonstrates that the stress caused by the addition of NaCl results in the transcriptional activation of the FL66 gene. This induction could result in a permanent or transient arrest of cell division activity.

Example 10

Production of the CKIs in Plants

To obtain transgenic plants overexpressing the *A. thaliana* CKI genes, the coding regions of FL36, FL66, and LDV159 were cloned into the pAT7002 vector (Aoyama and Chua, 1997, Plant J. 11, p605–612). This vector allows inducible expression of the cloned inserts by the addition of the glucocorticoid dexamethasone. Following the polymerase chain reaction (PCR) technology the coding regions of FL39, FL66, and ICK1 were amplified using the appropriate primer combinations. The primers used were 5'-CGGCTC-GAGGAGAACCACAAACACGC-3' (SEQ ID NO: 19) and 5'-CGAAACTAGTTAATTACCTCAAGGAAG-3' (SEQ ID NO: 20) for FL39, GATCCCGGGCGATATCAGCGT-CATGG-3' (SEQ ID NO: 21) and 5'-GATCCCGGGT-TAGTCTGTTAACTCC-3' (SEQ ID NO: 22) for FL66, and 5'-CCCGCTCGAGATGGTGAGAAAATATA-GAAAAGCTAAAGGATTTGTAGAAGC TGGAGTTTCGTCAACGTA-3' (SEQ ID NO: 23) and 5'-GGACTAGTTCACTCTAACTTTACCCATTCG-3' (SEQ ID NO: 24) for LDV159. The obtained FL39 and LDV159 PCR fragments were purified and cut with XhoI and SpeI. Subsequently these fragments were used to clone into the XhoI and SpeI sites of pTA7002. The obtained FL66 fragment was cut with SmaI, purified, and cloned blunt into the XhoI and SpeI sites of the pTA7002 vector. The resulted binary vectors were transferred into *Agrobacterium tumefaciens*. These stains were used to transform *Nicotiana tabacum* cv. Petit havana using the leaf disk protocol (Horsh et al., 1985, Science 227, p1229–1231) and *Arabidopsis thaliana* using the root transformation protocol (Valvekens et al., 1988, PNAS 85, p5536–5540).

Example 11

*Arabidopsis thaliana* CKIs Expression in Fission Yeast *Schizosaccharomyces pombe*

To obtain heterologous expression of *A. thaliana* CKI genes in the fission yeast *Schizosaccharomyces pombe*, the FL39 and FL66 were cloned into the pREP81 (Basi et al., 1993, Gene 123, p131–136) and BNRP3 (Hemerly et al., 1995, EMBO J. 14, p3925–3936) vectors. These vectors contain the thiamine-repressible promoter nmt1 and allow inducible expression of the FL39 and FL66 genes (Maundrell et al., 1990, JBC 265, p10857–10864). The expression is inducible to different levels: strong induction is obtained with BNRP3, low induction with pREP81. The coding region of FL39 and FL66 were amplified by PCR technique. The FL66 amplified coding sequence encloses a protein starting at the methionine at amino-acid position 11, therefore not including the first 10 amino-acids encoded by the FL66 clone. Primers used to amplify FL39 were 5'-GAT-CATCTTAAGCATCATCGTCTTCTTCATGG-3' (SEQ ID NO: 25) and 5'-TAGGAGCATATGGCGGCGG-3' (SEQ ID NO: 26). Primers used to amplify FL66 were 5'ATAT-CAGCGCCATGGAAGTC-3' (SEQ ID NO: 27) and 5'-GGAGCTGGATCCTTTTGGAATTCATGG-3' (SEQ ID NO: 28). The obtained FL39 PCR fragment was purified, phosphorylated with polynucleotide kinase (blunt end) and cut with NdeI. This fragment was cloned into the NdeI and SmaI sites of pREP81. The obtained FL66 PCR fragment was purified, cut with NcoI and BamHI and cloned into the NcoI and BamHI sites of BNRP3.

The resulting recombinant plasmids were transformed in 972 leu1-32 h⁻ *Sch. pombe* strain (wild type) by electroporation technique. Transformant were selected on inducing medium supplemented with 5 µg/ml of thiamine. Phenotypes of transformants were then compared with the phenotype of wild type strain, on non-inducing medium. No cell cycle block could be observed in *Sch. pombe* transformants expressing FL39 or FL66.

Example 12

Identification of a FL66 Related Gene

By screening the *A. thaliana* sequence databank a genomic sequence was identified encoding a protein highly homologous to FL66. The protein encoded, annotated as 'unknown protein', was renamed FL67. FL67 shows 39.545% similarity and 30.909% identity with FL66.

Example 13

In situ Hybridisation Patterns

Plant material was fixed in 2.5% glutaraldehyde in 0.1 M cacodylate buffer (pH7.2) and dehydrated until 100% ethanol prior to embedding in paraffin and tissue sectioning. 35S-UTP-labeled sense and antisense RNAs of cDNA from FL39, FL66 and LDV159 subcloned in PGem2 were generated by run-off transcription using T7 and Sp6 RNA polymerases according to the manufacturer's instructions (Boehringer Mannheim). Labeled RNA probes were hydrolysed to an average length of 200 nt according to Cox et al (1984). Deparaffinized and rehydrated tissue sections were taken through the mRNA in situ procedure essentially as described by Angerer and Angerer (1992). Stringencies during washes were 2×SSC at room temperature for 60 min and 0.1×SSC in 50% formamide at 45 C for 30 min. RNase treatment, washing steps, photograph emulsion coating, and the development of slides were performed as described by Angerer and Angerer (1992). Photographs were taken with a Diaplan microscope equipped with dark-field optics (Leitz, Wetzlar, Germany).

Distinct expression patterns of the FL39, LDV159 and FL66 genes were observed when applying the mRNA in situ hybridization technique on *Arabidopsis thaliana* and radish seedlings. Sections of paraffin embedded roots, shoot apical meristems, flowers and siliques of *Arabidopsis thaliana*, and radish roots and shoot apical meristems were used to hybridize with the three cyclin-dependent kinase inhibitors. The FL39 gene is expressed in young root meristems in a homogeneous pattern. Mature root meristems barely showed any expression of the gene. Some regions along the root vascular tissue showed alternating zones of expressing and nonexpressing cells at the periphery of the vascular bundle. A region of pericycle cells in the vascular tissue, flanking the region where new lateral roots usually form, presented a very strong expression of the FL39 gene. In contrast, pericycle cells on the region where lateral roots form hardly showed any expression. These results show that higher levels of FL39 mRNA was observed close to the region where lateral roots emerge possibly preventing their formation at these regions. On the other hand, the absence of FL39 gene expression in the poles of the diarch vascular bundle may allow lateral root formation at these sites. It possibly assures that lateral roots are formed by division of pericycle cells adjacent to a protoxylem group. Uniform expression of FL39 gene was also observed in all cells of the shoot apical meristem. Strong signals were observed at the surface and tip of young leaves. The epidermal and palissade layers of the leaves are the first layers to vacuolize and differentiate, and the oldest part of the leaves are at the tip. In addition, the expression pattern of CYCB1; 1, a molecular marker of cell division, shows a basipetal pattern of cessation of cell division. Therefore, FL39 expression at these sites may inhibit cell division allowing cell differentiation to occur during early stages of leaf development. A similar pattern of expression was observed on radish leaves, roots and shoot apical meristems. In addition, strong expression at the epidermis of the stem was also observed on young seedlings. The presence of FL39 mRNA in these cells might allow cells to differentiate. In *Arabidopsis* flowers, FL39 was mainly expressed in the tapetal layer of the anthers and in pollen grains. Considering that at this stage, tapetum and pollen grains do not divide, FL39 might be expressed at these sites to inhibit cell division. Weaker expression was observed in flower buds and mature ovaries. During embryo development very strong expression was observed in embryos at the globular, heart and torpedo stages. At the later stage strongest expression was at the embryonic root. Weak or no hybridization signal was observed in mature seeds.

Expression of the LDV159 was also observed in all cells along the main and lateral root meristems and shoot apical meristems, but in a more uniform manner. Expression in vascular tissue was slightly patchy, and stronger at the pericycle. Often a patchy pattern was observed in distinct cells of mature leaves. In flowers, expression was mainly observed in mature ovaries. Expression in embryos was mainly observed in globular and heart stages and in the embryonic root at the torpedo stage. Weak expression was observed in mature embryos. These results suggest a function of LDV159 in the regulation of correct progression through the cell cycle. LDV159 might play a role in the checkpoint control, avoiding the premature activation of the CDK complexes under unfavorable conditions. Its association with CDKs could inhibit CDK activity until the cell perceives the correct signals to progress to the next cell cycle phase.

FL66 gene expression was observed in the root and shoot apical meristems. Stronger expression was observed in young differentiating leaves often in a patchy manner suggesting a cell cycle phase dependent expression pattern. Hybridization signal was also observed along the vascular tissue. FL66 expression was as well observed in flower buds and young flowers. In mature flowers stronger expression was observed in the ovary wall, funiculus, ovules and pollen grains. During embryo development strong expression was observed at the globular stage. Signal gradually decreases until the embryo maturation. Stronger signals were often observed in the embryonic root.

Example 14

Identification of a CKI in Alfalfa

The *Medicago sativa* cdc2-related kinase (CDC2AMs; Magyar et al., 1997, The Plant Cell, Vol.: 9, 223–235.) cloned in the vector pBD-GAL4 Cam phagemid (Stratagene) was used as a bait protein in a yeast two-hybrid screen. mRNA isolated from young alfalfa (*Medicago truncatula*) root nodules was converted to cDNA followed by cloning into HybridZAP phagemids (Stratagene). The library was converted to pAD-GAL4 plasmid library by mass excision. The yeast strain Y190 (Clontech) was used as a host for the two hybrid analysis. As a positive clone interacting in this system with the CDC2MsA kinase, a partial cDNA clone of 613 bp was isolated coding for 128 amino acids. Sequencing of this clone revealed extensive homology with the C-terminal region of known CDK inhibitors (CKI). The full length cDNA clone was isolated with screening an alfalfa root nodule Lambda ZAP II (Stratagene) cDNA library with the partial cDNA as probe and using standard procedures. A clone comprising a full length cDNA designated ALFCDKI was obtained and the corresponding nucleotide and amino acid sequences of the encoded CKI are shown in SEQ ID NO: 5 and 6, respectively.

Example 15

In Situ Hybridization Analysis

Radish seedlings were treated for in situ hybridization as described in Example 13. Tissue sections were hybridized to a 35S-labelled RNA probe, corresponding to the coding region and 3' UTR of ICK2, for 16h at 42 C in 50% formamide. Post hybridization washes were: 1 h at RT in 2×SSC and 1H at 45 C in 0.1×SSC in 50% formamide. Slides were exposed for 45 days. Slides were subsequently developed, toluidine blue stained and photographed using bright field optics.

The spatial expression pattern of the different CKIs was studied in *Arabidopsis thaliana* and radish by in situ hybridization analysis. Transcripts localisation were similar in both plants. ICK1 and ICK3 were predominantly expressed at places with a lot of cell division. The CKI2 expression pattern was quite different. In the shoot apical meristem, ICK2 expression was only occasionally observed in individual cells of the L1 layer (FIG. 2B). In leaf primordia however, ICK2 mRNA accumulation was observed in both the adaxial and abaxial epidermis in a uniform manner (FIGS. 2C and 2D). As leaves matured, the signal became more distributed along the epidermal layer (FIGS. 2E and 2F), whereas in fully differentiated leaves, ICK2 signal could no longer be detected. This temporal expression of ICK2 correlated with the occurrence of vacuolisation and differentiation (16), suggesting that ICK2 expression at these sites may inhibit cell division allowing cell differentiation to occur.

Surprisingly, no expression was noticed at the margins of maturing leaves. Cells located at these margins are thought to regulate blade inception due to meristematic activity.

Example 16

ICK2 Transgenic Plants

The full length ICK2-coding region was amplified by polymerase chain reaction (PCR) using the 5'-AGACCATG-GCGGCGGTTAGGAG-3' (SEQ ID NO:41) and 5'-GGCG-GATCCCGTCTTCTTCATGGATTC-3' (SEQ ID NO:10) primers and the pFL39 plasmid as template, introducing NcoI and BamHI restriction sites. The amplified fragment was cut with NcoI and BamHI and cloned between the NcoI and BamHI sites of PH35S (Hemerly et al., 1995), resulting into the 35FL39 vector. The CaMV35S/ICK2/NOS cassette was released by EcoRI and XbaI and cloned blunt into the SmaI site of PGSV4 (Heourt et al, 1994). The resulting vector PGSFL39, was mobilized by the helper plasmid pRK2013 into *Agrobacterium tumefaciens* C58C1RifR harboring the plasmid pMP90. *A thaliana* plants ecotype Col-O were transformed by the floral dip method (Clough and Bent, 1998). Transgenic plants were obtained on kanamycin-containing media and later transferred to soil for optimal seed production. For all analysis plants were grown in vitro with 16-h light/8-h dark illumination at 22 C on germination medium (GM, Valvekens et al., 1988). Molecular analysis of the obtained transformants was performed by Northern as described by Jacqmard et al. (1999); and Western blotting and CDK kinase activity measurements as described by De Veylder et al. (1997).

Transgenic plants were generated containing ICK2 under the control of the constitutive CaMV 35S promoter. A total of 39 lines were generated.

The level of ICK2 mRNA and protein in the transgenic plants exceeded the amount found in untransformed plants as shown in FIG. 11 for the ICK2 (CKI2) protein. Concurrently the amount of Cdc2a protein is increased and the presence of ICK2 protein correlated with a moderate decrease in extractable CDK activity (FIG. 11).

All ICK2 overproducing lines displayed highly serrated leaves (see e.g., FIG. 3B and the ICK21.0 plant leaf in FIG. 3C) in comparison to control plants (see e.g., FIG. 3A and the leaf from control plant in FIG. 3C). In the T2 population the leaf phenotype strictly segregated with presence and expression of the transgene, with lines homozygous for the transgene displaying a more severe phenotype than the heterozygous lines. The severity of the phenotype also correlated with the different amount of ICK2 protein found in independent transgenics. The number of leaves initiated was not affected (mean, 7.25 leaves per plant with a standard deviation of 0.85 in wild type plants (n=139), compared to 7.28±1.06 (n=137) and 7.54±1.03 (n=196), respectively, in two independent transgenics), suggesting ICK2 overexpression had no effect on the shoot apical meristem.

The venation pattern was also clearly altered in the ICK2 overexpressing plants. As FIGS. 4A and 4B depict, plants expressing the ICK2 transgene show a less complex pattern of venation when compared to wild type plants (FIG. 4A).

Example 17

Microscopic Analysis of ICK2 Transgenic Plants

For microscopic analysis, leaves were prepared by fixing in 2% gluaraldehyde in 0.1 M cacodylate buffer (pH7.2) and dehydrated until 100% ethanol prior to embedding in paraffin and tissue sectioning. Leaves were sectioned through the central part of the leaves and sections were stained with toluidine blue. Microscopic analysis revealed that leaves from ICK2 expressing plants had larger cells in all tissue layers. See FIGS. 6A and 6B. DIC microscopic analysis of whole-mount cleared leaves also indicated that the leaves of ICK2 overexpressing lines consist of much larger cells in all tissue layers, as illustrated for the adaxial and abaxial epidermis and palissade (FIG. 7). Measurements on pavement cells illustrated that the cells in the ICK2 overproducing lines are 5 to 10 fold larger than control cells and FIG. 5.

In the overexpressing plants with the most severe phenotype, cotyledons displayed enlarged stomata of variable sizes (FIG. 8B) when compared to stomata on cotyledons from control plants (FIG. 8A). In some sectors, giant stomata were found filled with large clusters of starch grains (see, e.g., FIG. 8B). Similar stomata, although less frequent were found in vegetative leaves.

The flowers of CKI2 expressing plants also showed smaller petals but composed of much larger cells (in the order of 5 times as normal plants), comparable to what is seen in the leaves of these plants.

Cells from stem tissue are also larger than control (wt) plants.

Example 18

Ploidy Measurements of ICK2 Leaves

Leaves were chopped in 300 µl Galbraith buffer (45 mM MgCl2, 30 mM Sodiumcistrate, 20 mM MOPS pH=7, 1% Triton-X100) using a razor blade. To the supernatans which was filtered over a 30 µm mesh, 1 µl DAPI of a stock of 1 mg/ml was added. The nuclei were analysed using the BRYTE HS flow cytometer and WinBryte™ software (Bio-Rad, Hercules, Calif., USA).

Leaves of *Arabidopsis thaliana* undergo endoreduplication. Effects of increased ICK2 expression on the ploïdy was measured by flow cytometry. In control plants a developmental change in the ploïdy level can be observed, with the number of 2C cells decreasing in older leafs. Simultaneously an increase in the 4C and 8C DNA levels can be observed. In the youngest leaf measured (leaf 5), no dramatic charge in the ploïdy levels between control and transgenic plants was observed. However, as leafs matured, the 2C level in heterozygous lines increased by 5.4% and 20.1% in leaf three and leaf one, respectively. In homozygous lines the effect was even more drastically, with an increase of 20.1% and 24.9% in leafs three and one. This increase was compensated by a decrease of mainly the 4C level in leaf 3, and 4C and 8C in leaf 1. Thus, ICK2 appears to function primarily to facilitate the transition form the mitotic cycle to a G1 arrest.

Example 19

Analysis of Seeds in ICK2 Overexpressing Lines

Seed size distribution of wild type and ICK2 overexpressing lines on the seeds from two plants per line was determined using the following methods. Between 100 and 300 seeds per parental plant were placed on a flatbed scanner. Images were scanned at 2400 dpi and analysed using the program Photoshop with a set of additional image analysis plug-ins (the image processing toolkit version 3.0, Reindeer Games, Inc). The procedure was as follows: First the image was thresholded to select the seeds. Then touching seeds were separated using the watershed routine. After that all size/shape parameters were determined using the features/ measure all command. From the resulting file the columns containing area, length, breadth, formfactor and roundness were selected. Outliers (dust and contamination particles) were removed based on their deviating formfactor and roundness factor. Of the remaining seeds the distribution was plotted and mean, median, average, standard deviation and standard error of the mean determined.

Results indicated that compared to wild types, the seeds of ICK2 are significantly smaller. The variability in size is greater in the wild type than in the transgenic lines.

CKI2 expressing plants produce smaller seeds than wild type plants. The shape of the seed is also affected. See e.g., FIGS. 9A and 9B.

Example 20

ICK2, Cdc2aAt and Rubisco Protein Levels and CDK Kinase Activity

Total soluble protein was extracted from leaves of one wild-type Col-O line (lane 1, FIG. 11) and four independent CKI2 transgenic lines (lanes 2 through 5, FIG. 11). Protein samples were analyzed by Western blotting for the visualization of CKI2 protein and Cdc2aAt protein. Rubisco was used as a marker for equal protein amount loading. CDK kinase activity was measured using $p10^{Cks1At}$ Sephrarose beads and histone H1 as substrate.

What is claimed is:

1. A method for decreasing cyclin-dependent kinase activity in a plant, the method comprising:
   (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell, and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
   (b) regenerating a plant from the plant cell, wherein the regenerated plant has decreased cyclin dependent kinase activity relative to a corresponding wild type plant.

2. A method for increasing in a plant cell, the level of cyclin-dependent kinase inhibitor (CKI) which binds a plant cyclin-dependent kinase, the method comprising:
   (a) introducing into a plant cell a nucleic acid molecule encoding a plant (CKI) which binds a plant cyclin-dependent kinase having a PSTAIRE cyclin-binding motif, wherein the nucleic acid molecule encoding the plant CKI is under the control of a promoter which functions in a plant cell, and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
   (b) expressing the nucleic acid molecule in the plant cell, thereby increasing the level of CKI in the plant cell relative to a corresponding cell of a wild type plant.

3. A method for increasing plant cell size, the method comprising:
   (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell, and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
   (b) expressing the nucleic acid molecule in the plant cell, thereby increasing plant cell size relative to a corresponding wild type plant.

4. The method of claim 3 wherein the plant cell is a floral petal cell.

5. The method of claim 3 wherein the plant cell is a leaf cell.

6. The method of claim 3 wherein the plant cell is a stem cell.

7. A method for decreasing cell number in a plant, the method comprising:
   (a) introducing into a plant cell a nucleic acid molecule encoding a cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
   (b) regenerating a plant from the plant cell, wherein the regenerated plant has decreased cell number relative to a corresponding wild type plant.

8. A method of increasing leaf serration in a plant the method comprising:
   (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
   (b) regenerating a plant from the plant cell, wherein the regenerated plant has increased leaf serration relative to a corresponding wild-type plant.

9. A method of increasing stomata size in a plant, the method comprising:
  (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
  (b) regenerating a plant from the plant cell, wherein the regenerated plant has increased stomata size relative to a corresponding wild type plant.

10. A method of reducing petal size in a plant, said method comprising:
  (a) introducing into a plant cell a nucleic acid molecule encoding a plant cyclin-dependent kinase inhibitor (CKI) which binds a plant cyclin dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
  (b) regenerating a plant from the plant cell, wherein the regenerated plant has flowers with reduced petal size relative to a corresponding wild type plant.

11. The method of claim 10 wherein the promoter which functions in a plant cell is a petal-specific promoter.

12. A method of reducing leaf venation in a plant, said method comprising: (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
  (b) regenerating a plant from the plant cell, wherein the regenerated plant has leaves with reduced leaf venation relative to a corresponding wild type plant.

13. A method of decreasing endoreduplication and ploidy level in a plant cell, the method comprising:
  (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
  (b) expressing the nucleic acid molecule in the plant cell, thereby decreasing endoreduplication and ploidy level in the plant cell relative to a corresponding cell from a wild type plant.

14. A method of reducing plant seed size, the method comprising:
  (a) introducing into a plant cell a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
  (b) regenerating a plant from the plant cell, wherein the regenerated plant has decreased seed size relative to a corresponding wild type plant.

15. A transgenic plant, a variety obtained therefrom, a plant part, or plant cell which comprises a nucleic acid molecule encoding a plant cyclin-dependent kinase inhibitor (CKI) which binds a plant cyclin-dependent kinase having a PSTAIRE cyclin-binding motif, wherein the nucleic acid molecule encoding the plant CKI is under the control of a promoter which functions in a plant cell and wherein the CKI comprises an amino acid sequence as set forth in SEQ ID NO:34 or an amino acid sequence that is at least 87.5% identical thereto, and an amino acid sequence as set forth in SEQ ID NO:35 or an amino acid sequence that is at least 87.5% identical thereto, and an amino acid sequence as set forth in SEQ ID NO:36 or an amino acid sequence that is at least 90% identical thereto; and
  wherein the nucleic acid molecule encoding a plant CKI is heterologous to the genome of the transgenic plant, or is homologous but additional to the genome of the transgenic plant or has been introduced into the transgenic plant, plant part or plant cell by recombinant DNA means.

16. The transgenic plant of claim 15 having decreased cyclin-dependent kinase activity relative to a corresponding wild type plant.

17. The transgenic plant of claim 15 having an increased level of CKI relative to a corresponding wild type plant.

18. The transgenic plant of claim 15 having altered leaf shape relative to a corresponding wild type plant.

19. The transgenic plant of claim 15 having leaves which are more highly serrated compared to a corresponding wild type plant.

20. The transgenic plant of claim 15 having leaves which are more deeply lobed than a corresponding wild type plant.

21. The transgenic plant of claim 15 having flowers with reduced petal size relative to flowers of a corresponding wild type plant.

22. The transgenic plant of claim 15 having reduced leaf venation relative to leaves of a corresponding wild type plant.

23. The transgenic plant of claim 15 having cells with decreased endoreduplication and ploidy levels relative to a corresponding wild type plant.

24. The transgenic plant of claim 15 having reduced seed size relative to a corresponding wild type plant.

25. The transgenic plant of claim 15, wherein the total cell number of the plant is decreased relative to a corresponding wild type plant.

26. The transgenic plant of claim 15, wherein at least one of petals, leaves or stems comprise cells of increased size relative to a corresponding wild type plant.

27. The transgenic plant of claim 15, comprising leaves with increased stomata size relative to a corresponding wild type plant.

28. The method of any one of claims 1, 2, 3–7, 8, 9, 10, 11, 12, 13, or 14, wherein the CKI comprises the amino acid sequence as set forth in any one of SEQ ID NO: 2, SEQ ID NO:4, or SEQ ID NO:6.

29. The method of any one of claims 1, 2, 3–7, 8, 9, 10, 11, 12, 13, or 14, wherein the nucleic acid molecule comprises the nucleotide sequence as set forth in any one of SEQ ID NO:1, SEQ ID NO:3, or SEQ ID NO:5.

30. The method of any one of claims 1, 2, 3–7, 8, 9, 10, 11, 12, 13, or 14 wherein the CKI further comprises the consensus amino acid sequence as set forth in SEQ ID NO:37 or a sequence that is at least 87.5% identical thereto, or wherein the CKI further comprises the consensus amino acid sequences as set forth in SEQ ID NO:37 or a sequence that is at least 87.5% identical thereto, and a sequence as set forth in SEQ ID NO:38 and a sequence as set forth in SEQ ID NO:39 or a sequence that is at least 75% identical thereto.

31. The transgenic plant of claim 15 wherein the CKI further comprises the consensus amino acid sequence as set forth in SEQ ID NO:37 or a sequence that is at least 87.5% identical thereto, or wherein the CKI further comprises the consensus amino acid sequences as set forth in SEQ ID NO:37 or a sequence that is at least 87.5% identical thereto, and a sequence as set forth in SEQ ID NO:38 and a sequence as set forth in SEQ ID NO:39 or a sequence that is at least 75% identical thereto.

32. Harvestable parts or propagation material from the transgenic plant of claim 15, comprising the nucleic acid molecule that was introduced into the parent plant.

33. Cut flowers from the transgenic plant of claim 15, comprising the nucleic acid molecule that was introduced into the parent plant.

* * * * *

SEQUENCE LISTING

<160> NUMBER OF SEQ ID NOS: 48

<210> SEQ ID NO 1
<211> LENGTH: 932
<212> TYPE: DNA
<213> ORGANISM: Arabidopsis thaliana
<220> FEATURE:
<221> NAME/KEY: CDS
<222> LOCATION: (86)..(712)

<400> SEQUENCE: 1

```
ggcacgagga gaaccacaaa cacgcacaca taacgagtga ttttagagag agatagagat         60
ctggaaggtg acgtcgtagg agatt atg gcg gcg gtt agg aga aga gaa cga        112
                              Met Ala Ala Val Arg Arg Arg Glu Arg
                                1               5 gat gtg gtt gaa gag aat gga gtt acg acg acg gtg aaa cga agg              160
Asp Val Val Glu Glu Asn Gly Val Thr Thr Thr Val Lys Arg Arg
 10                  15                  20                  25 aag atg gag gag gaa gtg gat tta gtg gaa tct agg ata att ctg tct          208
Lys Met Glu Glu Glu Val Asp Leu Val Glu Ser Arg Ile Ile Leu Ser
                 30                  35                  40 ccg tgt gta cag gcg acg aat cgc ggt gga att gtg gcg aga aat tca          256
Pro Cys Val Gln Ala Thr Asn Arg Gly Gly Ile Val Ala Arg Asn Ser
             45                  50                  55 gca gga gcg tcg gag acg agt gtt gtt ata gta cga cgg cga gat tct          304
Ala Gly Ala Ser Glu Thr Ser Val Val Ile Val Arg Arg Arg Asp Ser
         60                  65                  70 cct ccg gtt gaa gaa cag tgt caa atc gaa gaa gaa gat tcg tcg gtt          352
Pro Pro Val Glu Glu Gln Cys Gln Ile Glu Glu Glu Asp Ser Ser Val
     75                  80                  85 tcg tgt tgt tct aca tcg gaa gag aaa tcg aaa cgg aga atc gaa ttt          400
Ser Cys Cys Ser Thr Ser Glu Glu Lys Ser Lys Arg Arg Ile Glu Phe
 90                  95                 100                 105 gta gat ctt gag gaa aat aac ggt gac gat cgt gaa aca gaa acg tcg          448
Val Asp Leu Glu Glu Asn Asn Gly Asp Asp Arg Glu Thr Glu Thr Ser
                110                 115                 120 tgg att tac gat gat ttg aat aag agt gag gaa tcg atg aac atg gat          496
Trp Ile Tyr Asp Asp Leu Asn Lys Ser Glu Glu Ser Met Asn Met Asp
            125                 130                 135 tct tct tcg gtg gct gtt gaa gat gta gag tct cgc cgc agg tta agg          544
Ser Ser Ser Val Ala Val Glu Asp Val Glu Ser Arg Arg Arg Leu Arg
        140                 145                 150 aag agt ctc cat gag acg gtg aag gaa gct gag tta gaa gat ttt ttt          592
Lys Ser Leu His Glu Thr Val Lys Glu Ala Glu Leu Glu Asp Phe Phe
    155                 160                 165 cag gtg gcg gag aaa gat ctt cgg aat aag ttg ttg gaa tgt tct atg          640
```

-continued

```
Gln Val Ala Glu Lys Asp Leu Arg Asn Lys Leu Leu Glu Cys Ser Met
170                 175                 180                 185 aag tat aac ttc gat ttc gag aaa gat gag cca ctt ggt gga gga aga      688
Lys Tyr Asn Phe Asp Phe Glu Lys Asp Glu Pro Leu Gly Gly Gly Arg
                    190                 195                 200 tac gag tgg gtt aaa ttg aat cca tgaagaagac gatgatgata atgatgatca    742
Tyr Glu Trp Val Lys Leu Asn Pro
                205 ttgttttcac caaagtactt attatttttc ttctgtaata atctttgctt tgattttttct   802 tttaacaaaa tccaaatgta gatatctttc tctcgaataa tcaataacat gtaattcaac   862 ttttgtttgt acttccttga ggtaattaat tagattcgtg tttttctcga ttaataaact   922 ataagtttat                                                          932
```

```
<210> SEQ ID NO 2
<211> LENGTH: 209
<212> TYPE: PRT
<213> ORGANISM: Arabidopsis thaliana

<400> SEQUENCE: 2

Met Ala Ala Val Arg Arg Arg Glu Arg Asp Val Val Glu Glu Asn Gly
1               5                   10                  15

Val Thr Thr Thr Thr Val Lys Arg Arg Lys Met Glu Glu Glu Val Asp
                20                  25                  30

Leu Val Glu Ser Arg Ile Ile Leu Ser Pro Cys Val Gln Ala Thr Asn
            35                  40                  45

Arg Gly Gly Ile Val Ala Arg Asn Ser Ala Gly Ala Ser Glu Thr Ser
        50                  55                  60

Val Val Ile Val Arg Arg Arg Asp Ser Pro Val Glu Glu Gln Cys
65                  70                  75                  80

Gln Ile Glu Glu Glu Asp Ser Ser Val Ser Cys Cys Ser Thr Ser Glu
                85                  90                  95

Glu Lys Ser Lys Arg Arg Ile Glu Phe Val Asp Leu Glu Glu Asn Asn
            100                 105                 110

Gly Asp Asp Arg Glu Thr Glu Thr Ser Trp Ile Tyr Asp Asp Leu Asn
        115                 120                 125

Lys Ser Glu Glu Ser Met Asn Met Asp Ser Ser Val Ala Val Glu
    130                 135                 140

Asp Val Glu Ser Arg Arg Arg Leu Arg Lys Ser Leu His Glu Thr Val
145                 150                 155                 160

Lys Glu Ala Glu Leu Glu Asp Phe Phe Gln Val Ala Glu Lys Asp Leu
                165                 170                 175

Arg Asn Lys Leu Leu Glu Cys Ser Met Lys Tyr Asn Phe Asp Phe Glu
            180                 185                 190

Lys Asp Glu Pro Leu Gly Gly Gly Arg Tyr Glu Trp Val Lys Leu Asn
        195                 200                 205

Pro
```

```
<210> SEQ ID NO 3
<211> LENGTH: 875
<212> TYPE: DNA
<213> ORGANISM: Arabidopsis thaliana
<220> FEATURE:
<221> NAME/KEY: CDS
<222> LOCATION: (11)..(658)

<400> SEQUENCE: 3
```

```
ggcacgagag aaa tca aag ata act ggc gat atc agc gtc atg gaa gtc        49
           Lys Ser Lys Ile Thr Gly Asp Ile Ser Val Met Glu Val
             1               5                  10 tct aaa gca aca gct cca agt cca ggt gtt cga acc aga gcc gct aaa        97
Ser Lys Ala Thr Ala Pro Ser Pro Gly Val Arg Thr Arg Ala Ala Lys
         15                  20                  25 acc cta gcc ttg aag cgg ctt aat tcc tcc gcc gct gat tca gct cta       145
Thr Leu Ala Leu Lys Arg Leu Asn Ser Ser Ala Ala Asp Ser Ala Leu
 30                  35                  40                  45 cct aac gac tct tct tgc tat ctt cag ctc cgt agc cgc cgt ctc gag       193
Pro Asn Asp Ser Ser Cys Tyr Leu Gln Leu Arg Ser Arg Arg Leu Glu
                 50                  55                  60 aaa ccc tct tcg ctg att gaa ccg aaa cag ccg ccg aga gtt cac aga       241
Lys Pro Ser Ser Leu Ile Glu Pro Lys Gln Pro Pro Arg Val His Arg
 65                  70                  75 tcg gga att aaa gag tct ggt tcc agg tct cgc gtt gac tcg gtt aac       289
Ser Gly Ile Lys Glu Ser Gly Ser Arg Ser Arg Val Asp Ser Val Asn
         80                  85                  90 tcg gtt cct gta gct cag agc tct aat gaa gat gaa tgt ttt gac aat       337
Ser Val Pro Val Ala Gln Ser Ser Asn Glu Asp Glu Cys Phe Asp Asn
 95                 100                 105 ttc gtg agt gtc caa gtt tct tgt ggt gaa aac agt ctc ggt ttt gaa       385
Phe Val Ser Val Gln Val Ser Cys Gly Glu Asn Ser Leu Gly Phe Glu
110                 115                 120                 125 tca aga cac agc aca agg gag agc acg cct tgt aac ttt gtt gag gat       433
Ser Arg His Ser Thr Arg Glu Ser Thr Pro Cys Asn Phe Val Glu Asp
                130                 135                 140 atg gag atc atg gtt aca cca ggg tct agc acg agg tcg atg tgc aga       481
Met Glu Ile Met Val Thr Pro Gly Ser Ser Thr Arg Ser Met Cys Arg
        145                 150                 155 gca acc aaa gag tac aca agg gaa caa gat aac gtg atc ccg acc act       529
Ala Thr Lys Glu Tyr Thr Arg Glu Gln Asp Asn Val Ile Pro Thr Thr
    160                 165                 170 agt gaa atg gag gag ttc ttt gca tat gca gag cag cag caa cag agg       577
Ser Glu Met Glu Glu Phe Phe Ala Tyr Ala Glu Gln Gln Gln Gln Arg
175                 180                 185 cta ttc atg gag aag tac aac ttc gac att gtg aat gat atc ccc ctc       625
Leu Phe Met Glu Lys Tyr Asn Phe Asp Ile Val Asn Asp Ile Pro Leu
190                 195                 200                 205 agc gga cgt tac gaa tgg gtg caa gtc aaa cca tgaagttcaa aaggaaacag     678
Ser Gly Arg Tyr Glu Trp Val Gln Val Lys Pro
                210                 215 ctccaaaaga catggtgtga agttagagaa tgtgatggag ttaacagact aaccaaacat     738
cagaaatcgt gtaatcttaa gtaataatgt ggttagagaa caagtttgag agtagcttag     798
ggaccttaaa acctcacacc atttgtaata ctaatcttct tcagatgctt agtgaaattt     858
tctcatctgt ttcttc                                                     875

<210> SEQ ID NO 4
<211> LENGTH: 222
<212> TYPE: PRT
<213> ORGANISM: Arabidopsis thaliana

<400> SEQUENCE: 4

Met Gly Lys Tyr Met Lys Lys Ser Lys Ile Thr Gly Asp Ile Ser Val
  1               5                  10                  15

Met Glu Val Ser Lys Ala Thr Ala Pro Ser Pro Gly Val Arg Thr Arg
                 20                  25                  30

Ala Ala Lys Thr Leu Ala Leu Lys Arg Leu Asn Ser Ser Ala Ala Asp
```

-continued

```
                35                  40                  45
Ser Ala Leu Pro Asn Asp Ser Ser Cys Tyr Leu Gln Leu Arg Ser Arg
     50                  55                  60

Arg Leu Glu Lys Pro Ser Ser Leu Ile Glu Pro Lys Gln Pro Pro Arg
 65                  70                  75                  80

Val His Arg Ser Gly Ile Lys Glu Ser Gly Arg Ser Arg Val Asp
                 85                  90                  95

Ser Val Asn Ser Val Pro Val Ala Gln Ser Ser Asn Glu Asp Glu Cys
                100                 105                 110

Phe Asp Asn Phe Val Ser Val Gln Val Ser Cys Gly Glu Asn Ser Leu
            115                 120                 125

Gly Phe Glu Ser Arg His Ser Thr Arg Glu Ser Thr Pro Cys Asn Phe
        130                 135                 140

Val Glu Asp Met Glu Ile Met Val Thr Pro Gly Ser Ser Thr Arg Ser
145                 150                 155                 160

Met Cys Arg Ala Thr Lys Glu Tyr Thr Arg Glu Gln Asp Asn Val Ile
                165                 170                 175

Pro Thr Thr Ser Glu Met Glu Glu Phe Phe Ala Tyr Ala Glu Gln Gln
            180                 185                 190

Gln Gln Arg Leu Phe Met Glu Lys Tyr Asn Phe Asp Ile Val Asn Asp
        195                 200                 205

Ile Pro Leu Ser Gly Arg Tyr Glu Trp Val Gln Val Lys Pro
    210                 215                 220

<210> SEQ ID NO 5
<211> LENGTH: 1193
<212> TYPE: DNA
<213> ORGANISM: Arabidopsis thaliana
<220> FEATURE:
<221> NAME/KEY: CDS
<222> LOCATION: (92)..(763)

<400> SEQUENCE: 5
aaaccactct tcaaatcaaa cactttctta cataagattc ctctgttttt ctgtgtgctt      60
cttcaaattc ttcccctgtt tttcaacttc a atg ggg aag tac atg aag aaa       112
                                   Met Gly Lys Tyr Met Lys Lys
                                    1               5 ctc aaa tcc aaa tca gaa tct cct tca ccc aat tca aca cca aca cca      160
Leu Lys Ser Lys Ser Glu Ser Pro Ser Pro Asn Ser Thr Pro Thr Pro
         10                  15                  20 tca cca tca cca tca cca aca cca atc acc acc aat tca cca cca cca      208
Ser Pro Ser Pro Ser Pro Thr Pro Ile Thr Thr Asn Ser Pro Pro Pro
 25                  30                  35 aca aca ccc aat tcc tct gat ggt gtt cga act cgt gct aga acc cta      256
Thr Thr Pro Asn Ser Ser Asp Gly Val Arg Thr Arg Ala Arg Thr Leu
 40                  45                  50                  55 gct ttg gag aat tcc aac aat cag aat cag aat ctt tct gtt tct tct      304
Ala Leu Glu Asn Ser Asn Asn Gln Asn Gln Asn Leu Ser Val Ser Ser
                 60                  65                  70 gat tct tac ctt cag ctg agg aac cgt cgc ctt aag aga ccc cta att      352
Asp Ser Tyr Leu Gln Leu Arg Asn Arg Arg Leu Lys Arg Pro Leu Ile
             75                  80                  85 agg caa cat tcc gct aag agg aat aag ggg cat gat gga aac cct aaa      400
Arg Gln His Ser Ala Lys Arg Asn Lys Gly His Asp Gly Asn Pro Lys
         90                  95                 100 tcc cca att ggg gat tca att gct gaa gag aaa act gtt cag aag agt      448
Ser Pro Ile Gly Asp Ser Ile Ala Glu Glu Lys Thr Val Gln Lys Ser
    105                 110                 115
```

-continued

```
cct gag cct gaa aat gct gaa ttc aag gag aat gct gag gat act gag       496
Pro Glu Pro Glu Asn Ala Glu Phe Lys Glu Asn Ala Glu Asp Thr Glu
120             125                 130                 135 aga agc gct agg gaa act aca ccc gtc cat ttg ata atg cga gca gac       544
Arg Ser Ala Arg Glu Thr Thr Pro Val His Leu Ile Met Arg Ala Asp
            140                 145                 150 gtt ctc agg cct cct agg cca att acc agg cgt act ttt cca act gaa       592
Val Leu Arg Pro Pro Arg Pro Ile Thr Arg Arg Thr Phe Pro Thr Glu
        155                 160                 165 gct aat ccc aaa acg gag cag cca act atc cca att tca cgc gaa ttt       640
Ala Asn Pro Lys Thr Glu Gln Pro Thr Ile Pro Ile Ser Arg Glu Phe
    170                 175                 180 gag gaa ttc tgt gct aaa cat gaa gcc gag cag caa agg gag ttc atg       688
Glu Glu Phe Cys Ala Lys His Glu Ala Glu Gln Gln Arg Glu Phe Met
185                 190                 195 gag aag tac aac ttt gat cct gtg aca gag cag cca ctc cca ggg cgt       736
Glu Lys Tyr Asn Phe Asp Pro Val Thr Glu Gln Pro Leu Pro Gly Arg
200             205                 210                 215 tac gaa tgg gaa aaa gtg tcg ccc tag aaggcaggct agtattaagt             783
Tyr Glu Trp Glu Lys Val Ser Pro
                220 gttccatcaa tacatcttta aagtagcagc agggttagaa tttgttgaaa agggtggtgg    843 tgctatttcc attttccatc actttctatt tacttgtaaa gaaagtagga ctttcaacat    903 atgtagacta atgatctgta actttacaga ggtgttgatt acacaacaat acaaagtcct    963 ttgtctagca gatcattaaa gaagggtttg agggaataag ggtctctagt tgtagggttt   1023 agggtataaa atcaaagtag ggtatgtaag agaggtttta caagaatttc cttttgttct   1083 tgtgttttac tcttgttttg tctatacttg tactcatgga acttcaacaa actcttaaga   1143 aataaagaac cagatctccc tcaaaaaaaa aaaaaaaaaa aaaaaaaaa               1193
```

<210> SEQ ID NO 6
<211> LENGTH: 223
<212> TYPE: PRT
<213> ORGANISM: Arabidopsis thaliana

<400> SEQUENCE: 6

```
Met Gly Lys Tyr Met Lys Lys Leu Lys Ser Lys Ser Glu Ser Pro Ser
1               5                   10                  15

Pro Asn Ser Thr Pro Thr Pro Ser Pro Ser Pro Thr Pro Ile
            20                  25                  30

Thr Thr Asn Ser Pro Pro Thr Thr Pro Asn Ser Ser Asp Gly Val
        35                  40                  45

Arg Thr Arg Ala Arg Thr Leu Ala Leu Glu Asn Ser Asn Asn Gln Asn
    50                  55                  60

Gln Asn Leu Ser Val Ser Ser Asp Ser Tyr Leu Gln Leu Arg Asn Arg
65                  70                  75                  80

Arg Leu Lys Arg Pro Leu Ile Arg Gln His Ser Ala Lys Arg Asn Lys
                85                  90                  95

Gly His Asp Gly Asn Pro Lys Ser Pro Ile Gly Asp Ser Ile Ala Glu
            100                 105                 110

Glu Lys Thr Val Gln Lys Ser Pro Glu Pro Glu Asn Ala Glu Phe Lys
        115                 120                 125

Glu Asn Ala Glu Asp Thr Glu Arg Ser Ala Arg Glu Thr Thr Pro Val
    130                 135                 140

His Leu Ile Met Arg Ala Asp Val Leu Arg Pro Pro Arg Pro Ile Thr
```

```
            145                 150                 155                 160
Arg Arg Thr Phe Pro Thr Glu Ala Asn Pro Lys Thr Glu Gln Pro Thr
                165                 170                 175

Ile Pro Ile Ser Arg Glu Phe Glu Phe Cys Ala Lys His Glu Ala
        180                 185                 190

Glu Gln Gln Arg Glu Phe Met Glu Lys Tyr Asn Phe Asp Pro Val Thr
            195                 200                 205

Glu Gln Pro Leu Pro Gly Arg Tyr Glu Trp Glu Lys Val Ser Pro
    210                 215                 220

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 7
cgagatctga attcatggat cagta                                            25

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 8
cgagatctga attcctaagg catgcc                                           26

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 9
gggaatccat gggcggcggt taggagaag                                        29

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 10
ggcggatccc gtcttcttca tggattc                                          27

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 11
ggcgaatcca tggaagtctc taaagcaac                                        29
```

```
<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 12
ggcggatcct tttgaacttc atggtttgac                                       30

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 13
cggctcgagg agaaccacaa acacgc                                           26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 14
cgaaactagt taattacctc aaggaag                                          27

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 15
gatcccgggc gatatcagcg tcatgg                                           26

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 16
gatcccgggt tagtctgtta actcc                                            25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 17
gcagctacgg agccggagaa ttgt                                             24
```

```
<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Probe or
      Primer

<400> SEQUENCE: 18
tctccttctc gaaatcgaaa ttgtact                                            27

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Probe or
      Primer

<400> SEQUENCE: 19
cggctcgagg agaaccacaa acacgc                                             26

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Probe or
      Primer

<400> SEQUENCE: 20
cgaaactagt taattacctc aaggaag                                            27

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Probe or
      Primer

<400> SEQUENCE: 21
gatcccgggc gatatcagcg tcatgg                                             26

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Probe or
      Primer

<400> SEQUENCE: 22
gatcccgggt tagtctgtta actcc                                              25

<210> SEQ ID NO 23
<211> LENGTH: 69
<212> TYPE: DNA
<213> ORGANISM: Artificial Sequence
<220> FEATURE:
<223> OTHER INFORMATION: Description of Artificial Sequence: Probe or
      Primer

<400> SEQUENCE: 23
cccgctcgag atggtgagaa aatatagaaa agctaaagga tttgtagaag ctggagtttc        60
gtcaacgta                                                                69
```

```
<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 24
ggactagttc actctaactt tacccattcg                                              30

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 25
gatcatctta agcatcatcg tcttcttcat gg                                           32

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 26
taggagcata tggcggcgg                                                          19

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 27
atatcagcgc catggaagtc                                                         20

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 28
ggagctggat cctttggaa ttcatgg                                                  27

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 29
taggagcata tggcggcgg                                                          19
```

```
<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 30
atcatcgaat tcttcatgga ttc                                               23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 31
atatcagcgc catggaagtc                                                   20

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 32
ggagctggat cctttggaa ttcatgg                                            27

<210> SEQ ID NO 33
<211> LENGTH: 11
<212> TYPE: PRT
<213> ORGANISM: Arabidopsis thaliana
<220> FEATURE:
<221> NAME/KEY: UNSURE
<222> LOCATION: (5)
<223> OTHER INFORMATION: Xaa at postiion 5 may be Asp or Glu
<221> NAME/KEY: UNSURE
<222> LOCATION: (6)..(8)
<223> OTHER INFORMATION: Xaa at any of positions 6, 7 or 8 may be any
      amino acid

<400> SEQUENCE: 33

Val Arg Arg Arg Xaa Xaa Xaa Xaa Val Glu Glu
  1               5                  10

<210> SEQ ID NO 34
<211> LENGTH: 8
<212> TYPE: PRT
<213> ORGANISM: Arabidopsis thaliana
<220> FEATURE:
<221> NAME/KEY: UNSURE
<222> LOCATION: (2)..(3)
<223> OTHER INFORMATION: Xaa at positions 2 and 3 may be any amino acid

<400> SEQUENCE: 34

Phe Xaa Xaa Lys Tyr Asn Phe Asp
  1               5

<210> SEQ ID NO 35
<211> LENGTH: 8
<212> TYPE: PRT
<213> ORGANISM: Arabidopsis thaliana
<220> FEATURE:
<221> NAME/KEY: UNSURE
```

```
<222> LOCATION: (1)
<223> OTHER INFORMATION: Xaa at position 1 may be Pro or Leu
<221> NAME/KEY: UNSURE
<222> LOCATION: (3)
<223> OTHER INFORMATION: Xaa at position 3 may be any amino acid

<400> SEQUENCE: 35

Xaa Leu Xaa Gly Arg Tyr Glu Trp
  1               5

<210> SEQ ID NO 36
<211> LENGTH: 10
<212> TYPE: PRT
<213> ORGANISM: Arabidopsis thaliana
<220> FEATURE:
<221> NAME/KEY: UNSURE
<222> LOCATION: (2)
<223> OTHER INFORMATION: Xaa at position 2 may be any amino acid
<221> NAME/KEY: UNSURE
<222> LOCATION: (4)
<223> OTHER INFORMATION: Xaa at position 4 may be Asp or Glu
<221> NAME/KEY: UNSURE
<222> LOCATION: (7)..(9)
<223> OTHER INFORMATION: Xaa at positions 7, 8 or 9 may be any amino
      acid

<400> SEQUENCE: 36

Glu Xaa Glu Xaa Phe Phe Xaa Xaa Xaa Glu
  1               5                  10

<210> SEQ ID NO 37
<211> LENGTH: 8
<212> TYPE: PRT
<213> ORGANISM: Arabidopsis thaliana
<220> FEATURE:
<221> NAME/KEY: UNSURE
<222> LOCATION: (2)
<223> OTHER INFORMATION: Xaa at position 2 may be any amino acid

<400> SEQUENCE: 37

Tyr Xaa Gln Leu Arg Ser Arg Arg
  1               5

<210> SEQ ID NO 38
<211> LENGTH: 9
<212> TYPE: PRT
<213> ORGANISM: Arabidopsis thaliana
<220> FEATURE:
<221> NAME/KEY: UNSURE
<222> LOCATION: (5)
<223> OTHER INFORMATION: Xaa at position 5 may be Met or Ile
<221> NAME/KEY: UNSURE
<222> LOCATION: (6)
<223> OTHER INFORMATION: Xaa at position 6  may be Lys or Arg
<221> NAME/KEY: UNSURE
<222> LOCATION: (8)
<223> OTHER INFORMATION: Xaa at position 8 may be any amino acid
<221> NAME/KEY: UNSURE
<222> LOCATION: (9)
<223> OTHER INFORMATION: Xaa at position 9 may be Lys or Arg

<400> SEQUENCE: 38

Met Gly Lys Tyr Xaa Xaa Lys Xaa Xaa
  1               5

<210> SEQ ID NO 39
<211> LENGTH: 8
<212> TYPE: PRT
<213> ORGANISM: Arabidopsis thaliana
<220> FEATURE:
<221> NAME/KEY: UNSURE
```

<222> LOCATION: (2)
<223> OTHER INFORMATION: Xaa at position 2 may be any amino acid

<400> SEQUENCE: 39

Ser Xaa Gly Val Arg Thr Arg Ala
 1               5

<210> SEQ ID NO 40
<211> LENGTH: 327
<212> TYPE: PRT
<213> ORGANISM: Arabidopsis thaliana

<400> SEQUENCE: 40

Met Gly Lys Tyr Ile Arg Lys Ser Lys Ile Asp Gly Ala Gly Ala Gly
 1               5                  10                  15

Ala Gly Gly Gly Gly Gly Gly Gly Gly Glu Ser Ser Ile Ala
                20                  25                  30

Leu Met Asp Val Val Ser Pro Ser Ser Ser Ser Leu Gly Val Leu
                35                  40                  45

Thr Arg Ala Lys Ser Leu Ala Leu Gln Gln Gln Gln Arg Cys Leu
    50                  55                  60

Leu Gln Lys Pro Ser Ser Pro Ser Ser Leu Pro Pro Thr Ser Ala Ser
65                  70                  75                  80

Pro Asn Pro Ser Lys Gln Lys Met Lys Lys Lys Gln Gln Met
                85                  90                  95

Asn Asp Cys Gly Ser Tyr Leu Gln Leu Arg Ser Arg Arg Leu Gln Lys
                100                 105                 110

Lys Pro Pro Ile Val Val Ile Arg Ser Thr Lys Arg Arg Lys Gln Gln
                115                 120                 125

Arg Arg Asn Glu Thr Cys Gly Arg Asn Pro Asn Pro Arg Ser Asn Leu
    130                 135                 140

Asp Ser Ile Arg Gly Asp Gly Ser Arg Ser Asp Ser Val Ser Glu Ser
145                 150                 155                 160

Val Val Phe Gly Lys Asp Lys Asp Leu Ile Ser Glu Ile Asn Lys Asp
                165                 170                 175

Pro Thr Phe Gly Gln Asn Phe Phe Asp Leu Glu Glu Glu His Thr Gln
                180                 185                 190

Ser Phe Asn Arg Thr Thr Arg Glu Ser Thr Pro Cys Ser Leu Ile Arg
                195                 200                 205

Arg Pro Glu Ile Met Thr Thr Pro Gly Ser Ser Thr Lys Leu Asn Ile
    210                 215                 220

Cys Val Ser Glu Ser Asn Gln Arg Glu Asp Ser Leu Ser Arg Ser His
225                 230                 235                 240

Arg Arg Arg Pro Thr Thr Pro Glu Met Asp Glu Phe Phe Ser Gly Ala
                245                 250                 255

Glu Glu Glu Gln Gln Lys Gln Phe Ile Glu Lys Tyr Val Phe Pro Arg
                260                 265                 270

Phe Ile Cys Ser Val Leu Leu Val Met Ser Phe Gln Phe Val Leu Phe
                275                 280                 285

Phe Ser Phe Gly Leu Val Ser Leu Met Val Ser Val Asn Ser Phe Phe
                290                 295                 300

Arg Tyr Asn Phe Asp Pro Val Asn Glu Gln Pro Leu Pro Gly Arg Phe
305                 310                 315                 320

Glu Trp Thr Lys Val Asp Asp
                325

```
<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence:  Probe or
      Primer

<400> SEQUENCE: 41
agaccatggc ggcggttagg ag                                            22

<210> SEQ ID NO 42
<211> LENGTH: 12
<212> TYPE: PRT
<213> ORGANISM: Tag100 epitope

<400> SEQUENCE: 42

Glu Glu Thr Ala Arg Phe Gln Pro Gly Tyr Arg Ser
1               5                   10

<210> SEQ ID NO 43
<211> LENGTH: 10
<212> TYPE: PRT
<213> ORGANISM: c-myc epitope

<400> SEQUENCE: 43

Glu Gln Lys Leu Ile Ser Glu Glu Asp Leu
1               5                   10

<210> SEQ ID NO 44
<211> LENGTH: 7
<212> TYPE: PRT
<213> ORGANISM: FLAG-epitope

<400> SEQUENCE: 44

Asp Tyr Lys Asp Asp Asp Lys
1               5

<210> SEQ ID NO 45
<211> LENGTH: 9
<212> TYPE: PRT
<213> ORGANISM: HA-epitope

<400> SEQUENCE: 45

Tyr Pro Tyr Asp Val Pro Asp Tyr Ala
1               5

<210> SEQ ID NO 46
<211> LENGTH: 12
<212> TYPE: PRT
<213> ORGANISM: protein C epitope

<400> SEQUENCE: 46

Glu Asp Gln Val Asp Pro Arg Leu Ile Asp Gly Lys
1               5                   10

<210> SEQ ID NO 47
<211> LENGTH: 11
<212> TYPE: PRT
<213> ORGANISM: VSV epitope

<400> SEQUENCE: 47

Tyr Thr Asp Ile Glu Met Asn Arg Leu Gly Lys
1               5                   10
```

```
<210> SEQ ID NO 48
<211> LENGTH: 9
<212> TYPE: DNA
<213> ORGANISM: Escherichia coli

<400> SEQUENCE: 48 agg aga aga                                                            9
Arg Arg Arg
 1
```